US010583091B2

(12) United States Patent
Shi et al.

(10) Patent No.: US 10,583,091 B2
(45) Date of Patent: Mar. 10, 2020

(54) AMPHIPHILE-POLYMER PARTICLES

(71) Applicants: The Brigham and Women's Hospital, Inc., Boston, MA (US); President and Fellows of Harvard College, Cambridge, MA (US)

(72) Inventors: Jinjun Shi, Boston, MA (US); Xi Zhu, Qingdao (CN); Omid C. Farokhzad, Waban, MA (US); Xiaoding Xu, Malden, MA (US); Yanlan Liu, Boston, MA (US); Aude Thiriot, Brookline, MA (US); Ulrich Von Andrian, Chestnut Hill, MA (US)

(73) Assignees: The Brigham and Women's Hospital, Inc., Boston, MA (US); President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 15/520,796

(22) PCT Filed: Oct. 23, 2015

(86) PCT No.: PCT/US2015/057194
§ 371 (c)(1),
(2) Date: Apr. 20, 2017

(87) PCT Pub. No.: WO2016/065306
PCT Pub. Date: Apr. 28, 2016

(65) Prior Publication Data
US 2017/0304213 A1     Oct. 26, 2017

Related U.S. Application Data

(60) Provisional application No. 62/067,744, filed on Oct. 23, 2014.

(51) Int. Cl.
| | | |
|---|---|---|
| *A61K 9/51* | (2006.01) | |
| *A61K 9/50* | (2006.01) | |
| *A61K 47/64* | (2017.01) | |
| *A61K 31/713* | (2006.01) | |
| *A61K 38/43* | (2006.01) | |
| *A61K 48/00* | (2006.01) | |

(52) U.S. Cl.
CPC .......... *A61K 9/5153* (2013.01); *A61K 9/5021* (2013.01); *A61K 9/5031* (2013.01); *A61K 9/5078* (2013.01); *A61K 9/5146* (2013.01); *A61K 31/713* (2013.01); *A61K 38/43* (2013.01); *A61K 47/64* (2017.08); *A61K 48/0041* (2013.01); *Y02A 50/401* (2018.01); *Y02A 50/475* (2018.01); *Y02A 50/481* (2018.01)

(58) Field of Classification Search
CPC .... A61K 9/5153; A61K 47/64; A61K 9/5146; A61K 31/713; A61K 38/43; A61K 48/0041
See application file for complete search history.

(56) References Cited

U.S. PATENT DOCUMENTS

2013/0302433 A1* 11/2013 Troiano .................. A61K 9/10
                                                        424/501
2013/0344158 A1    12/2013 Zale et al.

OTHER PUBLICATIONS

Beena Ashok, et al, In Vitro Characterization of PEGylated Phospholipid Micelles for Improved Drug Solubilization: Effects of PEG Chain Length and PC Incorporation, 93 J Pharm Sci. 2476 (Year: 2004).*
International Search Report and Written Opinion dated Jan. 19, 2016 in international application No. PCT/US2015/057194, 12 pgs.
Chan et al., "PLGA-lecithin-PEG core-shell nanoparticles for controlled drug delivery," Biomaterials 30: 1627-1634 (2009).
'www.dicerna.com' [online]. "Theraputic Approach—EnCore Lipid Nanoparticles," [retrieved on Oct. 6, 2014], retrieved from the Internet URL: <http://www.dicerna.com/approach-about-lnp.php>. 1 page.
Alexis et al., "Factors affecting the clearance and biodistribution of polymeric nanoparticles," Mol. Pharm, 2008, 5: 505-515.
Barbie et al., "Systematic RNA interference reveals that oncogenic KRAS-driven cancers require TBK1," Nature, 2009, 462: 108-112.
Bartlett et al., "Impact of tumor-specific targeting on the biodistribution and efficacy of siRNA nanoparticles measured by multimodality in vivo imaging," PNAS, 2007, 104: 15549-15554.
Bertrand et al., "Cancer nanotechnology: the impact of passive and active targeting in the era of modern cancer biology," Adv. Drug Deliv. Rev, Feb. 2014, 66: 2-25.
Cevc, "How membrane chain-melting phase-transition temperature is affected by the lipid chain asymmetry and degree of unsaturation: an effective chain-length model," Biochemistry, 1991, 30: 7186-7193.
Cheng et al., "Analytical measurement of PEGylated molecules," Bioconjug. Chem, 2012, 23: 881-899.
Creixell and Peppas, "Co-delivery of siRNA and therapeutic agents using nanocarriers to overcome cancer resistance," Nano Today, Aug. 2012, 7: 367-379.
Davis, "The first targeted delivery of siRNA in humans via a self-assembling, cyclodextrin polymer-based nanoparticle: from concept to clinic," Mol. Pharm, 2009, 6: 659-668.
Diez et al., "Targeted cationic poly(D,L-lactic-co-glycolic acid) nanoparticles for gene delivery to cultured cells," Cell. Mol. Biol. Lett, 2009, 14: 347-362.
Gilleron et al., "Image-based analysis of lipid nanoparticle-mediated siRNA delivery, intracellular trafficking and endosomal escape," Nat. Biotechnol, 2013, 31: 638-646.

(Continued)

*Primary Examiner* — Sean M Basquill
(74) *Attorney, Agent, or Firm* — Fish & Richardson P.C.

(57) ABSTRACT

This invention relates to amphiphile-polymer particles comprising obtaining a first solution comprising a water-insoluble polymer, a payload and a first amphiphile in a water-miscible solvent; mixing the first solution with an aqueous second solution to form an aqueous composition comprising a particle comprising a water-insoluble polymeric core comprising the water-insoluble polymer; the payload; and the first amphiphile.

20 Claims, 66 Drawing Sheets

(56) References Cited

OTHER PUBLICATIONS

Gregory-Bass et al., "Prohibitin silencing reverses stabilization of mitochondrial integrity and chemoresistance in ovarian cancer cells by increasing their sensitivity to apoptosis," Int. J. Cancer, May 2008, 122: 1923-1930.
Guo and Huang, "Recent advances in nonviral vectors for gene delivery," Acc. Chem. Res, Jul. 2012, 45: 971-979.
Hirsch, "The use of RNAi-based screens to identify host proteins involved in viral replication," Feb. 2010, 5: 303-311.
International Preliminary Report on Patentability in International Application No. PCT/US2015/057194, dated Apr. 25, 2017, 6 pages.
Jain and Stylianopoulos, "Delivering nanomedicine to solid tumors," Nat. Rev. Clin. Oncol, Nov. 2010, 7: 653-664.
Judge et al., "Sequence-dependent stimulation of the mammalian innate immune response by synthetic siRNA," Nat. Biotechnol, Apr. 2005, 23: 457-462.
Kanasty et al., "Delivery materials for siRNA therapeutics," Nat. Mater, Nov. 2013, 12: 967-977.
Kapoor, "Prohibitin and its rapidly emerging role as a biomarker of systemic malignancies," Hum. Pathol, Apr. 2013, 44: 678-679.
Kong et al., "Hyperthermia Enables Tumor-specific Nanoparticle Delivery: Effect of Particle Size," Cancer Research, Aug. 2000, 60: 4440-4445.
Li and Huang, "Stealth nanoparticles: high density but sheddable PEG is a key for tumor targeting," J. Control. Release, Mar. 2010, 145: 178-181.
Liu et al., "A High-Performance Ytterbium-Based Nanoparticulate Contrast Agent for in Vivo X-Ray Computed Tomography Imaging," Angew. Chem. Int. Ed., Feb. 2012, 51: 1437-1442.
Liu et al., "Structure-based programming of lymph-node targeting in molecular vaccines," Nature, Mar. 2014, 507: 519-522.
Love et al., "Lipid-like materials for low-dose, in vivo gene silencing," PNAS, 2010, 107: 1864-1869.
MacLachlan, "Lipid Nanoparticle-Mediated Delivery of Messenger RNA," 1$^{st}$ International mRNA Health Conference, Oct. 2013, 32 pages.
Molina et al., "Non-small cell lung cancer: epidemiology, risk factors, treatment, and survivorship," Mayo Clin. Proc, May 2008, 83: 584-594.
Nuell et al., "Prohibitin, an evolutionarily conserved intracellular protein that blocks DNA synthesis in normal fibroblasts and HeLa cells," Mol. Cell. Biol, 1991, 11: 1372-1381.
Patel et al., "Rescue of paclitaxel sensitivity by repression of Prohibitin1 in drug-resistant cancer cells," PNAS, Feb. 2010, 107: 2503-2508.
Pecot et al., "RNA interference in the clinic: challenges and future directions," Nat. Rev. Cancer, Jan. 2011, 11: 59-67.
Ren et al., "Targeted tumor-penetrating siRNA nanocomplexes for credentialing the ovarian cancer oncogene ID4," Sci. Transl. Med, Aug. 2012, 4: 147ra112.
Robbins et al., "Misinterpreting the therapeutic effects of small interfering RNA caused by immune stimulation," Hum. Gene Ther, Oct. 2008, 19: 991-999.
Romberg et al., "Sheddable coatings for long-circulating nanoparticles," Pharm. Res, Jan. 2008, 25: 55-71.
Shi et al., "Differentially charged hollow core/shell lipid-polymer-lipid hybrid nanoparticles for small interfering RNA delivery," Angew. Chem. Int. Ed. Engl, Jul. 2011, 50: 7027-7031.
Shi et al., "Hybrid lipid-polymer nanoparticles for sustained siRNA delivery and gene silencing," Nanomedicine, Jul. 2014, 10: 897-900.
Su et al., "In vitro and in vivo mRNA delivery using lipid-enveloped pH-responsive polymer nanoparticles," Mol Pharm, Jun. 2011, 8: 774-787.
Tabas and Glass, "Anti-Inflammatory Therapy in Chronic Disease: Challenges and Opportunities," Science, Jan. 2013, 339 (6116): 166-172.
Tabernero et al., "First-in-humans trial of an RNA interference therapeutic targeting VEGF and KSP in cancer patients with liver involvement," Cancer Discov, 2013, 3: 406-417.
Theiss and Sitaraman, "The role and therapeutic potential of prohibitin in disease," Biochim. Biophys. Acta, Jun. 2011, 1813: 1137-1143.
Wheeler et al., "Stabilized plasmid-lipid particles: construction and characterization," Gene Ther, 1999, 6: 271-281.
Whitehead et al., "Knocking down barriers: advances in siRNA delivery," Nat. Rev. Drug Discov, 2009, 8: 129-138.
Wilson et al., "Orally delivered thioketal-nanoparticles loaded with TNF-alpha-siRNA target inflammation and inhibit gene expression in the intestines," Nat. Mater, Nov. 2010, 9: 923-928.
Woodrow et al., "Intravaginal gene silencing using biodegradable polymer nanoparticles densely loaded with small-interfering RNA," Nat. Mater, Jun. 2009, 8: 526-533.
Xu et al., "Enhancing tumor cell response to chemotherapy through nanoparticle-mediated codelivery of siRNA and cisplatin prodrug," PNAS, Oct. 2013, 110: 18638-18643.
Zhang et al., "In vivo gene delivery by nonviral vectors: overcoming hurdles?," Mol. Ther, Jul. 2012, 20: 1298-1304.
Zhu et al., "Nanotechnology-Mediated Nucleic Acid Delivery for prostate Cancer Therapy," poster, Presented at 21st Prostate Cancer Foundation Annual Scientific Retreat in Carlsbad, CA, Oct. 23-25, 2014, 1 page.
Zuckerman et al., "Correlating animal and human phase Ia/Ib clinical data with CALAA-01, a targeted, polymer-based nanoparticle containing siRNA," PNAS, Jul. 2014, 111: 11449-11454.

* cited by examiner

Small molecular drug, adjuvant, or imaging agent

Lipid-PEG

Nucleic acid (e.g., siRNA, microRNA, and mRNA) or others like protein and peptide Cationic amphiphilic materials Lecithin or other amphiphilic materials Polymer (e.g., PLGA, PLA, PCL, or fluorescent F8BT)

Targeting ligand

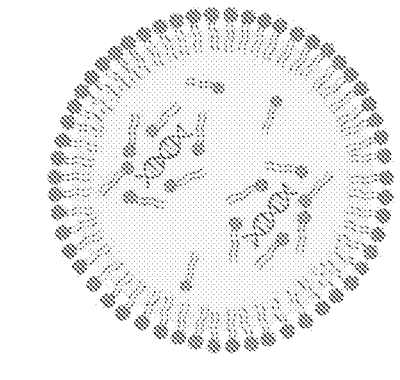
FIG. 3C
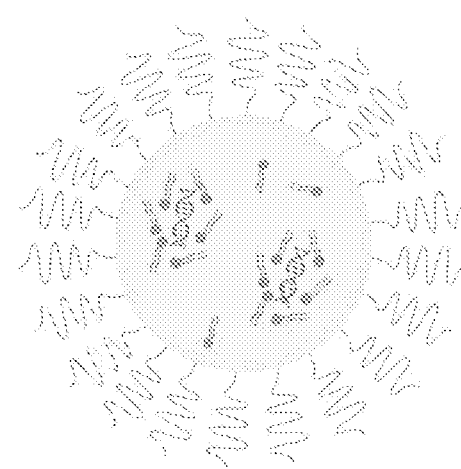
FIG. 3F
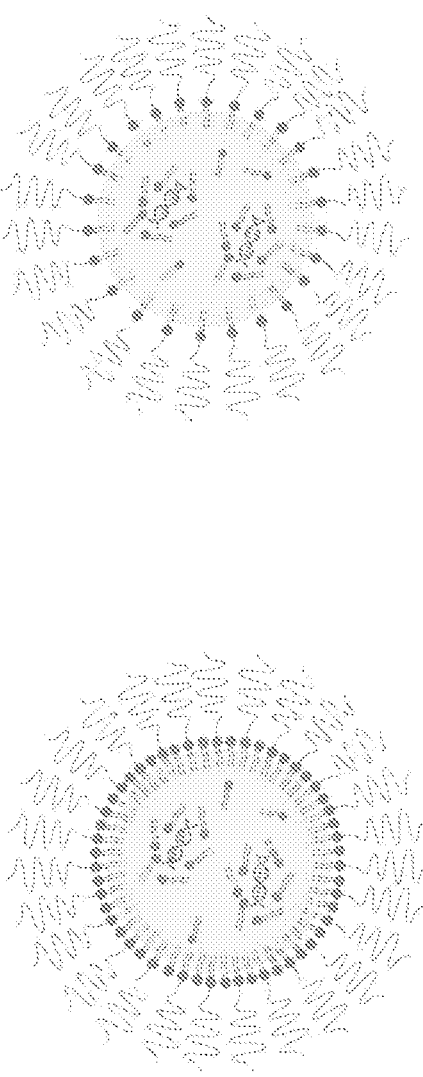
FIG. 3B
FIG. 3A
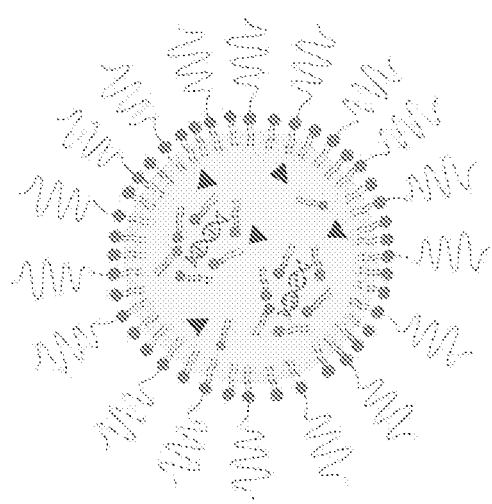
FIG. 3E
FIG. 3D

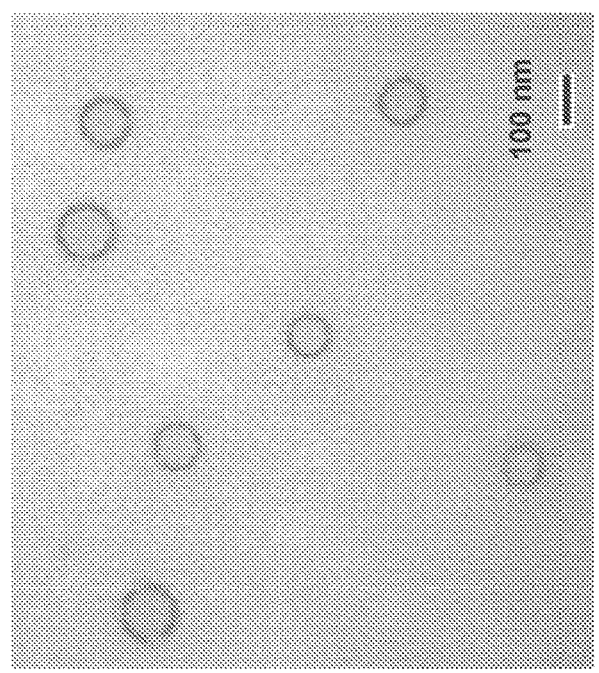
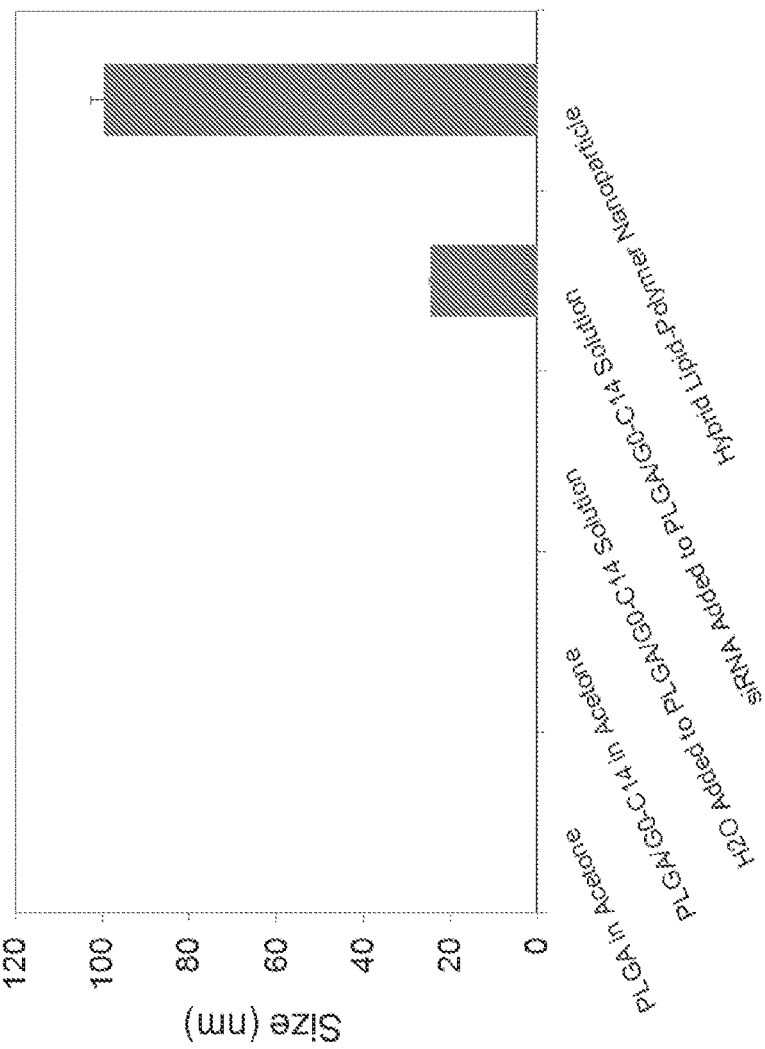
FIG. 4B
FIG. 4A

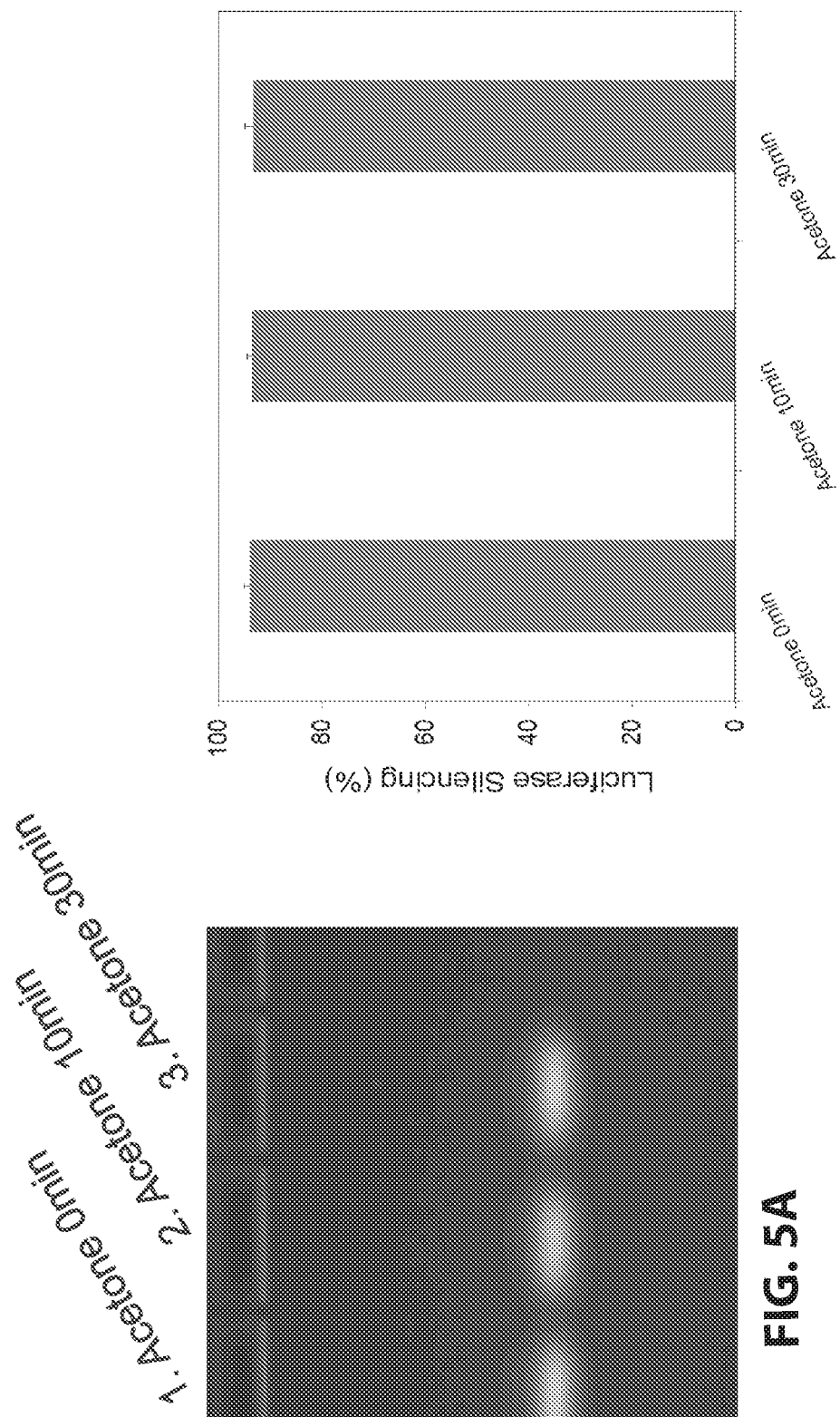
FIG. 5B
FIG. 5A

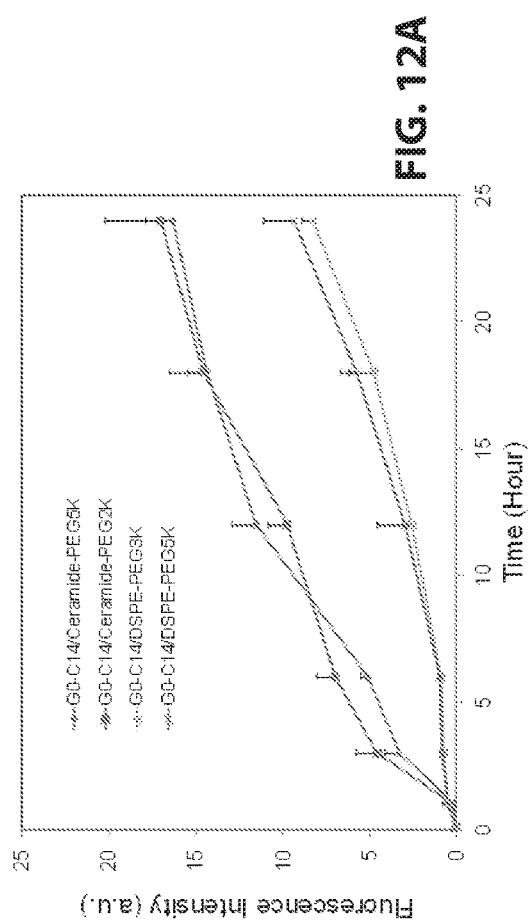
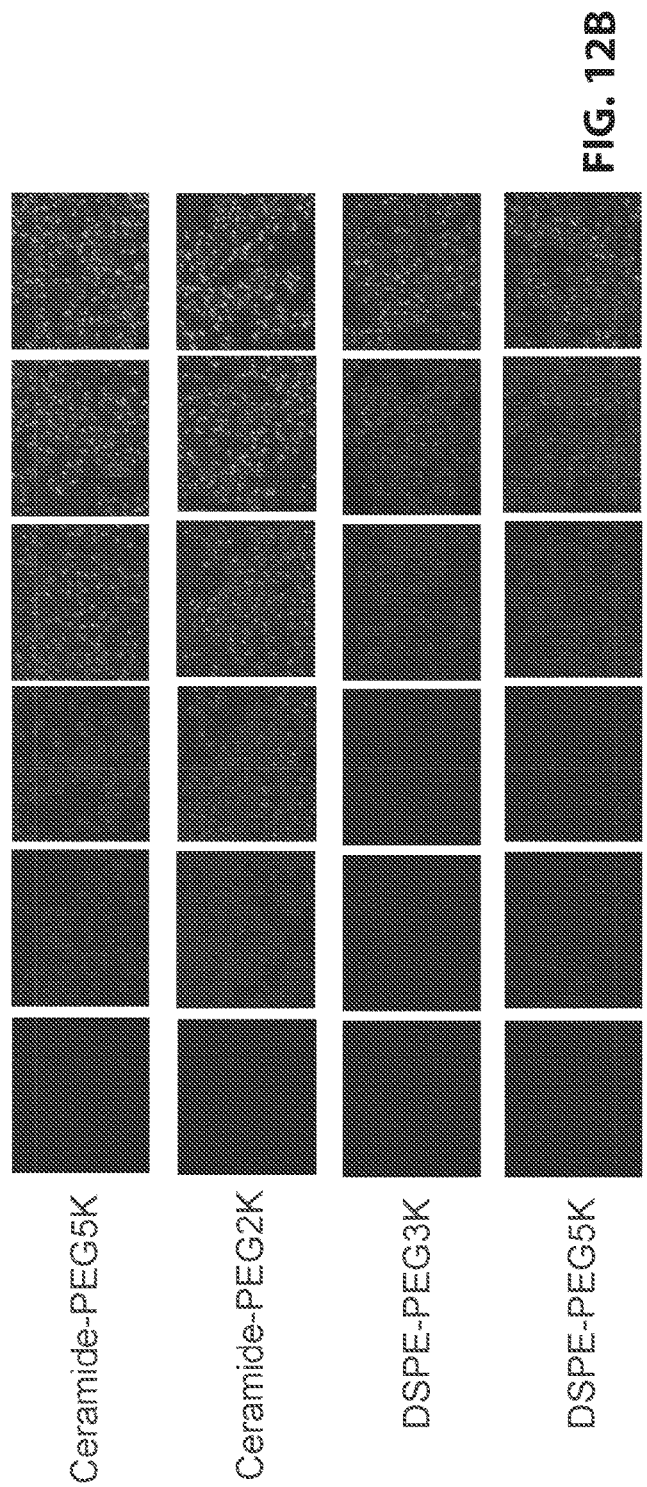
FIG. 12A
FIG. 12B

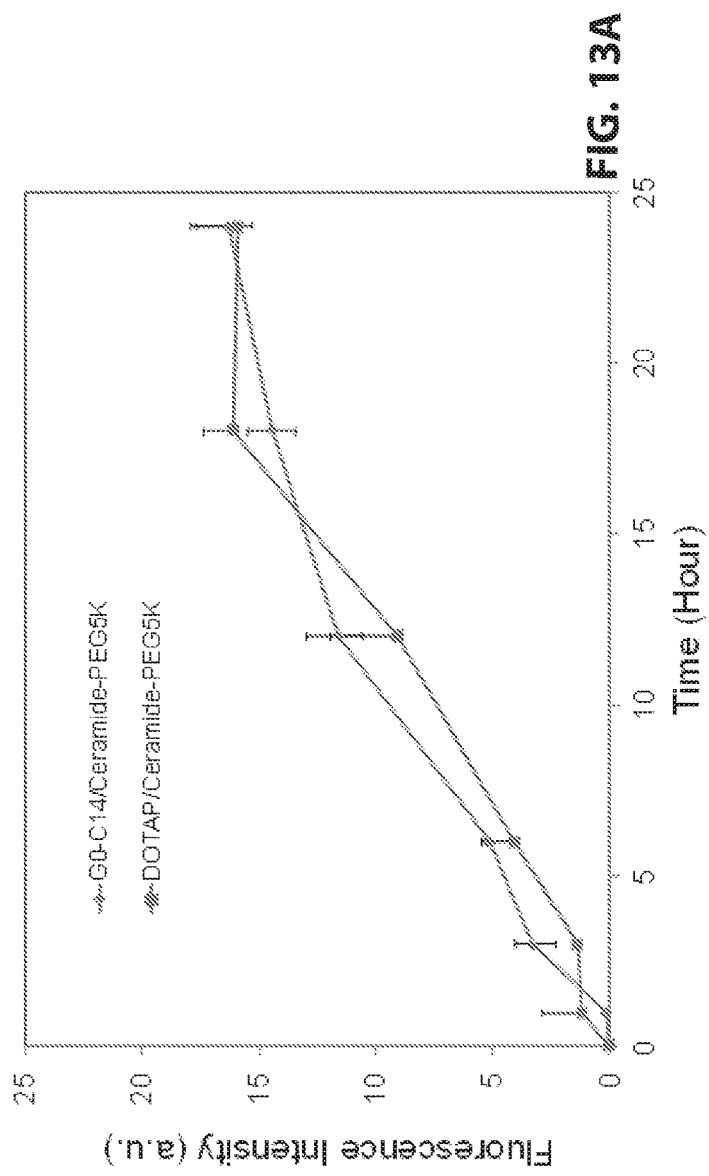
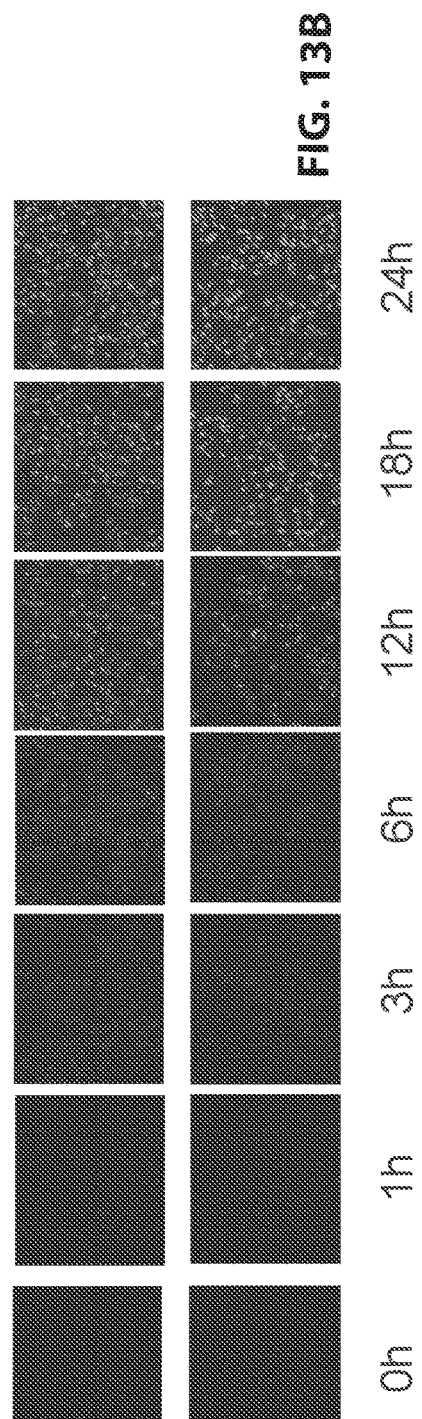
FIG. 13A
FIG. 13B

Ceramide-PEG5K NPs

DSPE-PEG5K NPs

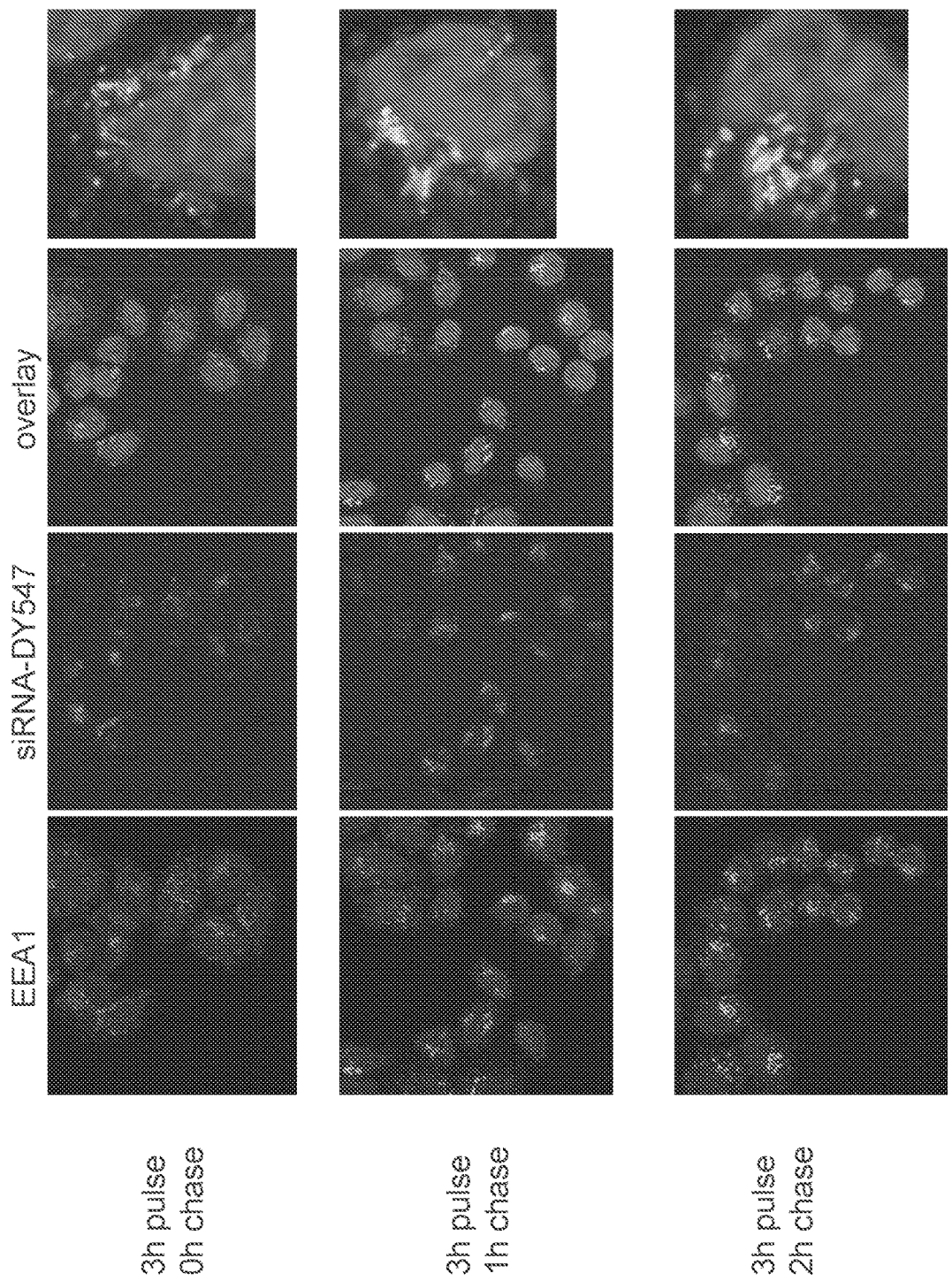

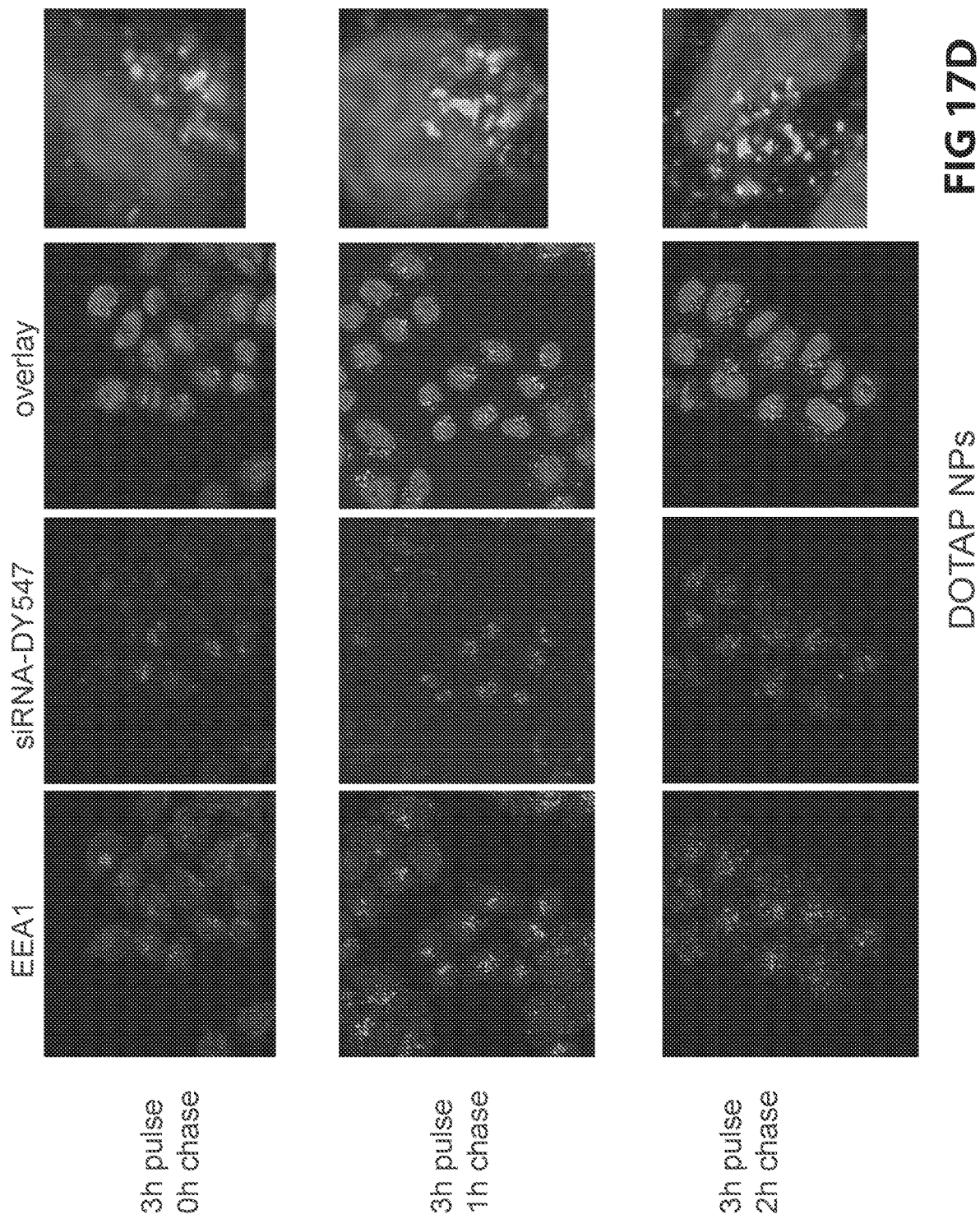

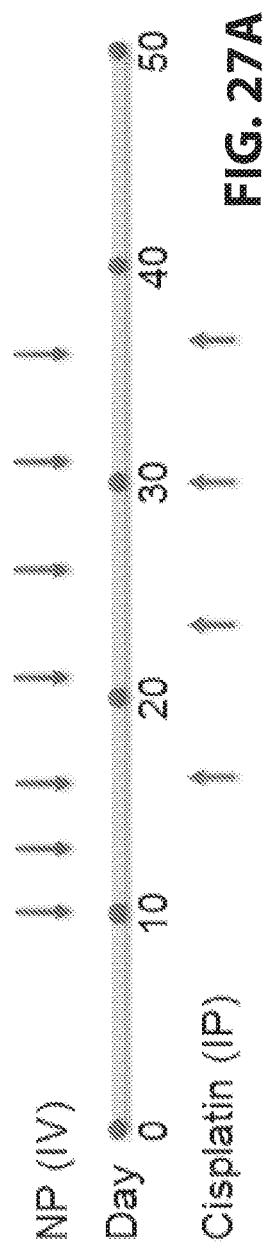
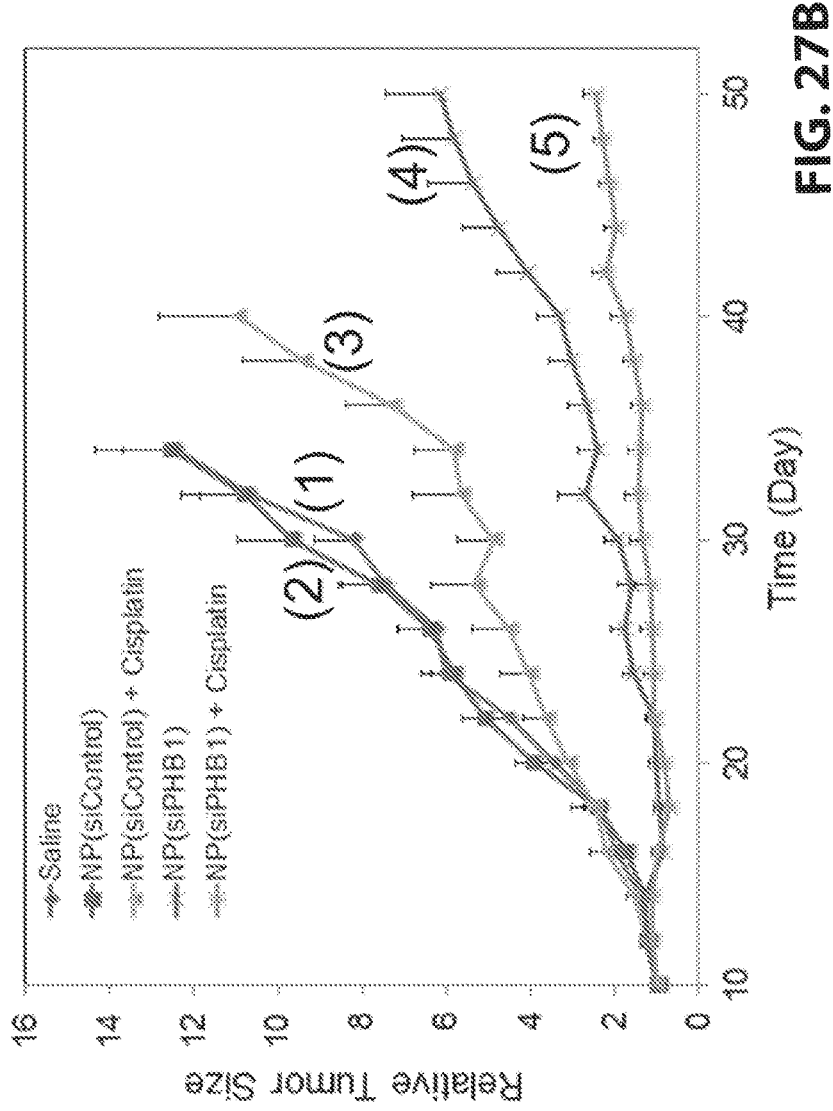

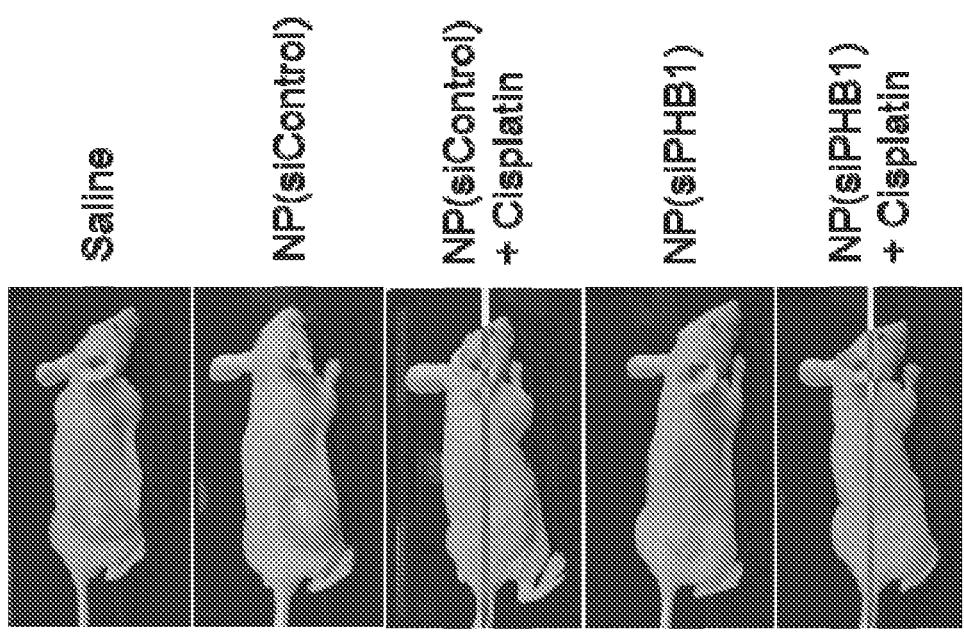
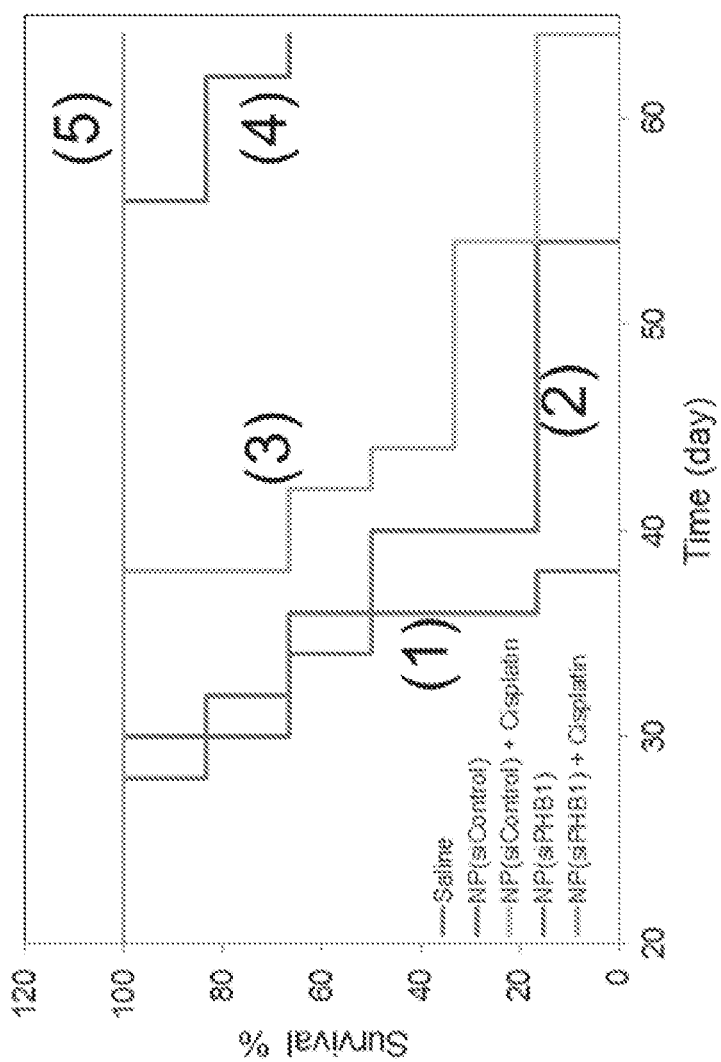
FIG. 27D
FIG. 27C

Naked mRNA

Lipo2K/mRNA mRNA NPs

Myc/Hematoxylin

DAP/Myc/Actin

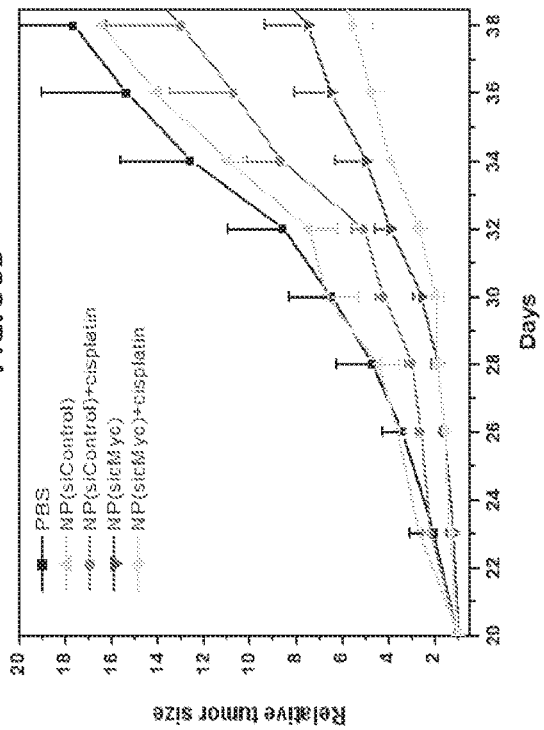
FIG. 38B
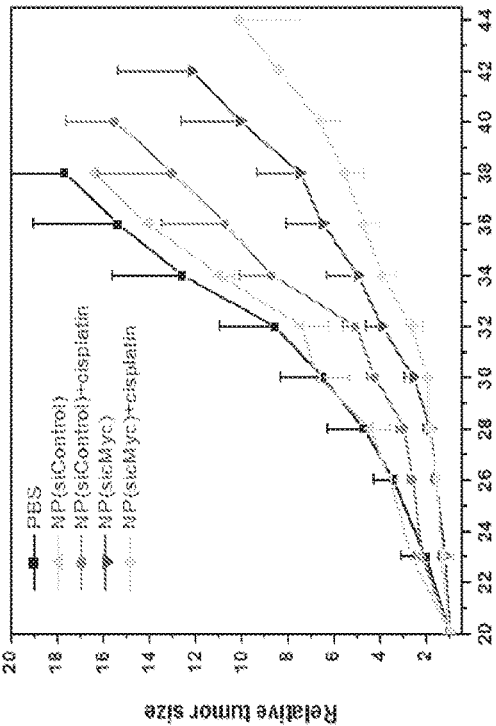
FIG. 38C
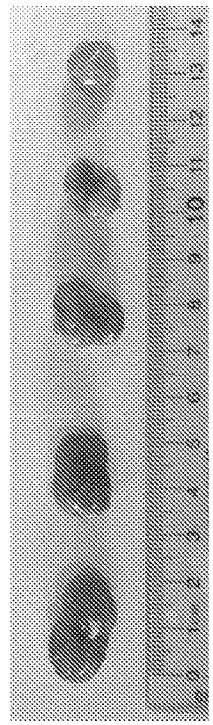
FIG. 38A
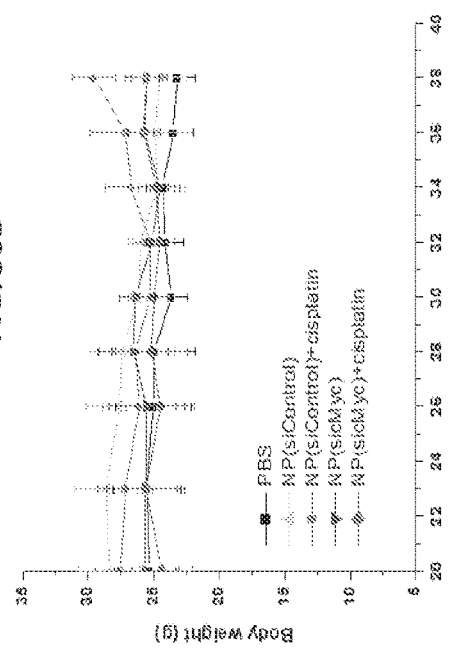
FIG. 38D
FIG. 38E

AMPHIPHILE-POLYMER PARTICLES

CLAIM OF PRIORITY

This application is a § 371 National Stage Application of PCT/US2015/057194, filed Oct. 23, 2015, which claims the benefit of U.S. Provisional Application No. 62/067,744, filed Oct. 23, 2014. The entire contents of the foregoing are hereby incorporated by reference.

STATEMENT AS TO FEDERALLY SPONSORED RESEARCH

This invention was made with Government support under Grant Nos. R00CA160350, EB015419 and U54-CA151884, awarded by the National Institutes of Health. The Government has certain rights in the invention.

TECHNICAL FIELD

This invention relates to amphiphile-polymer particles, compositions, methods of making, and methods of use thereof.

BACKGROUND

The medical application of nanotechnology has a significant impact on the economy. In 2004, nanomedicine sales reached 6.8 billion dollars, with over 200 companies and 38 products worldwide. It is estimated that a minimum of 3.8 billion dollars in nanotechnology research and development is being invested every year. The introduction of nanoparticles for the treatment, prevention, and diagnosis of major human diseases is expected to result in an expansion in the use of this class of biomaterials. A platform by which nanoparticles may be developed and optimized for targeting applications may facilitate the introduction of novel therapeutic and diagnostic modalities for treatment of a myriad of diseases including various forms of solid tumors, inflammatory diseases, and viral infections.

One application of nanoparticles is drug delivery. There is a need for new particle formulations that can be used to encapsulate drugs.

SUMMARY

Provided herein is a particle comprising a water-insoluble polymeric core and a payload and a first amphiphile within the core.

Also provided herein is a particle prepared by a process comprising obtaining a first solution comprising a water-insoluble polymer, a payload and a first amphiphile in a water-miscible solvent; mixing the first solution with an aqueous second solution to form an aqueous composition comprising a particle comprising a water-insoluble polymeric core comprising the water-insoluble polymer; the payload; and the first amphiphile.

Also provided is a composition comprising a particle as described herein, and a pharmaceutically acceptable carrier.

Provided is a method of preparing a particle as described herein comprising: obtaining a first solution comprising a water-insoluble polymer, a payload and a first amphiphile in a water-miscible solvent; mixing the first solution with an aqueous second solution to form an aqueous composition comprising a particle as described herein.

Also provided is a method of administering a therapeutic payload to a subject in need thereof, comprising administering to the subject one or more particles, or a composition, as described herein, wherein the one or more particles is administered in an amount that provides to the subject a therapeutically effective amount of the payload.

Also provided is a method of treating a cancer in a subject in need thereof, the method comprising administering to the subject a therapeutically effective amount of a particle or a composition as described herein, wherein the payload is indicated for treatment of the cancer.

Provided herein is a method of treating a disease or a condition in need of enzyme replacement in a subject in need thereof, the method comprising administering to the subject a therapeutically effective amount of a particle or a composition as described herein, wherein the payload is indicated for treating the disease or condition in need of enzyme replacement.

Also provided herein is a method of preventing or treating a viral disease in a subject in need thereof, the method comprising administering to the subject a therapeutically effective amount of a particle or a composition as described herein, wherein the payload is indicated for treatment of the viral disease.

Also provided herein is a method of treating an inflammatory disease in a subject in need thereof, the method comprising administering to the subject a therapeutically effective amount of a particle or a composition as described herein, wherein the payload is indicated for treatment of the inflammatory disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the description and drawings, and from the claims.

DESCRIPTION OF DRAWINGS

FIG. 3 is a diagram showing different types of particle structures. The particles can have a structure composed of a water-insoluble polymer-amphiphile hybrid core surrounded by a lipid and lipid-PEG layer (FIG. 3A), or lipid-PEG layer (FIG. 3B), or lipid layer (FIG. 3C). The outer shell can be modified with a targeting molecule (FIG. 3D). The core can further carry a second payload (FIG. 3E). A PEG molecule can be first conjugated with the polymer before the formulation process and form particles without an outer shell (FIG. 3F).

FIG. 4 is chart and diagram showing siRNA NP size and structure. FIG. 4A: Particle size at different stages in the formulation process, measured by dynamic light scattering. FIG. 4B: Transmission electron microscopy (TEM) image of the NPs. Samples for TEM were stained with 1% uranyl acetate and observed using Tecnai $G^2$ Spirit BioTWIN microscope (FEI Company, Hillsboro, Oreg.) operating at 80 kV.

FIG. 5 shows siRNA stability in acetone. FIG. 5A: The stability of siRNA molecules after 10 or 30 min post-acetone treatment. FIG. 5B: Effect of acetone treatment on the silencing effect of siRNA. To test the silencing activity of siRNA, anti-Luciferase siRNA (siLuc) that been treated with acetone was mixed with Lipofectimine2000 according to the manufacturer's protocol. Luciferase expressing HeLa cells were transfected with the Lipofectimine2000-complexed siLuc. Expression of firefly luciferase in HeLa cells was determined using Luciferase assay kits (Promega).

FIG. 6. Effect of cationic lipids and lipid-PEGs on siRNA encapsulation efficiency and NP size.

FIG. 8 shows the effect of cationic lipids and lipid-PEGs on luciferase silencing in vitro.

FIG. 9 shows the effect of N/P ratio on silencing and encapsulation efficiency.

FIG. 12 shows the effect of lipid-PEGs on cellular uptake kinetics in HeLa cells. (A) Quantification of cellular uptake kinetics of NP(DY547-siRNA) prepared with different lipid-PEGs. (B) Examples of cell uptake images of different NPs. For cellular uptake kinetics study, HeLa cells were incubated with NP(DY547-siRNA) for different time periods (1 h, 3 h, 6 h, 12 h, 18 h, and 24 h), and then washed with PBS, fixed with 4% paraformaldehyde and stained with Hoechst (2 µg/mL) for nuclei identification. Images were acquired on inverted fluorescence microscope (Zeiss Axiovert 200) and analyzed using Fiji/Image-J software.

FIG. 13 shows the effect of cationic lipids on cellular uptake kinetics in HeLa cells. (A) Quantification of cellular uptake kinetics of NPs prepared with two different cationic lipids (G0-C14 vs. DOTAP). (B) Examples of uptake pictures of different NP(DY547-siRNA). HeLa cells were incubated with NP(DY547-siRNA) for different time periods (1 h, 3 h, 6 h, 12 h, 18 h, and 24 h), and then washed with PBS, fixed with 4% paraformaldehyde and stained with Hoechst (2 µg/mL) for nuclei identification. Images were acquired on inverted fluorescence microscope (Zeiss Axiovert 200) and analyzed using Fiji/Image-J software.

Organs were harvested 2 days after the final injection of 3 daily intravenous injections (600 µg siRNA/kg), fixed with 4% paraformaldehyde, and embedded in paraffin. Tissue sections were stained with H&E.

Figure 25A:
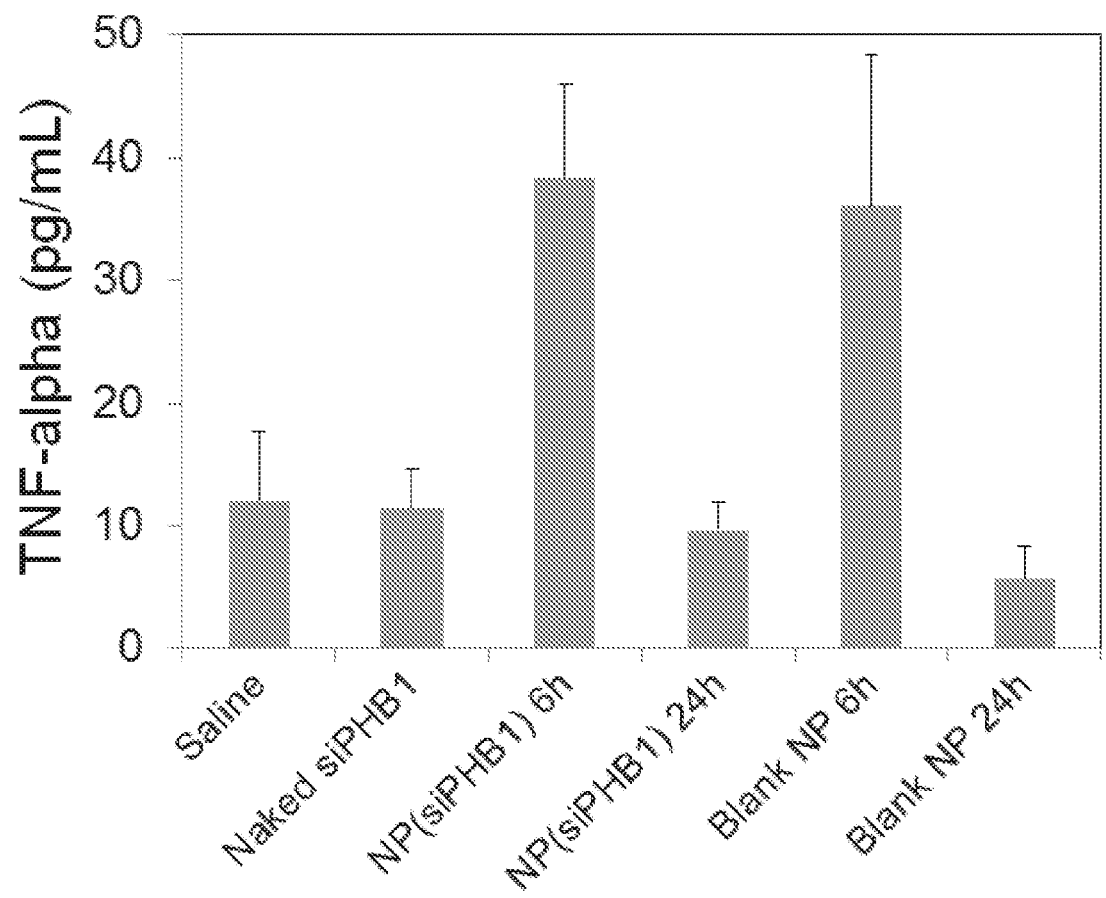
Figure 25B:
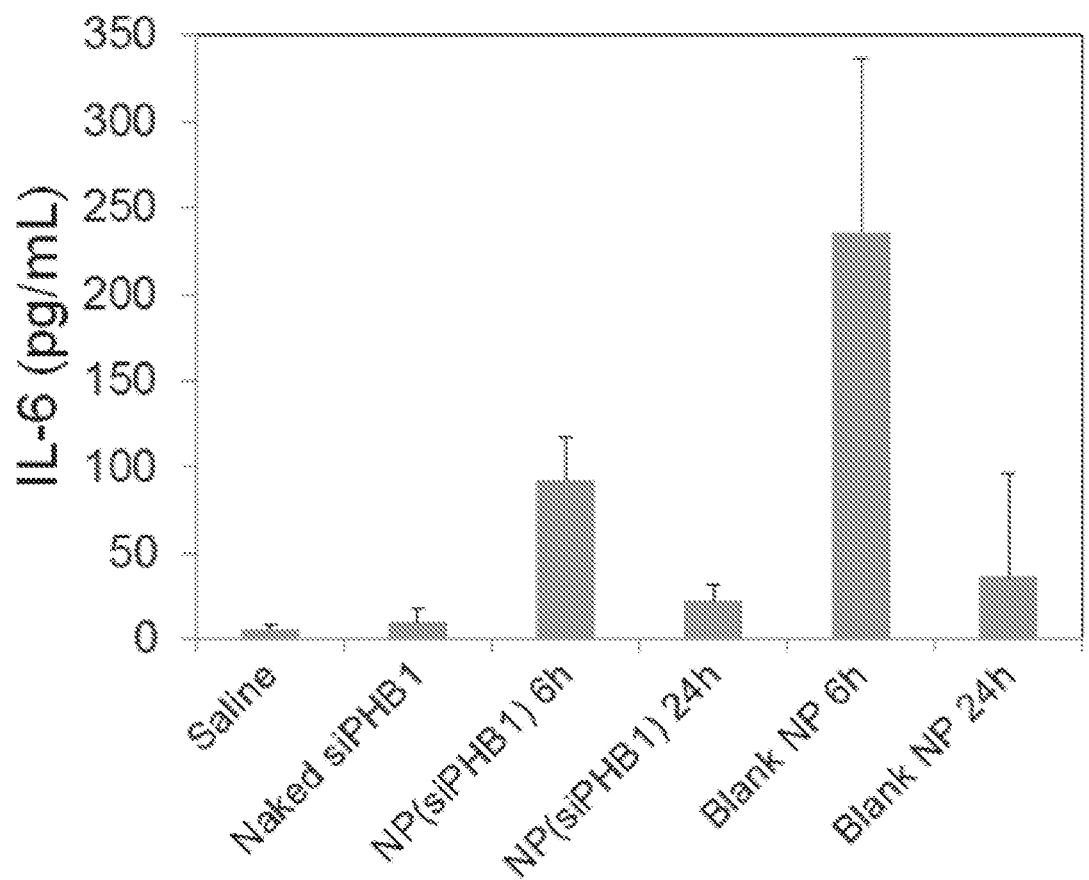
Figure 25C:
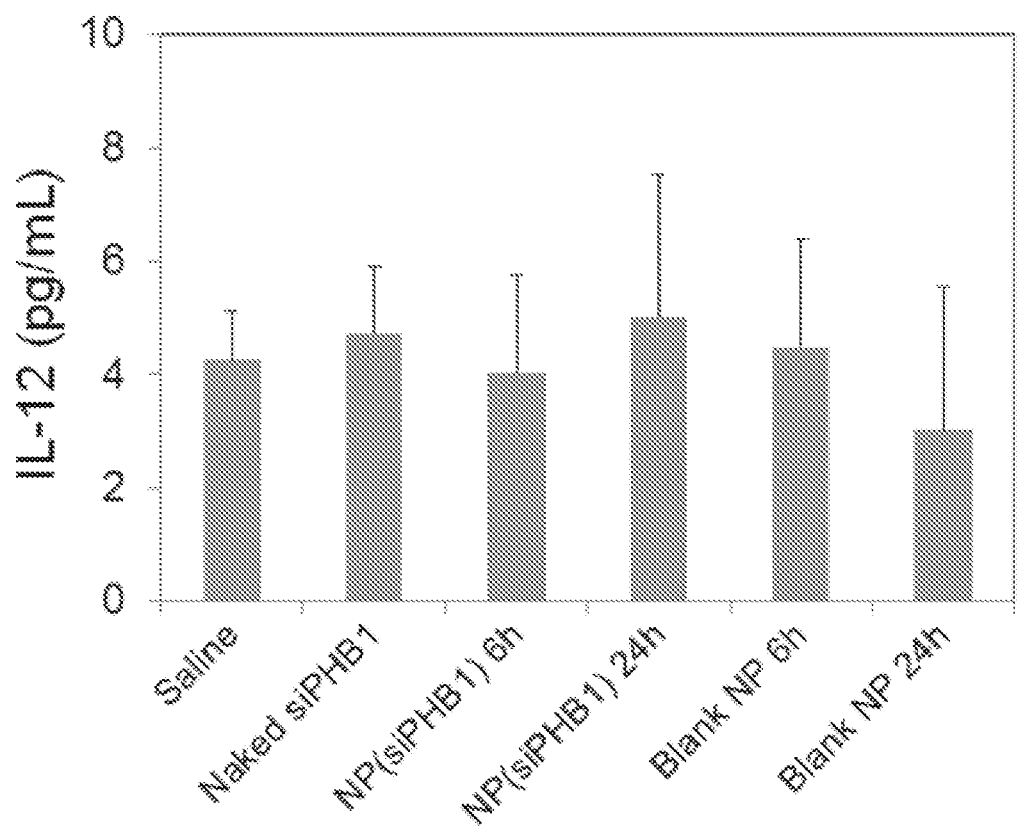

FIG. 25 shows immune response after NP treatment. Serum levels of (A) TNF-α, (B) IL-6, and (C) IL-12 at 6 and 24 h after intravenous injection of NP(siPHB1), blank NP, or naked siPHB1 (600 µg siRNA/kg). BALB/c immunocompetent mice were used for this study. Serum samples obtained 6 h or 24 h after injections were processed for the measurement of TNF-α, IL-6, and IL-12 by ELISA (Abeam Biotech Co. and PBL Biomedical Laboratories) in accordance with the manufacturer's instructions. Data are presented as mean±S.D., (n=3).

FIG. 26 shows in vitro cytotoxicity of NP(siPHB1) in combination with free cisplatin. (A) NCI-H460 and (B) A549 cells were incubated with cisplatin at different concentrations for 72 h with or without NP(siPHB1) treatment (10 nM siRNA). Cell viability was measured by Alamar blue assay. Data are represented as mean±S.D. (n=3).

FIG. 27 shows the therapeutic efficacy of combinatorial treatment with NP(siPHB1) and free cisplatin in A549 xenograft. (A) Timeline for IV injection of NPs and IP injection of cisplatin. (B) Relative tumor volume change over the course of therapy. (C) Kaplan-Meier survival curve of A549 tumor-bearing mice over 64 days. (D) Representative mouse image for each group. Line (1) shows saline group; line (2) shows NP(siControl) group; line (3) shows NP(siControl)+cisplatin group; line (4) shows NP(siPHB1) group; line (5) shows NP(siPHB1)+cisplatin group.

Figure 28A:
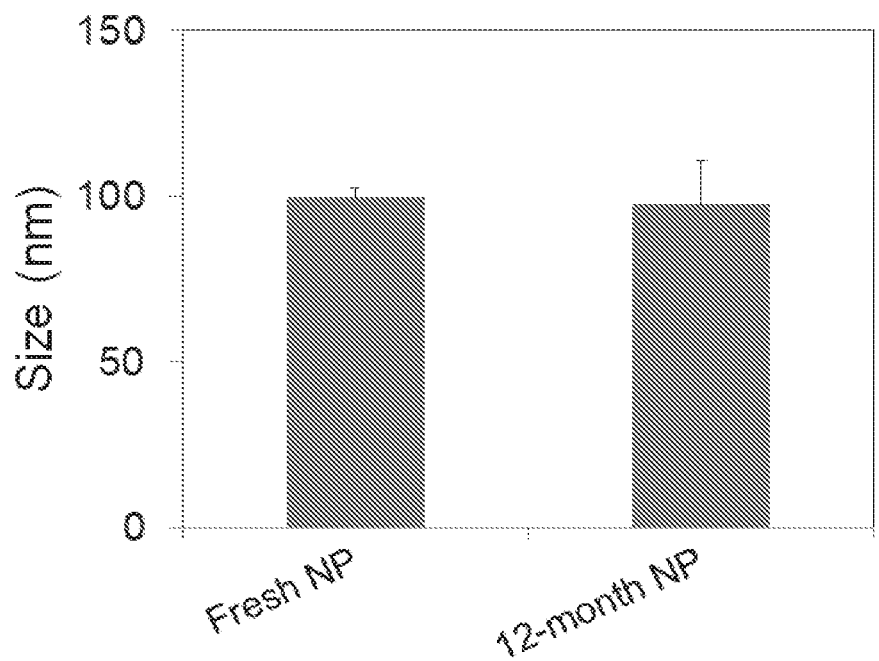
Figure 28B:
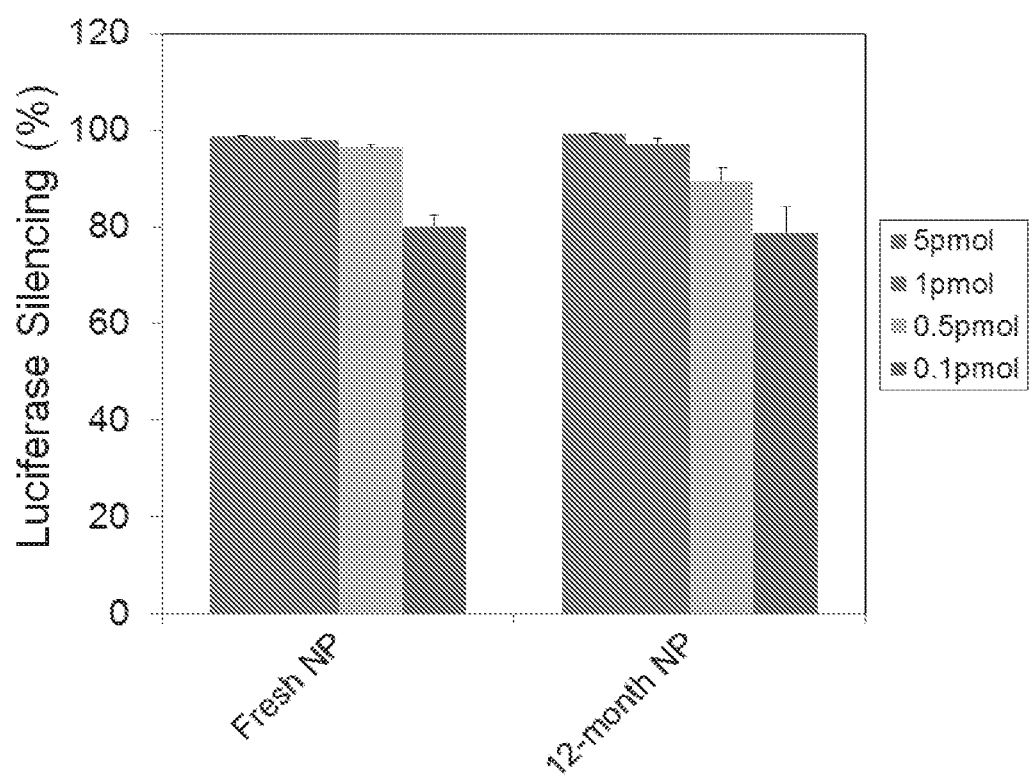

FIG. 28 shows the effect of NP storage at −80° C. on particle size and silencing efficacy. (A) Size of NPs before and after storage for 12 months. (B) Luciferase silencing in Luc-HeLa cells by NPs freshly prepared vs. stored at −80° C. for 12 months.

Figure 29:
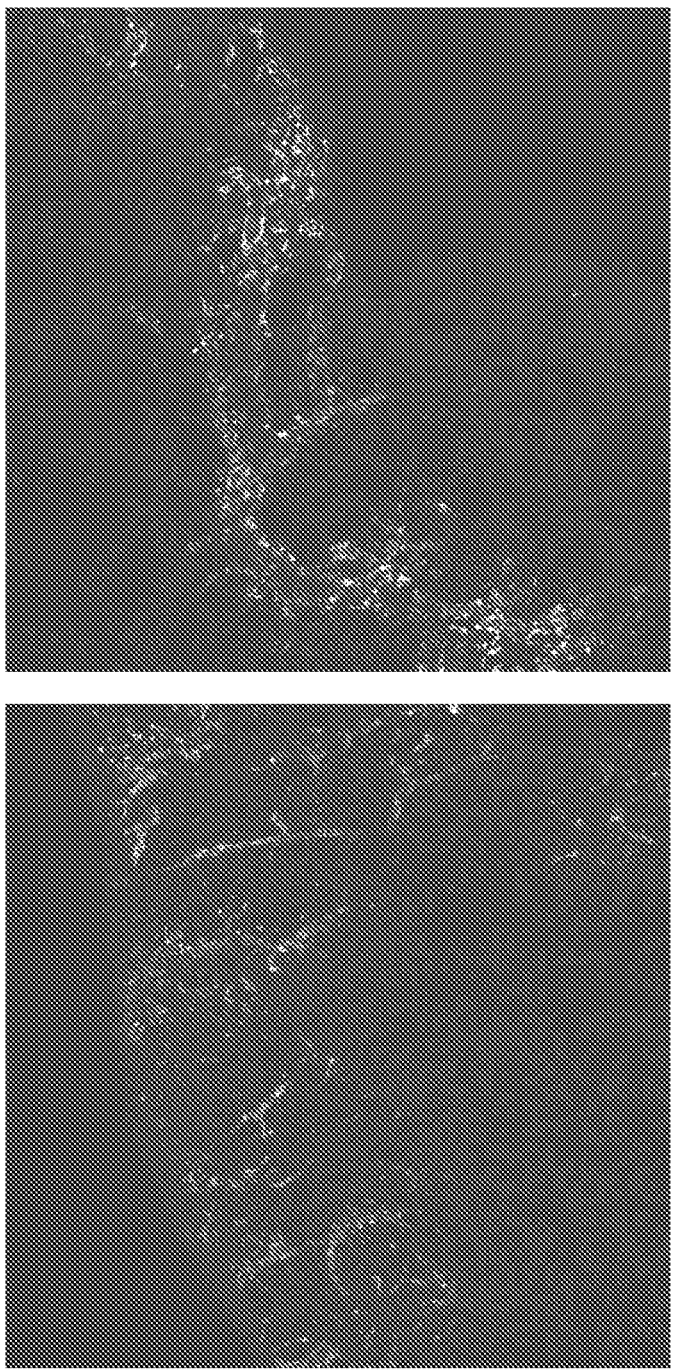

FIG. 29 shows NP siRNA delivery to venular endothelium.

Figure 30A:
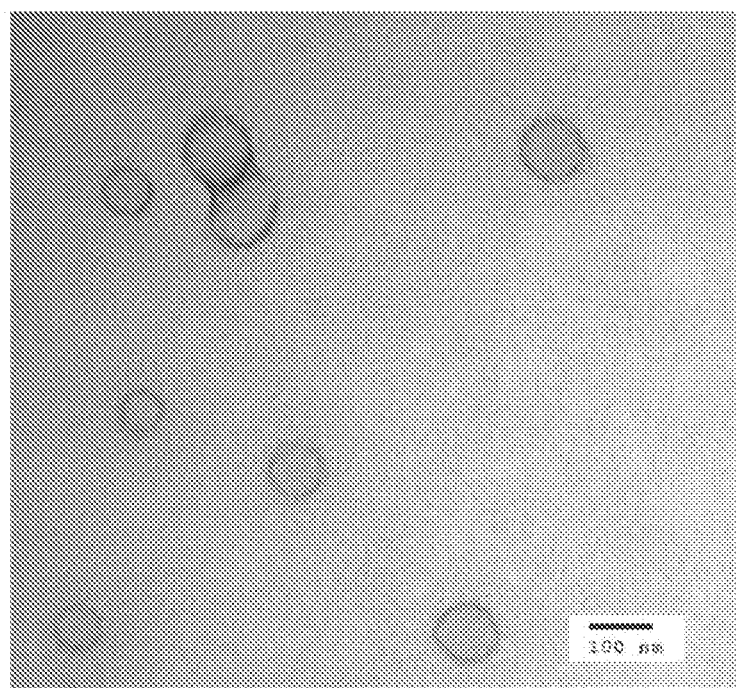
Figure 30B:
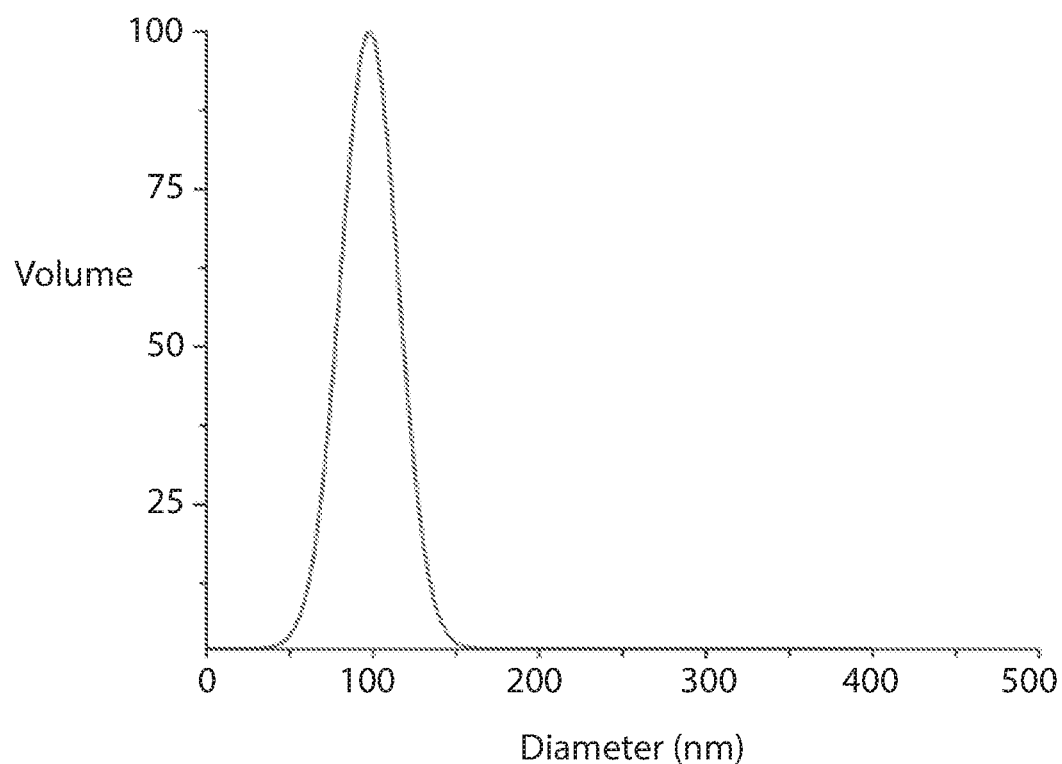
Figure 30C:
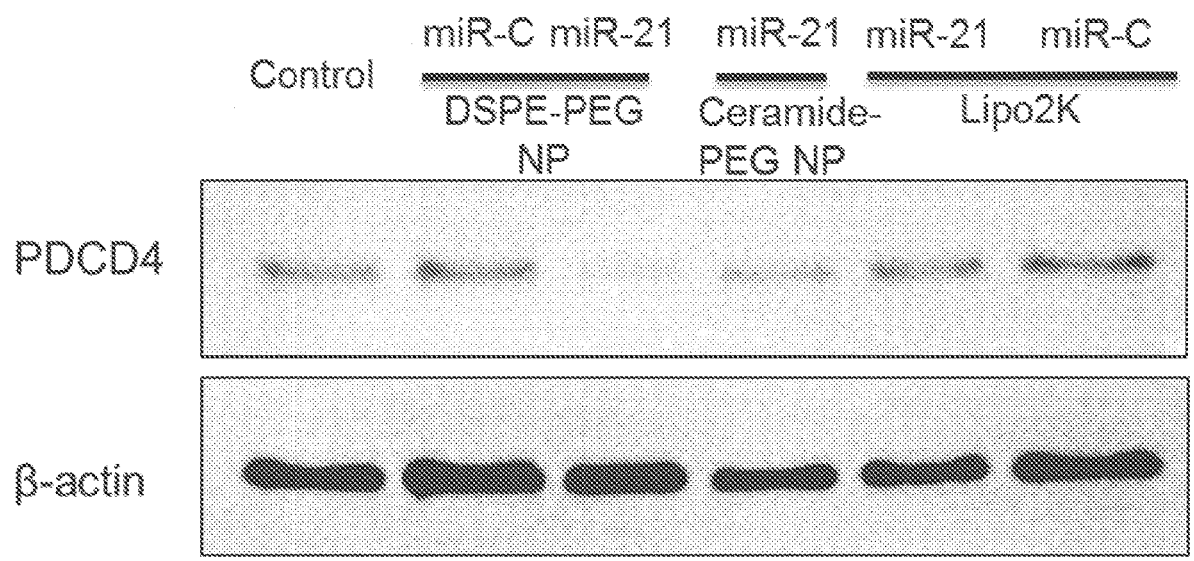

FIG. 30 shows microRNA delivery. The size of the microRNA (miR) NPs is demonstrated by (A) TEM and (B) DLS. (C) Western blot analysis of PDCD4 protein level in mouse RAW264.7 macrophage after transfected with NP(miR-21) or Lipo2K-miR-21 complexes.

Figure 31A:
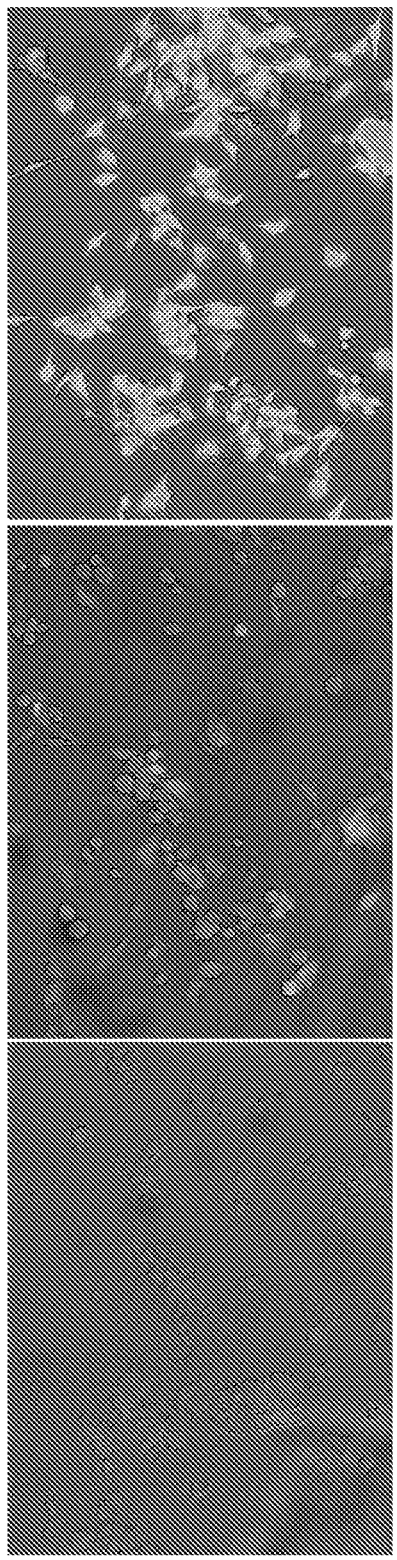
Figure 31B:
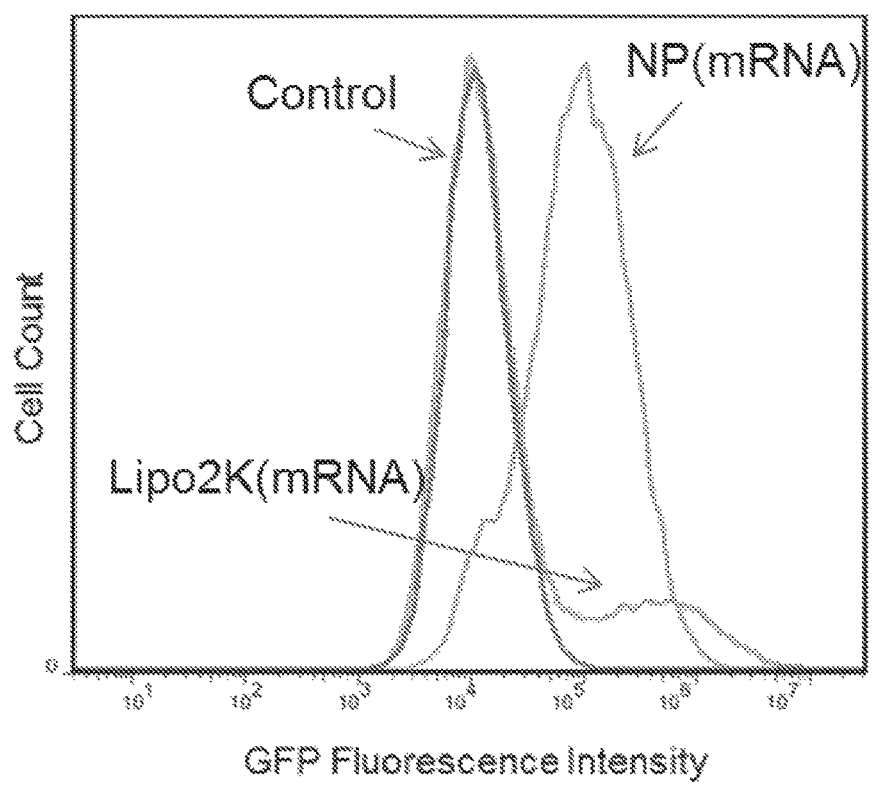
Figure 31C:
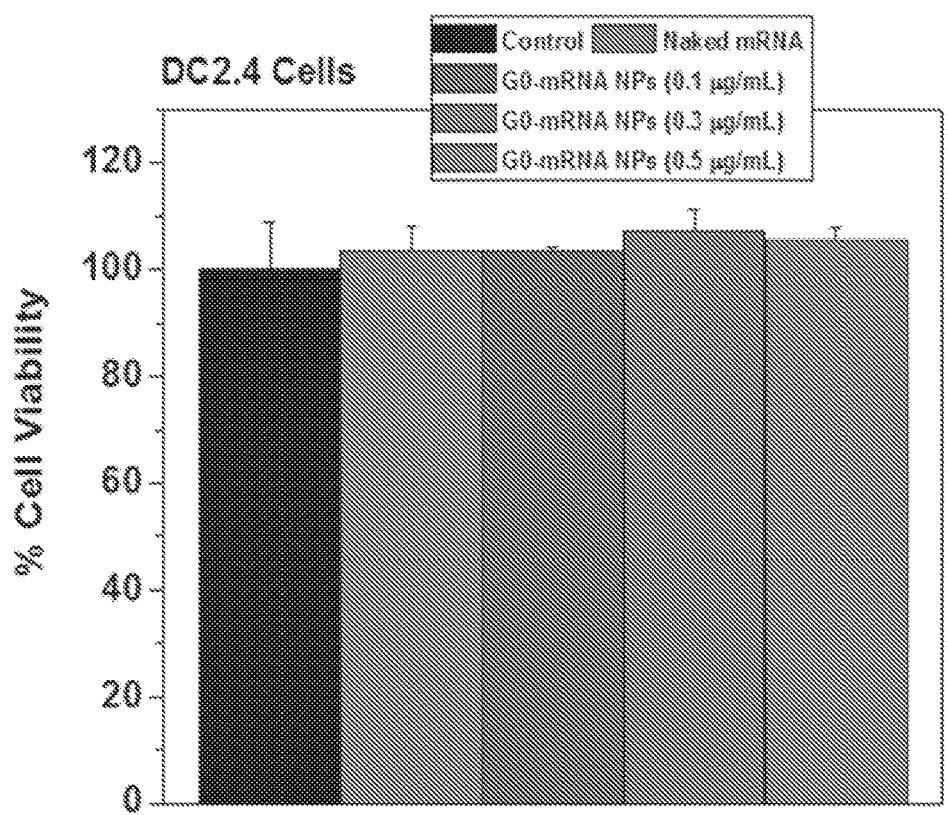

FIG. 31 shows mRNA delivery. FIG. 31A: The expression of eGFP on DC2.4 dendritic cells after incubation with eGFP mRNA NPs. DC2.4 cells were transfected with eGFP mRNA NPs at the concentration of 0.2 µg/mL for 24 h, then washed with PBS, and further incubated with cell culture medium. At 0, 1, and 3 days after transfection, images were acquired on inverted Fluorescence Microscope (Zeiss Axiovert 200) to examine eGFP expression. FIG. 31B: Flow cytometry quantification of the eGFP expression in DC2.4 cells cultured in 24-well plate with a density of 5×10$^4$ cells per well, were transfected with mRNA NPs at mRNA concentration of 0.5 µg/mL in complete culture media containing 10% FBS. Untreated cells and Lipo2K were used as controls. eGFP expression was determined using flow cytometry assay and at least 10,000 cells were tested for each sample. The mRNA NP treatment led to 86.7% eGFP positive cells, vs. Lipo2K with only 23.4%. FIG. 31C: Cytotoxicity of mRNA NPs in DC2.4 cells after 48 h of transfection. The assay was done in triplicates (n=3).

FIG. 32 shows protein delivery. (A) Effect of water-miscible solvent on NP size and encapsulation efficiency of BSA protein. (B) The enzymatic activity of encapsulated HRP protein in NPs vs. free HRP. The NPs were formulated by using DMSO as the solvent. (C) TEM image of FITC-BSA NPs prepared with DMSO. (D) Effect of protein encapsulation on NP size.

Figure 33A:
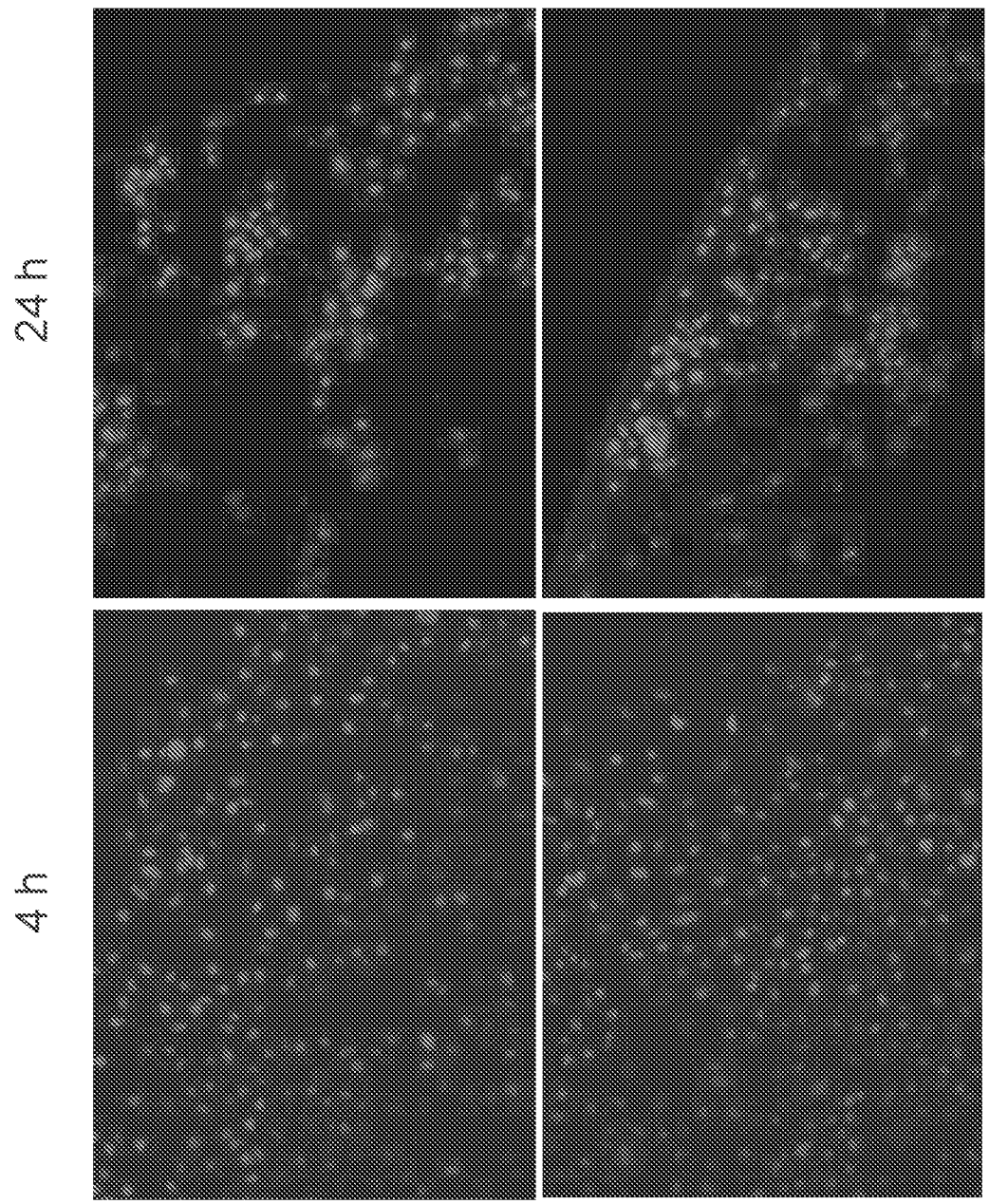
Figure 33B:
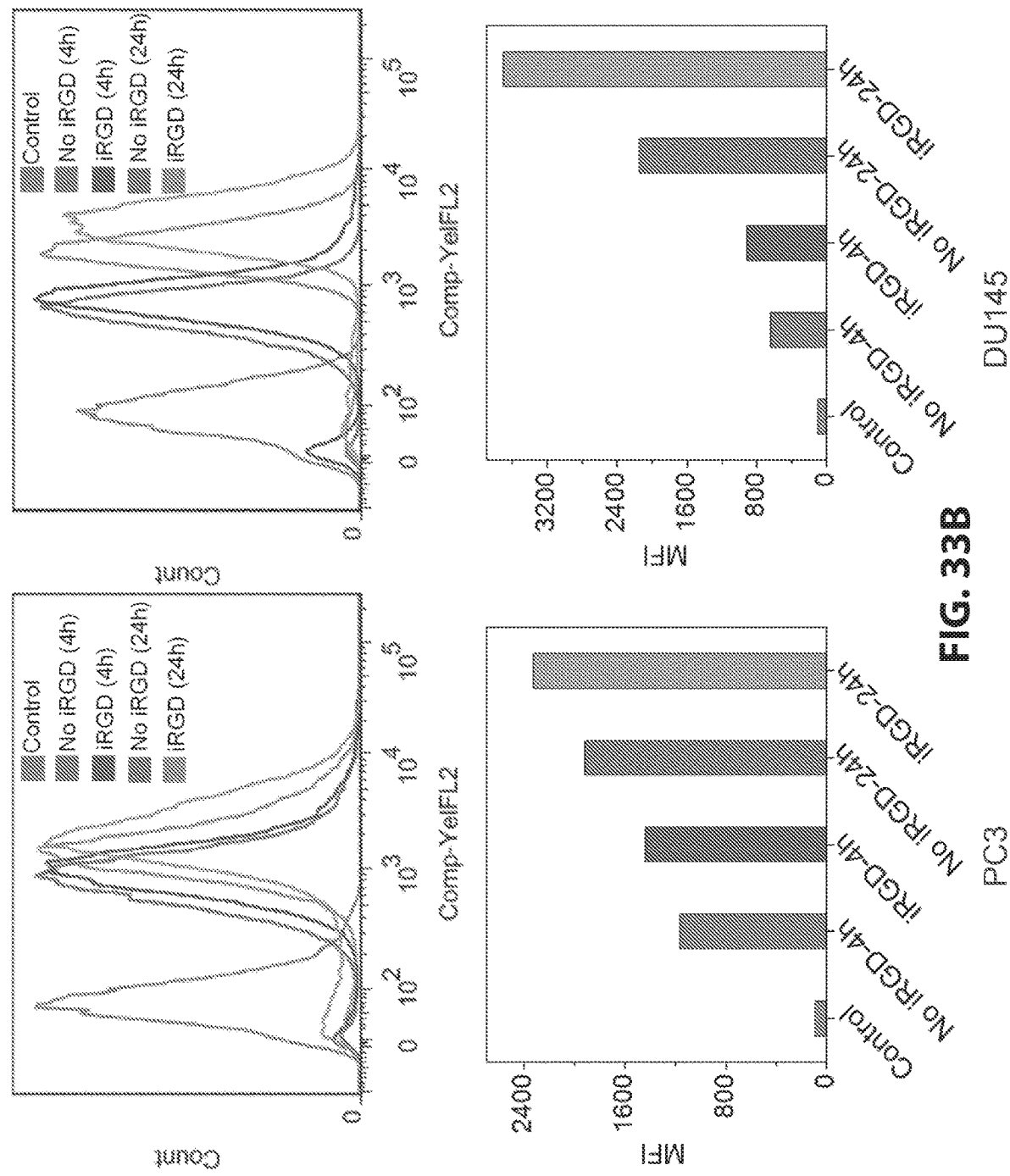

FIG. 33 shows targeted NP development for enhanced cellular uptake. (A) Fluorescence images of cellular uptake of iRGD-targeted siRNA NPs vs. non-targeted NPs in PC3 cells. (B) Flow cytometry of targeted vs. non-targeted NPs in PC3 (left) and DU145 (right) cells at 4 h and 24 h.

FIG. 34 shows theranostic NP development for simultaneous imaging and therapy. (A) The structure of two fluorescent polymers: F8BT {poly[(9,9-di-n-octylfluorenyl-2,7-diyl)-alt-(benzo[2,1,3]thiadiazol-4,8-diyl)]} and PCPDTBT {poly[2,6-(4,4-bis-(2-ethylhexyl)-4H-cyclopenta [2,1-b;3,4-b']dithiophene)-alt-4,7(2,1,3-benzothiadiazole)]}. (B) TEM of the F8BT polymer NPs loaded with G0/C14-siRNA complexes. The NP surface is coated with DSPE-PEG. (C) Fluorescence imaging of cellular uptake of F8BT NPs in HeLa cells at different time points. The F8BT polymer itself is fluorescent with green color. (D) Luciferase silencing and cytotoxicity of the F8BT siRNA NPs in Luc-HeLa cells. (E) Circulation profiles of PCPDTBT-siRNA NPs with different surface charges in BALB/c mice after intravenous injection. NP #1: −6.4 mV; NP #2: 5.24 mV; and NP #3: 18.92 mV.

Figure 35A:
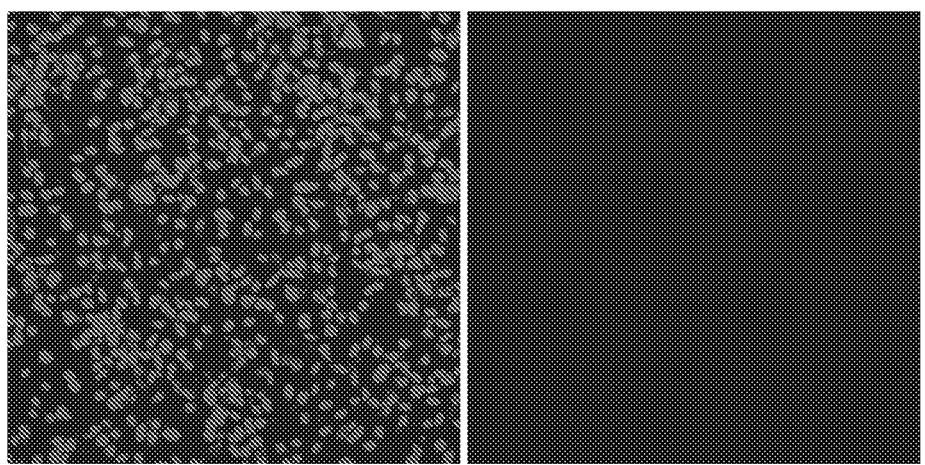
Figure 35B:
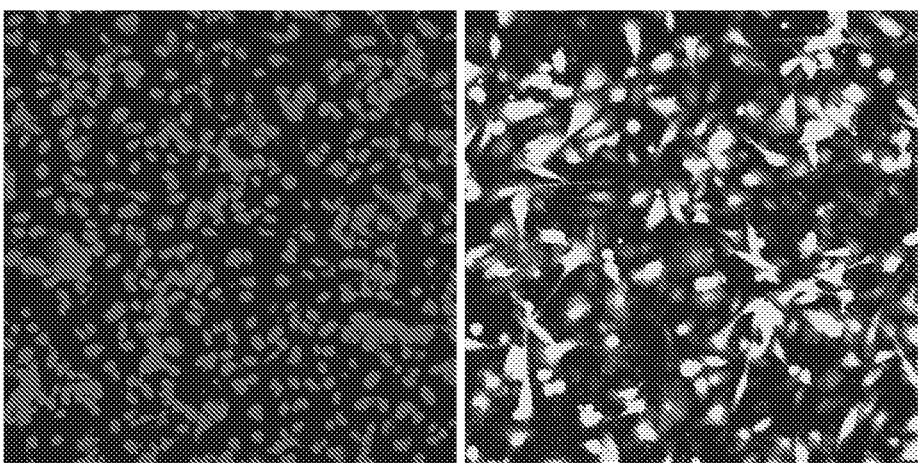
Figure 35C:
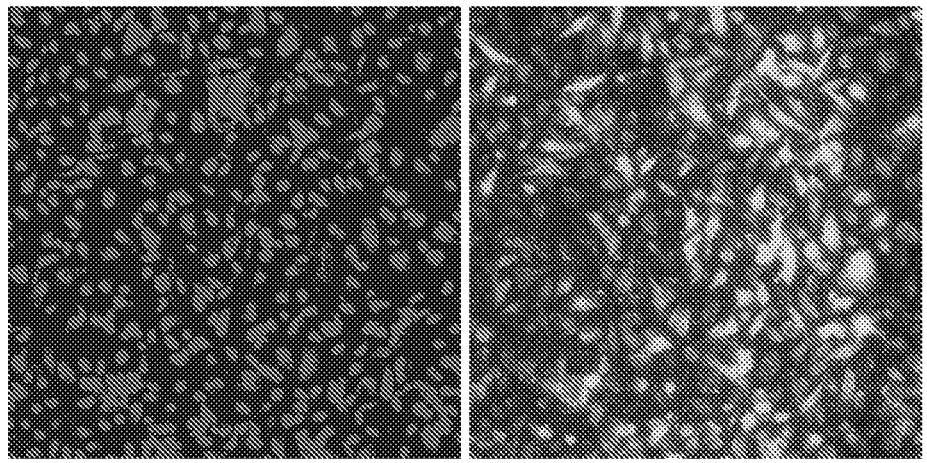
Figure 36A:
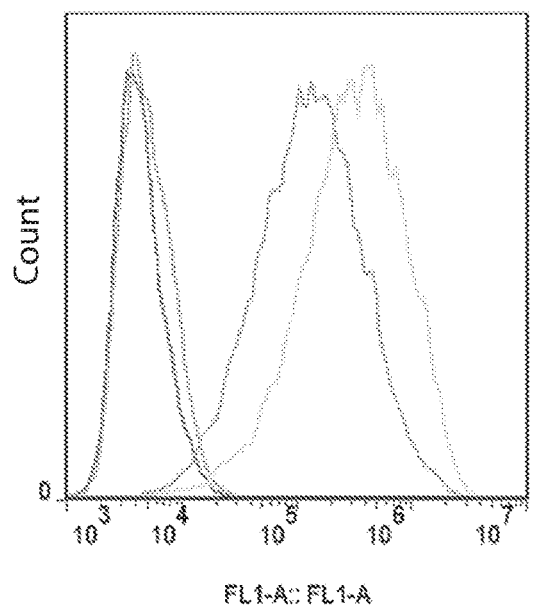
Figure 36C:
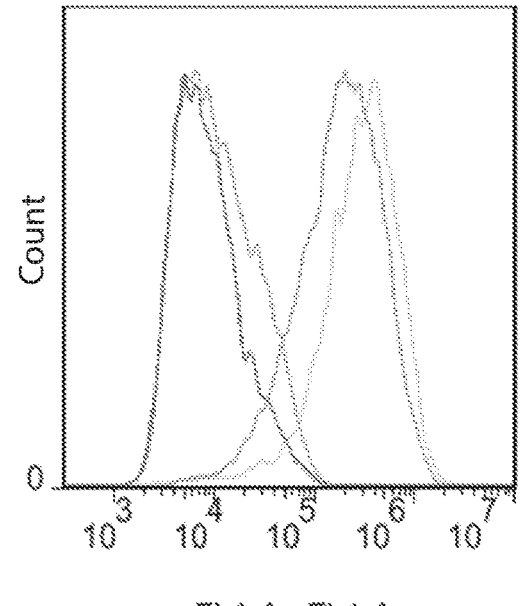
Figure 36B:
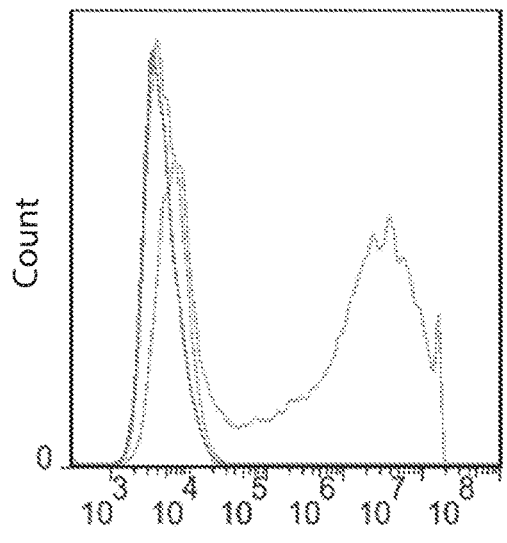
Figure 36D:
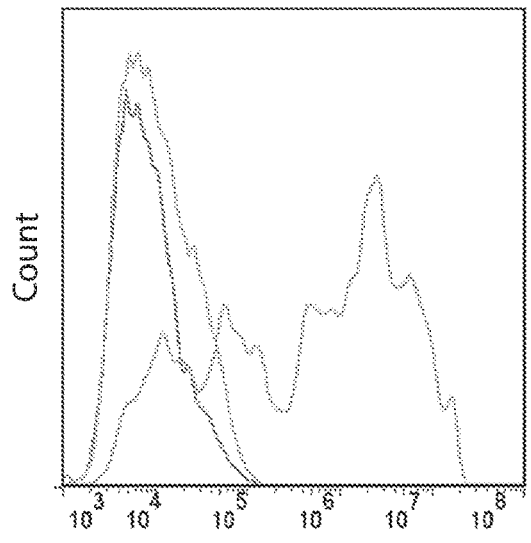

FIG. 35 contains fluorescence images of cellular uptake of mRNA in PC3 tumor cells incubated with (A) naked mRNA; (B) Lipo2K/mRNA complexes; and (C) mRNA-loaded NPs.

FIG. 36 contains plots showing the transfection efficiency of mRNA-loaded NPs vs. Lipo2K/mRNA complexes in PC3 cells (A, B) and DU145 (C, D) cells.

Figure 37A:
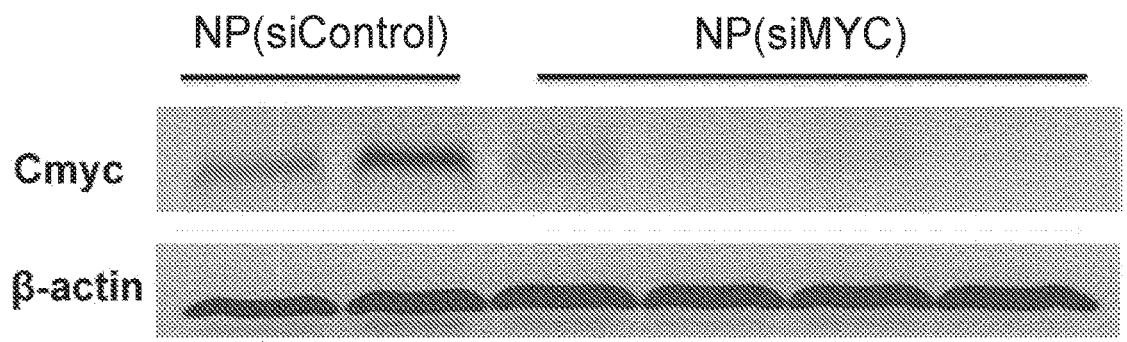
Figure 37B:
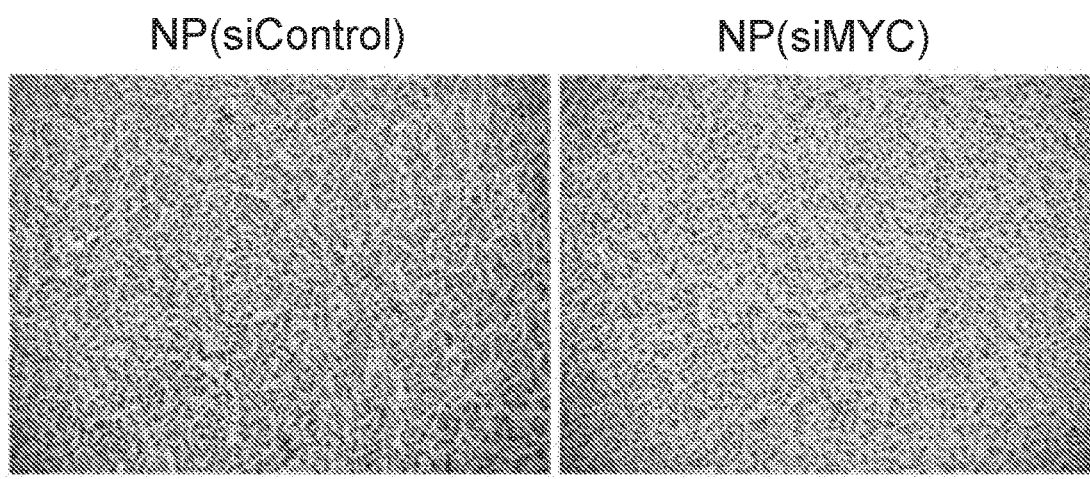
Figure 37C:
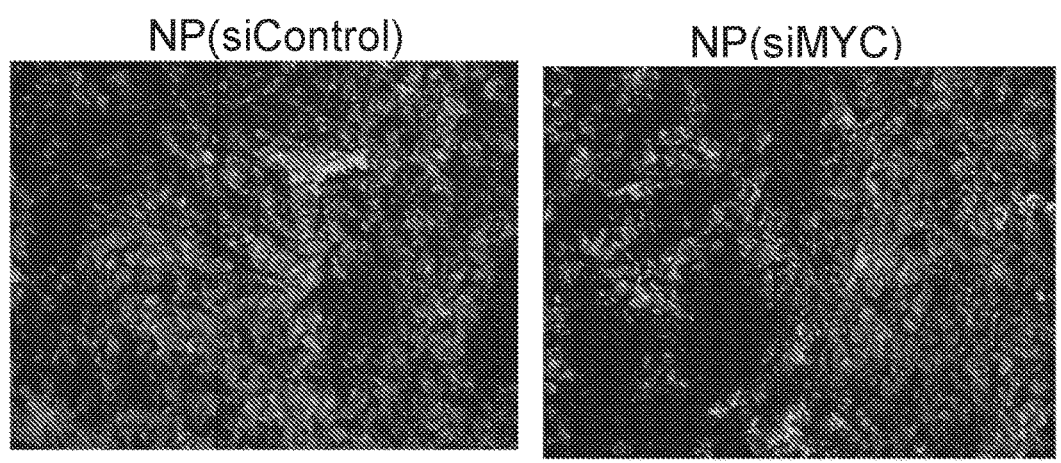

FIG. 37 contains images showing in vivo MYC silencing in a PC3 xenograft. MYC protein level in the tumor tissues was tested by (A) western blot analysis, (B) immunohistochemistry, and (C) immunofluorescence after treatment of NP(siControl) vs. NP(siMYC).

FIG. 38 contains plots and an image showing the therapeutic efficacy of NP(siMYC) in the PC3 Xenograft tumor model. (A) Plot of the injection timeline. NP(siMYC) was injected i.v. and cisplatin was injected i.p. (B, C) Plots showing inhibition of PC3 tumor growth after treatment with PBS, NP(siControl), NP(siControl)+cisplatin, NP(siMYC), and NP(siMYC)+cisplatin (n=7 per group). (D) Digital photograph of tumors for different groups obtained at the end of experiment. From left to right: PBS control, NP(siControl), NP(siControl)+cisplatin, NP(siMYC), and NP(siMYC)+cisplatin. (E) Plot of body weight of tumor-bearing mice over the course of therapy.

FIG. 39 are images showing time-dependent in vivo near IR imaging of tumor and lymph node mapping. (A) Time-dependent fluorescence imaging of BRAF$^{V600E}$ mutated 8505C tumor-bearing mouse after a single dose injection of NIR NPs; (B) NIR fluorescence of organs from BRAF$^{V600E}$ mutated 8505C tumor-bearing mouse at 24 h post injection of NIR NPs; (C) Quantitative biodistribution analysis from b; (D) NIR fluorescence imaging of lymph nodes at 24 h after intravenous injection of NIR NPs (1, a small piece of muscle; 2, 3 inguinal lymph nodes; 4-7: neck lymph nodes; 8, 9: lateral thoracic lymph nodes; and 10, 11: axillary lymph nodes); (E) Sentinel lymph node mapping 10 min after subcutaneous injection of NIR NPs into the forepaws.

FIG. 40 shows in vivo antitumor effect of NP(siBRAF) in BRAF$^{V600E}$ mutated 8505C xenograft tumor models. (A) Body weight Changes of the BRAF$^{V600E}$ mutated 8505C tumor-bearing mice that treated with saline, NP(siControl), and NP(siBRAF). (B) Tumor growth curve of PBS-, NP(si-Control)-, and NP(siBRAF)-treated BRAF$^{V600E}$ mutated 8505C tumor bearing mice. Three IV injections were indicated by the arrows. (C) Representative picture of tumors from b. (D) Western blot analysis of BRAF expression in BRAF$^{V600E}$ mutated 8505C tumor tissue after systemic treatment of NP(siControl) and NP(siBRAF). (E) Immunochemical microphotographs of BRAF expression in BRAF$^{V600E}$ mutated 8505C tumor tissue after systemic treatment of NP(siControl) or NP(siBRAF).

DETAILED DESCRIPTION

The current disclosure provides the preparation and use of particles comprising a water-insoluble polymeric core; a payload; and a first amphiphile within the core. In some embodiments, the particles further comprise a shell comprising a second amphiphile. In some embodiments, the payload and the first amphiphile have complementary electrical charges. The particles can be synthesized by precipitation methods in a simple manner, without requiring detergents or sonication. Further, the size and/or density of the particles produced by this method may result in an enhanced efficacy of docking and release of the payload from the particle. This platform combines the advantages of the favorable features (e.g., physicochemical, pharmacokinetic) of particles with a polymeric core and particles with a lipid core.

In the present description, it is appreciated that certain features described herein, which are, for clarity, described in the context of separate embodiments, can also be provided in combination in a single embodiment. Conversely, various features described herein which are, for brevity, described in the context of a single embodiment, can also be provided separately or in any suitable subcombination.

Although methods and materials similar or equivalent to those described herein can be used in the practice or testing of the present invention, suitable methods and materials are described below. In addition, the materials, methods and examples are illustrative only and not intended to be limiting.

Definitions

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

The term "alkyl" employed alone or in combination with other terms, refers to a saturated hydrocarbon group that may be straight-chain or branched. The term "C$_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "amide" or "amido" refers to a group of formula —C(=O)NH—.

The term "amino" refers to a group of formula —NH$_2$.

The term "amphipathic polymer" refers to a polymer having both a hydrophobic and a hydrophilic portion.

The term "amphiphile" refers to a molecule having both lipophilic and hydrophilic properties.

The term "carbonyl", employed alone or in combination with other terms, refers to a —C(=O)— group, which also may be written as C(O).

The term "carboxy" refers to a group of formula —C(=O)OH.

The term "nanoparticle" as used herein refers to a particle having a size from about 1 nm to about 1000 nm.

The term "particle" as used herein refers to a composition having a size from about 1 nm to about 1000 µm.

The term "particle size" as used herein refers to the median size in a distribution of particles. The median size is determined from the average linear dimension of individual particles, for example, the diameter of a spherical particle. Size may be determined by any number of methods in the art, including dynamic light scattering (DLS) and transmission electron microscopy (TEM) techniques.

References to a composition described and disclosed herein are considered to include the free acid, the free base, and all addition salts. The compositions may also form inner salts or zwitterions when a free carboxy and a basic amino group are present concurrently. The term "pharmaceutically acceptable salt" refers to salts which possess toxicity profiles within a range that affords utility in pharmaceutical applications. In general the useful properties of the compositions described herein do not depend on whether the composition is or is not in a salt form, so unless clearly indicated otherwise (such as specifying that the composition should be in "free base" or "free acid" form), reference in the specification to a composition should be understood as including salt forms of the composition, whether or not this is explicitly stated. Preparation and selection of suitable salt forms is described in Stahl et al., *Handbook of Pharmaceutical Salts: Properties, Selection, and Use*, Wiley-VCH 2002.

When in the solid state, the compositions described herein and salts thereof may occur in various forms and may, e.g., take the form of solvates, including hydrates. In general, the useful properties of the compositions described herein do not depend on whether the composition or salt thereof is or is in a particular solid state form, such as a polymorph or solvate, so unless clearly indicated otherwise reference in the specification to compositions and salts should be understood as encompassing any solid state form of the composition, whether or not this is explicitly stated.

Compositions provided herein can also include all isotopes of atoms occurring in the intermediates or final compositions. Isotopes include those atoms having the same atomic number but different mass numbers. For example, isotopes of hydrogen include tritium and deuterium.

Abbreviations

The following abbreviations may be used in the present disclosure.

ALT=alanine aminotransferase; AST=aspartate aminotransferase; BSA=bovine serum albumin; BUN=blood urine nitrogen; DLS=differential light scattering; DMSO=dimethylsulfoxide; DOTAP=1,2-dioleoyl-3-trimethylammonium-propane; dNTP=deoxynucleotide mixture; DSPE=1,2-distearoyl-sn-glycero-3-phosphoethanolamine; EDTA=ethylenediaminetetraacetic acid; EEA1=early endosome antigen 1; eGFP=enhanced green fluorescent protein; EIPA=5-(N-ethyl-N-isopropyl)amiloride; ELISA=enzyme-linked immunosorbent assay; F8BT=poly[(9,9-di-n-octyl-fluorenyl-2,7-diyl)-alt-(benzo[2,1,3]thiadiazol-4,8-diyl)]; FBS=fetal bovine serum; FITC-BSA=fluorescein isothiocyanate labelled bovine serum albumin; H&E=hematoxylin and eosin; HRP=horseradish peroxidase; IL=interleukin; i.p.=intraperitoneal; i.v.=intravenous; LAMP1=Lysosomal-associated membrane protein 1; LPS=lipopolysaccharide; mAb=monoclonal antibody; miR=miRNA, microRNA or micro ribonucleic acid; mRNA=messenger ribonucleic acid; MWCO=molecular weight cutoff; NP=nanoparticle; NSCLC=non-small cell lung cancer; PAMAM=poly (amidoamine); PARP=poly (adenosine diphosphate-ribose) polymerase; PCR=polymerase chain reaction; PBS=phosphate-buffered saline; PCPDTBT=poly[2,6-(4,4-bis-(2-ethylhexyl)-4H-cyclopenta [2,1-b;3,4-b']dithiophene)-alt-4,7(2,1,3-benzothiadiazole)]; PEG=poly(ethylene glycol); PEGxxK=poly(ethylene glycol) having a molecular weight of about xx,000 daltons; PEI=polyethylenimine; PHB1=Prohibitin1 protein; PLA=poly (lactic acid); PLGA=poly(lactic-co-glycolic acid); RNAi=ribonucleic acid interference; mRNA=messenger ribonucleic acid; shRNA=short hairpin ribonucleic acid; siRNA=small interfering ribonucleic acid, short interfering ribonucleic acid, or silencing ribonucleic acid; SDS-PAGE=sodium dodecyl sulfate polyacrylamide gel electrophoresis; SEM=standard error of the mean; TBST=Tris-buffered saline and Tween 20 buffer; TEM=transmission electron microscopy; TNF=tumor necrosis factor.

Particles

The present disclosure provides a particle comprising a water-insoluble polymeric core; a payload; and a first amphiphile within the core.

Also provided in the disclosure is a particle prepared by a process comprising obtaining a first solution comprising a water-insoluble polymer, a payload and a first amphiphile in a water-miscible solvent; and mixing the first solution with an aqueous second solution to form an aqueous composition comprising a particle comprising a water-insoluble polymeric core comprising the water-insoluble polymer; the payload; and the first amphiphile.

In some embodiments, the payload and the first amphiphile have complementary electrical charges. In some embodiments, the first amphiphile is cationic. In some embodiments, the first amphiphile is anionic.

The water-insoluble polymeric core can comprise a variety of materials. The water-insoluble polymer can comprise homopolymers (i.e., synthesized from hydrophobic monomers (e.g., styrene, methyl methacrylate, glycidyl methacrylate, DL-lactide, and the like)), random copolymers (i.e., synthesized from two or more monomers (e.g., styrene, methyl methacrylate, glycidyl methacrylate, DL-lactide, acrylic acid, methacrylic acid, 2-hydroxyethyl acrylate, and the like)), block polymers (i.e., synthesized from two or more monomers (e.g., styrene, methyl methacrylate, glycidyl methacrylate, DL-lactide, acrylic acid, methacrylic acid, 2-hydroxyethyl acrylate, and the like)), graft polymers (e.g., synthesized from artificial polymers (polyacrylic acid, polyglycidyl methacrylate, and the like) and/or natural polymers (e.g., dextran, starch, chitosan, and the like) with functional pendent groups (e.g., amino, carboxylate, hydroxyl, epoxy groups, and the like)), and/or branched polymers (e.g., a hyperbranched polyester with multifunctional alcohol building block and 2,2-bis(methylol)propionic acid branching units, such as Boltorn™ H40).

Non-limiting exemplary polymers that can be included in the polymeric core include polymer systems that are approved for use in humans, e.g., poly(glycolic acid), poly (lactic acid), poly(caprolactone), poly(lactide-co-glycolide), poly(ortho ester) II, poly(alkyl cyanoacrylate), desaminotyrosyl octyl ester, polyphosphoesters, polyester amides, polyurethanes, and lipids. Other non-limiting examples of polymers that the core can comprise include: chitosan; acrylates copolymer; acrylic acid-isooctyl acrylate copolymer; ammonio methacrylate copolymer; ammonio methacrylate copolymer type A; ammonio methacrylate copolymer type B; butyl ester of vinyl methyl ether/maleic anhydride copolymer (125,000 molecular weight); carbomer homopolymer type A (allyl pentaerythritol crosslinked); carbomer homopolymer type B (allyl sucrose crosslinked); cellulosic polymers; dimethylaminoethyl methacrylate-butyl methacrylate-methyl methacrylate copolymer; dimethylsiloxane/methylvinylsiloxane copolymer; divinylbenzene styrene copolymer; ethyl acrylate-methacrylic acid copolymer; ethyl acrylate and methyl methacrylate copolymer (2:1; 750,000 molecular weight); ethylene vinyl acetate copolymer; ethylene-propylene copolymer; ethylene-vinyl acetate copolymer (28% vinyl acetate); glycerin polymer solution i-137; glycerin polymer solution im-137; hydrogel polymer; ink/polyethylene terephthalate/aluminum/polyethylene/sodium polymethacrylate/ethylene vinyl acetate copolymer; isooctyl acrylate/acrylamide/vinyl acetate copolymer; Kollidon® VA 64 polymer; methacrylic acid-ethyl acrylate copolymer (1:1) type A; methacrylic acid-methyl methacrylate copolymer (1:1); methacrylic acid-methyl methacrylate copolymer (1:2); methacrylic acid copolymer; methacrylic acid copolymer type A; methacrylic acid copolymer type B; methacrylic acid copolymer type C; octadecene-1/maleic acid copolymer; PEG-22 methyl ether/dodecyl glycol copolymer; PEG-45/dodecyl glycol copolymer; Polyester polyamine copolymer; poly(ethylene glycol) 1,000; poly (ethylene glycol) 1,450; poly(ethylene glycol) 1,500; poly (ethylene glycol) 1,540; poly(ethylene glycol) 200; poly (ethylene glycol) 20,000; poly(ethylene glycol) 200,000; poly(ethylene glycol) 2,000,000; poly(ethylene glycol) 300; poly(ethylene glycol) 300-1,600; poly(ethylene glycol) 300-1,600; poly(ethylene glycol) 3,350; poly(ethylene glycol) 3,500; poly(ethylene glycol) 400; poly(ethylene glycol) 4,000; poly(ethylene glycol) 4,500; poly(ethylene glycol) 540; poly(ethylene glycol) 600; poly(ethylene glycol) 6,000; poly(ethylene glycol) 7,000; poly(ethylene glycol) 7,000,000; poly(ethylene glycol) 800; poly(ethylene glycol) 8,000; poly(ethylene glycol) 900; polyvinyl chloride-polyvinyl acetate copolymer; povidone acrylate copolymer; povidone/eicosene copolymer; polyoxy(methyl-1,2-ethanediyl), alpha-hydro-omega-hydroxy-, polymer with 1,1'-methylenebis[4-isocyanatocyclohexane] copolymer; polyvinyl methyl ether/maleic acid copolymer; styrene/isoprene/styrene block copolymer; vinyl acetate-crotonic acid copolymer; {poly[(9,9-di-n-octylfluorenyl-2,7-diyl)-alt-(benzo[2,1,3]thiadiazol-4,8-diyl)]}, and {poly[2,6-(4,4-bis-(2-ethylhexyl)-4H-cyclopenta [2,1-b;3,4-b']dithiophene)-alt-4,7(2,1,3-benzothiadiazole)]}.

In some embodiments, the water-insoluble core comprises a hydrophobic polymer. Non-limiting examples of hydrophobic polymers include, but are not limited to: polylactic acid (PLA), polypropylene oxide, poly(lactide-co-glycolide) (PLGA), poly(epsilon-caprolactone), poly(ethylethylene), polybutadiene, polyglycolide, polymethylacrylate, polyvinylbutylether, polystyrene, polycyclopentadienylmethylnorbornene, polyethylenepropylene, polyethylethylene, polyisobutylene, polysiloxane, a polymer of any of the following: methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole), aminoalkyls (e.g., aminoalkylacrylates, aminoalkylsmethacrylates, aminoalkyl (meth)acrylamides), styrenes, and lactic acids.

In some embodiments, the water-insoluble core comprises an amphipathic polymer. Amphipathic polymers contain a molecular structure containing one or more repeating units (monomers) connected by covalent bonds and the overall structure includes both hydrophilic (polar) and lipophilic (apolar) properties, e.g., at opposite ends of the molecule. In some embodiments, the amphipathic polymers are copolymers containing a first hydrophilic polymer and a first hydrophobic polymer. Several methods are known in the art for identifying an amphipathic polymer. For example, an amphipathic polymer (e.g., an amphipathic copolymer) can be identified by its ability to form micelles in an aqueous solvent and/or Langmuir Blodgett films.

In some embodiments, the amphipathic polymer (e.g., an amphipathic copolymer) contains a polymer selected from the group of: polyethylene glycol (PEG), polyethylene oxide, polyethyleneimine, diethyleneglycol, triethyleneglycol, polyalkylene glycol, polyalkyline oxide, polyvinyl alcohol, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacryl-amide, polyhydroxypropylmethacrylate, polyhydroxyethylacrylate, hydroxymethylcellulose, hydroxyethylcellulose, polyglycerine, polyaspartamide, polyoxyethlene-polyoxypropylene copolymer (poloxamer), a polymer of any of lecithin or carboxylic acids (e.g., acrylic acid, methacrylic acid, itaconic acid, and maleic acid), polyoxyethylenes, polyethyleneoxide, and unsaturated ethylenic monocarboxylic acids. In some embodiments, the amphipathic polymer contains a polymer selected from the group of: polylactic acid (PLA), polypropylene oxide, poly(lactide-co-glycolide) (PLGA), poly(epsilon-caprolactone), poly(ethylethylene), polybutadiene, polyglycolide, polymethylacrylate, polyvinylbutylether, polystyrene, polycyclopentadienylmethylnorbornene, polyethylenepropylene, polyethylethylene, polyisobutylene, polysiloxane, and a polymer of any of the following: methyl acrylate, ethyl acrylate, propyl acrylate, n-butyl acrylate, isobutyl acrylate, 2-ethyl acrylate, t-butyl acrylate, methacrylates (e.g., ethyl methacrylate, n-butyl methacrylate, and isobutyl methacrylate), acrylonitriles, methacrylonitrile, vinyls (e.g., vinyl acetate, vinylversatate, vinylpropionate, vinylformamide, vinylacetamide, vinylpyridines, and vinyllimidazole), aminoalkyls (e.g., aminoalkylacrylates, aminoalkylsmethacrylates, and aminoalkyl(meth)acrylamides), styrenes, and lactic acids.

In some embodiments, the amphipathic polymer contains poly(ethylene glycol)-co-poly(D,L-lactic acid) (PLA-PEG), poly(ethylene glycol)-co-(poly(lactide-co-glycolide)) (PLGA-PEG) (e.g., the amphipathic polymer is PLGA-PEG), polystyrene-b-polyethylene oxide, polybutylacrylate-b-polyacrylic acid, or polybutylmethacrylate-b-polyethyleneoxide. Additional examples of amphipathic copolymers are described in U.S. Patent Application Publication No. 2004/0091546 (incorporated herein by reference in its entirety). Additional examples of amphipathic polymers (e.g., amphipathic copolymers) are known in the art.

In some embodiments, the water-insoluble core comprises a polymer comprising an aliphatic polyester polymer, e.g., polycaprolactone (PCL), polybutylene succinate (PBS), or a polyhydroxylalkanoate (PHA), such as polyhydroxybutyrate. Other examples include polylactic acid (PLA) and polyglycolic acid (PGA). In some embodiments, the aliphatic polyester polymer is selected from polylactic acids, polyglycolic acids, and copolymers of lactic acid and glycolic acid (PLGA). A copolymer of lactic acid and glycolic acid can comprise a range of ratios of lactic acid to glycolic acid monomers, for example, from about 1:9 to about 9:1, from about 1:4 to about 4:1, from about 3:7 to about 7:3, or from about 3:2 to about 2:3. In some embodiments, the ratio of lactic acid to glycolic acid monomers can be about 1:9; about 1:8; about 1:7; about 1:6; about 1:5; about 1:4; about 3:7; about 2:3; about 1:1; about 3:2; about 7:3; about 4:1; about 5:1; about 6:1; about 7:1; about 8:1; or about 9:1.

In some embodiments, the water-insoluble core comprises a fluorescent polymer. The fluorescent polymer can be one or more polymers selected from polyphenylenevinylenes (e.g., poly[(2-methoxy-5-(2-ethylhexyloxy)-1,4-phenylene-vinylene)-co-(4,4'-biphenylene-vinylene)]), polyfluorenes (e.g., poly(fluorene-co-phenylene) (PFP), poly(9,9-dioctyl-fluorenyl-2,7-diyl); copolymers such as poly[{9,9-dioctyl-2,7-divinylene-fluorenylene}-alt-co-{2-methoxy-5-(2-ethylhexyloxy)-1,4-phenylene}]), polythiophenes (e.g., poly(3-butylthiophene-2,5-diyl), poly(3-decyl-thiophene-2,5-diyl), poly[3-(2-ethyl-isocyanato-octadecanyl)thiophene], poly(3, 3'''-didodecyl quarter thiophene), copolymers such as poly [(9,9-dihexylfluorenyl-2,7-diyl)-alt-co-(bithiophene)] and poly[(9,9-dioctylfluorenyl-2,7-diyl)-alt-co-(bithiophene)]), poly(p-phenyleneethylene)s (PPE), polydiacetylenes (PDA), and their derivatives. Additional non-limiting examples of fluorescent polymers include F8BT {poly[(9, 9-di-n-octylfluorenyl-2,7-diyl)-alt-(benzo[2,1,3]thiadiazol-4,8-diyl)]} and PCPDTBT {poly[2,6-(4,4-bis-(2-ethylhexyl)-4H-cyclopenta [2,1-b;3,4-b']dithiophene)-alt-4,7(2, 1,3-benzothiadiazole)]}.

In some embodiments, the water-insoluble polymeric core consists essentially of, or consists of, one or more polymers described herein.

The first and second amphiphiles are molecules having both lipophilic and hydrophilic properties in the same molecule. An amphiphile can therefore comprise a segment that is hydrophobic and a segment that is hydrophilic.

A hydrophobic segment of an amphiphile can comprise, e.g., a hydrocarbon or a hydrocarbon that is substituted exclusively or predominantly with hydrophobic substituents such as halogen atoms. Typically, the hydrophobic segment can comprise a chain of 10, or more (e.g., 10, 11, 12, 13, 14, 15, 16, 17, 18, 19, 20 or more) carbon atoms. In some embodiments, the hydrophobic segment comprises an aliphatic chain, which in some embodiments can be branched and in some embodiments can be unbranched. In some embodiments, the hydrophobic segment comprises an aliphatic chain that is saturated. In some embodiments, the hydrophobic segment comprises an aliphatic chain that is unsaturated.

A hydrophilic segment of an amphiphile can comprise, e.g., one or more polar groups such as hydroxyl or ether groups. A hydrophilic segment of an amphiphile can comprise, e.g., one or more charged groups. A charged group can include a cation, e.g., ammonium or phosphonium groups. A charged group can include an anion, e.g., phosphate or sulfate groups.

A first amphiphile within the core comprises a hydrophilic region and a hydrophobic region, and can comprise a variety of materials. In some embodiments, the first amphiphile is negatively charged. In some embodiments, the first amphiphile is positively charged. In some embodiments, the first amphiphile comprises a phospholipid. In some embodiments, the first amphiphile comprises a dendrimer. Dendrimers (also known as dendrons, arborols or cascade molecules) are repetitively branched molecules which can be classified by generation, which refers to the number of repeated branching cycles performed during synthesis. For example, poly(amidoamine) (PAMAM) is ethylenediamine reacted with methyl acrylate, and then another ethylenediamine to make a generation 0 (G-0) PAMAM.

In some embodiments, the first amphiphile comprises one or more selected from the group consisting of: lecithin, an amino dendrimer (e.g., ethylenediamine core-poly (amidoamine) (PAMAM) generation 0 dendrimer (G0), ethylenediamine branched polyethylenimine ($M_w$~800) (PEI), polypropylenimine tetramine dendrimer, generation 1 (DAB), and derivatives thereof, e.g., amino derivatives formed by reacting an amine group with an alkyl epoxide, e.g., G0-C14 dendrimer described in Xu, X. et al. *Proc. Natl. Acad. Sci. U.S.A.* 2013; 110:18638-43, which is hereby incorporated by reference in its entirety), a PEG-phospholipid (e.g., 14:0 PEG350 PE (1,2-dimyristoyl-sn-glycero-3-phosphoethanolamine-N-[methoxy(polyethylene glycol)-350]), 14:0 PEG350 PE (1,2-dipalmitoyl-sn-glycero-3-phosphoethanolamine-N-[methoxy(polyethylene glycol)-350]), 18:0 PEG350 PE (1,2-distearoyl-sn-glycero-3-phosphoethanolamine-N-[methoxy(polyethylene glycol)-350]), 18:1 PEG350 PE (1,2-dioleoyl-sn-glycero-3-phosphoethanolamine-N-[methoxy(polyethylene glycol)-350]), 14:0 PEG550 PE (1,2-dimyristoyl-sn-glycero-3-phosphoethanolamine-N-[methoxy(polyethylene glycol)-550]), 14:0 PEG550 PE (1,2-dipalmitoyl-sn-glycero-3-phosphoethanolamine-N-[methoxy(polyethylene glycol)-550]), 18:0 PEG550 PE (1,2-distearoyl-sn-glycero-3-phosphoethanolamine-N-[methoxy(polyethylene glycol)-550]), 18:1 PEG550 PE (1,2-dioleoyl-sn-glycero-3-phosphoethanolamine-N-[methoxy(polyethylene glycol)-550]), 14:0 PEG750 PE (1,2-dimyristoyl-sn-glycero-3-phosphoethanolamine-N-[methoxy(polyethylene glycol)-750]), 14:0 PEG750 PE (1,2-dipalmitoyl-sn-glycero-3-phosphoethanolamine-N-[methoxy(polyethylene glycol)-750]), 18:0 PEG750 PE (1,2-distearoyl-sn-glycero-3-phosphoethanolamine-N-[methoxy(polyethylene glycol)-750]), 18:1 PEG750 PE (1,2-dioleoyl-sn-glycero-3-phosphoethanolamine-N-[methoxy(polyethylene glycol)-750]), 14:0 PEG1000 PE (1,2-dimyristoyl-sn-glycero-3-phosphoethanolamine-N-[methoxy(polyethylene glycol)-1000]), 14:0 PEG1000 PE (1,2-dipalmitoyl-sn-glycero-3-phosphoethanolamine-N-[methoxy(polyethylene glycol)-1000]), 18:0 PEG1000 PE (1,2-distearoyl-sn-glycero-3-phosphoethanolamine-N-[methoxy(polyethylene glycol)-1000]) (DSPE-PEG1K), 18:1 PEG1000 PE (1,2-dioleoyl-sn-glycero-3-phosphoethanolamine-N-[methoxy(polyethylene glycol)-1000]), 14:0 PEG2000 PE (1,2-dimyristoyl-sn-glycero-3-phosphoethanolamine-N-[methoxy(polyethylene glycol)-2000]), 14:0 PEG2000 PE (1,2-dipalmitoyl-sn-glycero-3-phosphoethanolamine-N-[methoxy(polyethylene glycol)-2000]), 18:0 PEG2000 PE (1,2-distearoyl-sn-glycero-3-phosphoethanolamine-N-[methoxy(polyethylene glycol)-2000]) (DSPE-PEG2K), 18:1 PEG2000 PE (1,2-dioleoyl-sn-glycero-3-phosphoethanolamine-N-[methoxy (polyethylene glycol)-2000]), 14:0 PEG3000 PE (1,2-dimyristoyl-sn-glycero-3-phosphoethanolamine-N-[methoxy(polyethylene glycol)-3000]), 14:0 PEG3000 PE (1,2-dipalmitoyl-sn-glycero-3-phosphoethanolamine-N-[methoxy(polyethylene glycol)-3000]), 18:0 PEG3000 PE (1,2-distearoyl-sn-glycero-3-phosphoethanolamine-N-[methoxy(polyethylene glycol)-3000]) (DSPE-PEG3K), 18:1 PEG3000 PE (1,2-dioleoyl-sn-glycero-3-phosphoethanolamine-N-[methoxy(polyethylene glycol)-3000]), 14:0 PEG5000 PE (1,2-dimyristoyl-sn-glycero-3-phosphoethanolamine-N-[methoxy(polyethylene glycol)-5000]), 14:0 PEG5000 PE (1,2-dipalmitoyl-sn-glycero-3-phosphoethanolamine-N-[methoxy(polyethylene glycol)-5000]), 18:0 PEG5000 PE (1,2-distearoyl-sn-glycero-3-phosphoethanolamine-N-[methoxy(polyethylene glycol)-5000]) (DSPE-PEG5K), 18:1 PEG5000 PE (1,2-dioleoyl-sn-glycero-3-phosphoethanolamine-N-[methoxy(polyethylene glycol)-5000])), a PEG-ceramide (e.g., C8 PEG750 ceramide (N-octanoyl-sphingosine-1-{succinyl[methoxy(polyethylene glycol)750]}), C16 PEG750 ceramide (N-palmitoyl-sphingosine-1-{succinyl[methoxy(polyethylene glycol)750]}), C8 PEG2000 ceramide (N-octanoyl-sphingosine-1-{succinyl[methoxy(polyethylene glycol)2000]}), C16 PEG2000 ceramide (N-palmitoyl-sphingosine-1-{succinyl[methoxy(polyethylene glycol)2000]}), C8 PEG5000 ceramide (N-octanoyl-sphingosine-1-{succinyl[methoxy(polyethylene glycol)5000]}), C16 PEG5000 ceramide (N-palmitoyl-sphingosine-1-{succinyl[methoxy(polyethylene glycol)5000]}), an anionic lipid (e.g., 1,2-di-O-tetradecyl-sn-glycero-3-phospho-(1'-rac-glycerol), 1,2-dihexadecanoyl-sn-glycero-3-phospho-(1'-sn-glycerol)), and a cationic lipid (e.g., DC-cholesterol (3β-[N—(N',N'-dimethylaminoethane)-carbamoyl]cholesterol), 18:1 TAP (DOTAP) (1,2-dioleoyl-3-trimethylammonium-propane), 1-oleoyl-2-[6-[(7-nitro-2-1,3-benzoxadiazol-4-yl)amino] hexanoyl]-3-trimethylammonium propane, 14:0 TAP (1,2-dimyristoyl-3-trimethylammonium-propane), 16:0 TAP (1,2-dipalmitoyl-3-trimethylammonium-propane), 18:0 TAP (1,2-stearoyl-3-trimethylammonium-propane), DOTMA (1,2-di-O-octadecenyl-3-trimethylammonium propane), a phosphatidylcholine (e.g., 12:0 EPC (1,2-dilauroyl-sn-glycero-3-ethylphosphocholine), 14:0 EPC (1,2-dimyristoyl-sn-glycero-3-ethylphosphocholine), 14:1 EPC (1,2-dimyristoleoyl-sn-glycero-3-ethylphosphocholine), 16:0 EPC (1,2-dipalmitoyl-sn-glycero-3-ethylphosphocholine), 18:0 EPC (1,2-distearoyl-sn-glycero-3-ethylphosphocholine), 18:1 EPC (1,2-dioleoyl-sn-glycero-3-ethylphosphocholine), 16:0-18:1 EPC (1-palmitoyl-2-oleoyl-sn-glycero-3-ethylphosphocholine)). In some embodiments, the first amphiphile consists essentially of, or consists of, one or more materials described herein.

The proportion of the first amphiphile within the water-insoluble core in the particle depends on the characteristics of the first amphiphile, the properties of the remainder of the core, and the application. In some embodiments, the first amphiphile is in the core in an amount from about 1% by weight to about 50.0% by weight. The first amphiphile is in the core in an amount from about 1% by weight to about 45% by weight, from about 1% by weight to about 40% by weight, from about 1% by weight to about 35% by weight, from about 1% by weight to about 30% by weight, from about 1% by weight to about 25% by weight, from about 1% by weight to about 20% by weight, from about 1% by weight to about 15% by weight, from about 10% by weight to about 45% by weight, from about 10% by weight to about 40% by weight, from about 10% by weight to about 35% by weight, from about 10% by weight to about 30% by weight, from about 10% by weight to about 25% by weight, from about 10% by weight to about 20% by weight, from about 10% by weight to about 15% by weight, from about 1% by weight to about 10% by weight, and/or from about 1% by weight to about 5% by weight. For example, the first amphiphile can be present in about 2% by weight, about 5% by weight, about 10% by weight, about 15% by weight, about 20% by weight, about 25% by weight, about 30% by weight, about 35% by weight, about 40% by weight, about 45% by weight, or about 50% by weight.

In some embodiments, a core may comprise a second payload covalently attached to the core. In some embodiments, the second payload is a biomolecule. In some embodiments, the second payload is a small molecule. In a non-limiting example, the payloads in each of the interior of the core and on the core may be an siRNA and a targeting molecule, respectively. The targeting molecule can be, for example, one selected from antibodies, antibody fragments, aptamers, peptides, aptides, sugars, small molecules, or combinations thereof. The targeting molecule can be presented on the surface of the particles (e.g., as shown in FIG. 3D) for targeting drug delivery.

The particle can optionally be covered with a second amphiphile. In some embodiments, the second amphiphile can comprise a phospholipid and/or a poly(ethylene glycol). In some embodiments, the second amphiphile comprises one or more selected from the group consisting of: lecithin, a neutral lipid (e.g., a diacyl glycerol (e.g., 8:0 DG (1,2-dioctanoyl-sn-glycerol), 10:0 DG (1,2-didecanoyl-sn-glycerol)), a sphingolipid (e.g., D-erythro-sphingosine and D-glucosyl-β-1,1' N-octanoyl-D-erythro-sphingosine), a ceramide (e.g., N-butyroyl-D-erythro-sphingosine, N-octanoyl-D-erythro-sphingosine, N-stearoyl-D-erythro-sphingosine (C17 base))), a PEG-phospholipid (e.g., 14:0 PEG350 PE (1,2-dimyristoyl-sn-glycero-3-phosphoethanolamine-N-[methoxy(polyethylene glycol)-350]), 14:0 PEG350 PE (1,2-dipalmitoyl-sn-glycero-3-phosphoethanolamine-N-[methoxy(polyethylene glycol)-350]), 18:0 PEG350 PE (1,2-distearoyl-sn-glycero-3-phosphoethanolamine-N-[methoxy(polyethylene glycol)-350]), 18:1 PEG350 PE (1,2-dioleoyl-sn-glycero-3-phosphoethanolamine-N-[methoxy(polyethylene glycol)-350]), 14:0 PEG550 PE (1,2-dimyristoyl-sn-glycero-3-phosphoethanolamine-N-[methoxy(polyethylene glycol)-550]), 14:0 PEG550 PE (1,2-dipalmitoyl-sn-glycero-3-phosphoethanolamine-N-[methoxy(polyethylene glycol)-550]), 18:0 PEG550 PE (1,2-distearoyl-sn-glycero-3-phosphoethanolamine-N-[methoxy(polyethylene glycol)-550]), 18:1 PEG550 PE (1,2-dioleoyl-sn-glycero-3-phosphoethanolamine-N-[methoxy(polyethylene glycol)-550]), 14:0 PEG750 PE (1,2-dimyristoyl-sn-glycero-3-phosphoethanolamine-N-[methoxy(polyethylene glycol)-750]), 14:0 PEG750 PE (1,2-dipalmitoyl-sn-glycero-3-phosphoethanolamine-N-[methoxy(polyethylene glycol)-750]), 18:0 PEG750 PE (1,2-distearoyl-sn-glycero-3-phosphoethanolamine-N-[methoxy(polyethylene glycol)-750]), 18:1 PEG750 PE (1,2-dioleoyl-sn-glycero-3-phosphoethanolamine-N-[methoxy(polyethylene glycol)-750]), 14:0 PEG1000 PE (1,2-dimyristoyl-sn-glycero-3-phosphoethanolamine-N-[methoxy(polyethylene glycol)-1000]), 14:0 PEG1000 PE (1,2-dipalmitoyl-sn-glycero-3-phosphoethanolamine-N-[methoxy(polyethylene glycol)-1000]), 18:0 PEG1000 PE (1,2-distearoyl-sn-glycero-3-phosphoethanolamine-N-[methoxy(polyethylene glycol)-1000]) (DSPE-PEG1K), 18:1 PEG1000 PE (1,2-dioleoyl-sn-glycero-3-phosphoethanolamine-N-[methoxy(polyethylene glycol)-1000]), 14:0 PEG2000 PE (1,2-dimyristoyl-sn-glycero-3-phosphoethanolamine-N-[methoxy(polyethylene glycol)-2000]), 14:0 PEG2000 PE (1,2-dipalmitoyl-sn-glycero-3-phosphoethanolamine-N-[methoxy(polyethylene glycol)-2000]), 18:0 PEG2000 PE (1,2-distearoyl-sn-glycero-3-phosphoethanolamine-N-[methoxy(polyethylene glycol)-2000]) (DSPE-PEG2K), 18:1 PEG2000 PE (1,2-dioleoyl-sn-glycero-3-phosphoethanolamine-N-[methoxy(polyethylene glycol)-2000]), 14:0 PEG3000 PE (1,2-dimyristoyl-sn-glycero-3-phosphoethanolamine-N-[methoxy(polyethylene glycol)-3000]), 14:0 PEG3000 PE (1,2-dipalmitoyl-sn-glycero-3-phosphoethanolamine-N-[methoxy(polyethylene glycol)-3000]), 18:0 PEG3000 PE (1,2-distearoyl-sn-glycero-3-phosphoethanolamine-N-[methoxy(polyethylene glycol)-3000]) (DSPE-PEG3K), 18:1 PEG3000 PE (1,2-dioleoyl-sn-glycero-3-phosphoethanolamine-N-[methoxy(polyethylene glycol)-3000]), 14:0 PEG5000 PE (1,2-dimyristoyl-sn-glycero-3-phosphoethanolamine-N-[methoxy(polyethylene glycol)-5000]), 14:0 PEG5000 PE (1,2-dipalmitoyl-sn-glycero-3-phosphoethanolamine-N-[methoxy(polyethylene glycol)-5000]), 18:0 PEG5000 PE (1,2-distearoyl-sn-glycero-3-phosphoethanolamine-N-[methoxy(polyethylene glycol)-5000]) (DSPE-PEG5K), 18:1 PEG5000 PE (1,2-dioleoyl-sn-glycero-3-phosphoethanolamine-N-[methoxy(polyethylene glycol)-5000])), a PEG-ceramide (e.g., C8 PEG750 ceramide (N-octanoyl-sphingosine-1-{succinyl[methoxy(polyethylene glycol)750]}), C16 PEG750 ceramide (N-palmitoyl-sphingosine-1-{succinyl[methoxy(polyethylene glycol)750]}), C8 PEG2000 ceramide (N-octanoyl-sphingosine-1-{succinyl[methoxy(polyethylene glycol)2000]}), C16 PEG2000 ceramide (N-palmitoyl-sphingosine-1-{succinyl[methoxy(polyethylene glycol)2000]}), C8 PEG5000 ceramide (N-octanoyl-sphingosine-1-{succinyl[methoxy(polyethylene glycol)5000]}), C16 PEG5000 ceramide (N-palmitoyl-sphingosine-1-{succinyl[methoxy(polyethylene glycol)5000]}), an anionic lipid (e.g., 1,2-di-O-tetradecyl-sn-glycero-3-phospho-(1'-rac-glycerol), 1,2-dihexadecanoyl-sn-glycero-3-phospho-(1'-sn-glycerol)), and a cationic lipid (e.g., DC-cholesterol (3β-[N—(N',N'-dimethylaminoethane)-carbamoyl]cholesterol), 18:1 TAP (DOTAP) (1,2-dioleoyl-3-trimethylammonium-propane), 1-oleoyl-2-[6-[(7-nitro-2-1,3-benzoxadiazol-4-yl)amino]hexanoyl]-3-trimethylammonium propane, 14:0 TAP (1,2-dimyristoyl-3-trimethylammonium-propane), 16:0 TAP (1,2-dipalmitoyl-3-trimethylammonium-propane), 18:0 TAP (1,2-stearoyl-3-trimethylammonium-propane), DOTMA (1,2-di-O-octadecenyl-3-trimethylammonium propane), a phosphatidylcholine (e.g., 12:0 EPC (1,2-dilauroyl-sn-glycero-3-ethylphosphocholine), 14:0 EPC (1,2-dimyristoyl-sn-glycero-3-ethylphosphocholine), 14:1 EPC (1,2-dimyristoleoyl-sn-glycero-3-ethylphosphocholine), 16:0 EPC (1,2-dipalmitoyl-sn-glycero-3-ethylphosphocholine), 18:0 EPC (1,2-distearoyl-sn-glycero-3-ethylphosphocholine), 18:1 EPC (1,2-dioleoyl-sn-glycero-3-ethylphosphocholine), 16:0-18:1 EPC (1-palmitoyl-2-oleoyl-sn-glycero-3-ethylphosphocholine)). In some embodiments, the second amphiphile comprises 1,2-distearoyl-sn-glycero-3-phosphoethanolamine-N-[methoxy(polyethylene glycol)-2000]. In some embodiments, the second amphiphile comprises 1,2-distearoyl-sn-glycero-3-phosphoethanolamine-N-[methoxy(polyethylene glycol)-5000]. In some embodiments, the second amphiphile comprises lecithin. In some embodiments, the second amphiphile consists essentially of, or consists of, one or more materials described herein.

The proportion of the second amphiphile relative to the core in the particle depends on the characteristics of the second amphiphile, the properties of the core, and the application. In some embodiments, the second amphiphile is in the range from about 1% by weight to about 50.0% by weight compared with the weight of the core. The second amphiphile can be in the range from about 1% by weight to about 45% by weight, from about 1% by weight to about 40% by weight, from about 1% by weight to about 35% by weight, from about 1% by weight to about 30% by weight, from about 1% by weight to about 25% by weight, from about 1% by weight to about 20% by weight, from about 1% by weight to about 15% by weight, from about 1% by weight to about 10% by weight, and/or from about 1% by weight to about 5% by weight compared with the weight of the core. For example, the second amphiphile can be about 2% by weight, about 5% by weight, about 10% by weight, about 15% by weight, about 20% by weight, about 25% by weight, about 30% by weight, about 35% by weight, about 40% by weight, about 45% by weight, or about 50% by weight compared with the weight of the core.

The particle size can be in a range from about 10 nm to about 100 μm. In some embodiments, the size can be in a range from about 10 nm to about 10 μm, from about 10 nm to about 1000 nm, from about 20 nm to about 500 nm, from about 40 nm to about 200 nm, and/or from about 70 nm to about 150 nm. For example, the particle size can be about 10 nm, about 20 nm, about 40 nm, about 60 nm, about 80 nm, about 100 nm, about 120 nm, about 140 nm, about 160 nm, about 180 nm, or about 200 nm.

In some embodiments, the particles present within a population, e.g., in a composition, can have substantially the same shape and/or size (i.e., they are "monodisperse"). For example, the particles can have a distribution such that no more than about 5% or about 10% of the particles have a diameter greater than about 10% greater than the average diameter of the particles, and in some cases, such that no more than about 8%, about 5%, about 3%, about 1%, about 0.3%, about 0.1%, about 0.03%, or about 0.01% have a diameter greater than about 10% greater than the average diameter of the particles.

In some embodiments, the diameter of no more than 25% of the particle varies from the mean particle diameter by more than 150%, 100%, 75%, 50%, 25%, 20%, 10%, or 5% of the mean particle diameter. It is often desirable to produce a population of particle that is relatively uniform in terms of size, shape, and/or composition so that most of the particles have similar properties. For example, at least 80%, at least 90%, or at least 95% of the particles produced using the methods described herein can have a diameter or greatest dimension that falls within 5%, 10%, or 20% of the average diameter or greatest dimension. In some embodiments, a population of particles can be heterogeneous with respect to size, shape, and/or composition.

In non-limiting embodiments, FIG. 4 shows the size of some particles of the disclosure. FIG. 4A shows particle size at different stages in the formulation process with an siRNA payload, measured by dynamic light scattering. No detectable size was observed in the acetone solution of different components until siRNA and a certain amount of water was added, which indicates the dispersed state of lipids in the water-miscible solvent. However, cationic lipids and siRNA molecules can form nanocomplexes in the organic solution, with a diameter around 26 nm. The NPs formed after nanoprecipitation are around 100 nm in diameter. FIG. 4B shows transmission electron microscopy (TEM) image of the NPs. Samples for TEM were stained with 1% uranyl acetate and observed using Tecnai G2 Spirit BioTWIN microscope (FEI Company, Hillsboro, Oreg.) operating at 80 kV.

In some embodiments, a particle has a surface zeta potential in the range from about −80 mV to about +80 mV. In some embodiments, the particle can have a surface zeta potential in the range from about −40 mV to about +50 mV, from about −30 mV to about +40 mV, from about −20 mV to about +40 mV, and/or from about −50 mV to about +30 mV. For example, the particle can have a surface zeta potential of about −80 mV, about −70 mV, about −60 mV, about −50 mV, about −40 mV, about −30 mV, about −20 mV, about −10 mV, about 0 mV, about +10 mV, about +20 mV, about +30 mV, about +40 mV, about +50 mV, about +60 mV, or about +70 mV.

FIGS. 3A-3F show non-limiting embodiments of some particles of the disclosure. The lipid-polymer hybrid core enables efficient encapsulation and sustained release of a payload (e.g., a nucleic acid such as siRNA). The outer lipid and/or PEG can allow the NPs to evade immune recognition and increase circulation half-life. The particles can have a structure composed of a water-insoluble polymer-amphiphile hybrid core surrounded by a lipid and lipid-PEG layer (FIG. 3A), or lipid-PEG layer (FIG. 3B), or lipid layer (FIG. 3C). The outer lipid-PEG shell can be modified with targeting ligand that can facilitate tissue targeting (FIG. 3D). The lipid-polymer hybrid core can further carry a second agent for synergistic disease treatment or the development of synthetic vaccines containing both antigens and adjuvants (FIG. 3E). Furthermore, the PEG molecule can be first conjugated with the polymer before the NP formulation. The PEGylated polymers can self-assemble into stable NPs (FIG. 3F) in the aqueous solution without lipids or lipid-PEGs.

Payloads

The methods and compositions described herein are useful for delivering a payload. In some embodiments, the payload is delivered to a biological target. The payload can be used, e.g., for labeling (e.g., a detectable agent such as a fluorophore), or for therapeutic purposes (e.g., a cytotoxin or other drug molecule). In some embodiments, a payload is negatively charged (i.e., anionic). In some embodiments, a payload is positively charged (i.e., cationic).

In some embodiments, a payload has a surface zeta potential in the range from about −80 mV to about +80 mV. In some embodiments, the payload can have a surface zeta potential in the range from about −40 mV to about +50 mV, from about −30 mV to about +40 mV, from about −20 mV to about +40 mV, and/or from about −50 mV to about +30 mV. For example, the payload can have a surface zeta potential of about −80 mV, about −70 mV, about −60 mV, about −50 mV, about −40 mV, about −30 mV, about −20 mV, about −10 mV, about 0 mV, about +10 mV, about +20 mV, about +30 mV, about +40 mV, about +50 mV, about +60 mV, or about +70 mV.

The proportion of the payload relative to the core in the particle depends on the characteristics of the payload, the properties of the core, and the application. In some embodiments, the payload is loaded in the range from about 0.01% by weight to about 100.0% by weight compared with the weight of the core. The payload can be in the range from about 1% by weight to about 80% by weight, from about 1% by weight to about 75% by weight, from about 1% by weight to about 70% by weight, from about 1% by weight to about 65% by weight, from about 1% by weight to about 60% by weight, from about 1% by weight to about 55% by weight, from about 1% by weight to about 50% by weight, from about 1% by weight to about 45% by weight, from about 1% by weight to about 40% by weight, from about 1% by weight to about 35% by weight, from about 1% by weight to about 30% by weight, from about 1% by weight to about 25% by weight, from about 1% by weight to about 20% by weight, from about 1% by weight to about 15% by weight, from about 1% by weight to about 10% by weight, and/or from about 1% by weight to about 5% by weight compared with the weight of the core.

In some embodiments, the particle can comprise one or more payloads differentially presented within and/or on the particle (e.g., one or more payloads encapsulated in the core, one or more payloads covalently attached to the polymer within the core, one or more payloads encapsulated in the shell, and/or one or more payloads attached to the shell). The loading of each payload is independently determined.

In some embodiments, a targeting molecule can be chemically conjugated to the second amphiphile before being subjected to the method of making. The targeting molecule is one or more of antibodies, antibody fragments, aptamers, peptides, aptides, sugars, small molecules, or combinations thereof. The targeting molecule can be presented on the surface of aforementioned particles (FIG. 3D) for targeting, e.g., drug delivery.

In some embodiments, a B-cell antigen or its epitope can be chemically conjugated to the hydrophilic region of the second amphiphile before being subjected to the method of making. The antigen molecule is one or more of proteins, peptides, sugars, small molecules, or combinations thereof. The antigen molecule can be presented on the surface of the particles (FIG. 3E) for targeting, e.g., an immune response.

The term "naked payload" as used herein refers to a payload which is not loaded into a delivery system, e.g., a particle of the present disclosure or a nanoparticle delivery system which may alter the properties, e.g., the pharmacokinetic properties, e.g., the in vivo half-life, of the payload in a subject. A naked payload can be any payload as described herein. In some embodiments, a naked payload can be a native biomolecule, e.g., a human interleukin-2 in a human subject. In some embodiments, a naked payload can be a therapeutic protein, e.g., a therapeutic antibody, such as adilimumab, in a human subject. In some embodiments, the naked payload can be a small molecule, e.g., a chemotherapeutic agent as described herein.

Drug Molecules

Drug molecules include small molecules and biomolecules. Small molecules are low molecular weight organic compounds (typically about 2000 daltons or less). In some embodiments, the molecular weight of the drug molecule is in the range from about 200 to about 2000, from about 200 to about 1800, from about 200 to about 1600, from about 200 to about 1400, from about 200 to about 1200, from about 200 to about 1000, from about 200 to about 800, from about 200 to about 600 daltons, from about 300 to about 2000, from about 300 to about 1800, from about 300 to about 1600, from about 300 to about 1400, from about 300 to about 1200, from about 300 to about 1000, from about 300 to about 800, and/or from about 300 to about 600 daltons. Examples include cytochalasin B, gramicidin D, ethidium bromide, emetine, mitomycin, etoposide, tenoposide, colchicin, daunorubicin, dihydroxy anthracin dione, mithramycin, actinomycin D, 1-dehydrotestosterone, glucocorticoids, procaine, tetracaine, lidocaine, amphotericin B, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof.

Other drug molecules include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, CC-1065, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), antifungal agents (e.g., butenafine, terbinafine, and naftifine), immunomodulating drugs (e.g., glatiramer acetate, fingolimod, teriflunomide, and dimethyl fumarate), and anti-mitotic agents (e.g., vincristine, vinblastine, paclitaxel, and maytansinoids).

Examples of suitable chemotherapeutic agents include any of: abarelix, aldesleukin, alitretinoin, allopurinol, altretamine, anastrozole, arsenic trioxide, asparaginase, azacitidine, bexarotene, bleomycin, bortezomib, busulfan, calusterone, capecitabine, carboplatin, carmustine, chlorambucil, cisplatin, cladribine, clofarabine, cyclophosphamide, cytarabine, dacarbazine, dactinomycin, dalteparin, dasatinib, daunorubicin, decitabine, denileukin, dexrazoxane, docetaxel, doxorubicin, dromostanolone, epirubicin, erlotinib, estramustine, etoposide, exemestane, filgrastim, floxuridine, fludarabine, fluorouracil, fulvestrant, gefitinib, gemcitabine, goserelin acetate, histrelin acetate, idarubicin, ifosfamide, imatinib, irinotecan, lapatinib ditosylate, lenalidomide, letrozole, leucovorin, leuprolide, levamisole, lomustine, meclorethamine, megestrol, melphalan, mercaptopurine, methotrexate, methoxsalen, mitomycin C, mitotane, mitoxantrone, nandrolone, nelarabine, nofetumomab, oxaliplatin, paclitaxel, pamidronate, pegaspargase, pegfilgrastim, pemetrexed, pentostatin, pipobroman, plicamycin, procarbazine, quinacrine, rasburicase, ruxolitinib, sorafenib, streptozocin, sunitinib, tamoxifen, temozolomide, teniposide, testolactone, thalidomide, thioguanine, thiotepa, topotecan, toremifene, tretinoin, uracil mustard, valrubicin, vinblastine, vincristine, vinorelbine, vorinostat, and zoledronate, or a pharmaceutically acceptable salt thereof.

Small molecules useful in the compositions and methods described herein bind with high affinity to a biopolymer, such as protein, nucleic acid, or polysaccharide, or other biological target. Other examples include small molecules that bind specifically to receptors for hormones, such as steroid hormones (e.g., dihydrotestosterone and estradiol), melatonin, dopamine, or other signaling molecules, that may be delivered as described herein.

Biomolecules

Biomolecules are organic molecules having a molecular weight of 200 daltons or more produced by living organisms or cells, including large polymeric molecules such as polypeptides, proteins, polysaccharides, polynucleotides and nucleic acids (e.g., DNA or RNA, such as siRNA, mRNA, or shRNA), or analogs or derivatives of such molecules.

In some embodiments, the biomolecule comprises a nucleic acid. For example, the nucleic acid can be selected from the group consisting of siRNAs, microRNAs, mRNAs, and DNAs. The nucleic acid may be double-stranded (e.g., double-stranded DNA) or single-stranded (e.g., single-stranded RNA). The nucleic acid can comprise a vector (e.g., a plasmid or a viral vector, e.g., one derived from a retrovirus, a lentivirus, an adenovirus, or an adeno-associated virus). In some embodiments, the nucleic acid can reduce expression of a protein (e.g., a protein associated with a disease state, e.g., a kinase upregulated in a cancer, such as BRAF-mutated melanoma). In some embodiments, the nucleic acid can introduce or enhance expression of a protein (e.g., to encode for a protein that is depleted in a disease state, e.g., normal CFTR protein to treat cystic fibrosis).

In some embodiments, the siRNA is siMYC (i.e., anti-MYC siRNA). In some embodiments, the siRNA is si-c-

MYC (i.e., anti-c-MYC siRNA). In some embodiments, the siRNA is siBRAF (i.e., anti-BRAF siRNA). In some embodiments, the siRNA is siBRAF$^{V600E}$ (i.e., anti-BRAF$^{V600E}$ siRNA).

In some embodiments, the biomolecule comprises a therapeutic protein, such as an antibody, a transmembrane protein, a growth factor, an enzyme, or a structural protein. Examples that can be used in any embodiment of the disclosed compositions include cytokines, such as transforming growth factor-beta (TGF-beta), interferons (e.g., interferon-alpha, interferon-beta, interferon-gamma), colony stimulating factors (e.g., granulocyte colony stimulating factor (GM-CSF)), thymic stromal lymphopoietin (TSLP), and the interleukins, e.g., interleukin-1, interleukin-2, interleukin-3, interleukin-4, interleukin-5, interleukin-6, interleukin-7, interleukin-8, interleukin-10, interleukin-12, interleukin-13, interleukin-15, interleukin-17, interleukin-18, interleukin-22, interleukin-23, and interleukin-35; polypeptide hormones, such as amylin, anti-Müllerian hormone, calcitonin, cholecystokinin, corticotropin, endothelin, enkephalin, erythropoietin (EPO), follicle-stimulating hormone, gallanin, gastrin, ghrelin, glucagon, gonadotropin-releasing hormone, growth hormone-releasing hormone, hepcidin, human chorionic gonadotropin, human growth hormone (hGH), inhibin, insulin, insulin-like growth factor, leptin, luteinizing hormone, luteinizing hormone releasing hormone, melanocyte stimulating hormone, motilin, orexin, oxytocin, pancreatic polypeptide, parathyroid hormone, prolactin, secretin, somatostatin, thrombopoietin, thyroid-stimulating hormone, vasoactive intestinal peptide, and vasopressin; antibody-drug conjugates (e.g., trastuzumab emtansine, brentuximab vedotin, T-DM1); antibody fragment-drug conjugates; protein-drug conjugates; peptide-drug conjugates (e.g., paclitaxel-Angiopep 2, BMTP-11 (Arrowhead Research), zoptarelin doxorubicin, and NGR-hTNF); fusion proteins (i.e., a chimeric protein formed by the expression of two or more genes that encode for different proteins), e.g., Fc fusion proteins, which contain an antibody Fc unit that can offer stability or selective targeting of a cell or tissue type, including therapeutic proteins, such as ataci-cept, abatacept, aflibercept, alefacept, belatacept, etanercept, sotatercept, romiplostim, and rilonacept, bispecific fusion proteins (i.e., bispecific antibodies), which comprise two arms from different antibodies, and are thereby able to target two different types of antigens, such as Ec-LDP-Hr-AE, MM-111 (Merrimack Pharmaceuticals), and IMCgp100 (Immunocore Ltd.), and multimeric fusion proteins, which are fusion proteins created by engineered multimerization (e.g., with streptavidin or using leucine zippers), such as polyvalent IgG2a Fc (M045); enzymes, e.g., agalsidase beta, imiglucerase, velaglucerase alfa, taliglucerase, alglucosidase alfa, laronidase, idursulfase, and galsulfase; and antibodies, including therapeutic antibodies, e.g., anticancer antibodies (e.g., abagovomab, adecatumumab, afutuzumab, alacizumab pegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, zalutumumab), and anti-inflammatory antibodies (e.g., adalimumab, alemtuzumab, atlizumab, canakinumab, certolizumab, certolizumab pegol, daclizumab, efalizumab, fontolizumab, golimumab, infliximab, mepolizumab, natalizumab, omalizumab, ruplizumab, ustekinumab, visilizumab, zanolimumab, vedolizumab, belimumab, otelixizumab, teplizumab, rituximab, ofatumumab, ocrelizumab, epratuzumab, eculizumab, and briakinumab). Further examples of useful therapeutic proteins can be found in U.S. Pat. Nos. 8,349,910; and 8,043,833; U.S. patent applications 2013/0195888; and 2007/0092486; and PCT WO 2014/130064, each of which is hereby incorporated by reference in its entirety. In some embodiments, biomolecules can be sensitive to physiological environments, e.g., to physiologic enzymes or local pH, before delivery to the target tissue or target cell.

In some embodiments, a payload consists essentially of, or consist of, one or more species as described herein.

The compositions of the disclosure can provide for controlled release or sustained release of a payload (e.g., a biomolecule) in a biological system, e.g., when a biomolecule is delivered to a subject in need of therapy. Controlled release refers to delivery of an agent at a controlled rate for an extended time or in response to a stimulus (e.g., upon a change in pH or temperature, or in the presence of an enzyme). Controlled release of a payload can provides a well-characterized and reproducible dosage form. Sustained release refers to the release of a payload over an extended period of time. In sustained release, the rate and duration of payload release can be controlled to achieve a particular profile. A sustained release profile can include zero-order release, exponential decay, step-function release, or other release profiles that carry over a period of time, e.g., one to several hours (e.g., about 8 hours or 24 hours), one to several days (e.g., about 2, 3, 4, 5, 6, 7, 10, or 14 days), one to several weeks (e.g, about 2, 3, or 4 weeks) or one to several months (e.g., about 2, 3, 4, 5, or 6 months). The terms "zero-order release", "exponential decay" and "step-function release" as well as other sustained release profiles are well known in the art.

The controlled release profiles can afford enhanced pharmacokinetic profiles of a payload within a subject, compared with a naked payload that has not been loaded into a particle of the disclosure. An enhanced pharmacokinetic profile can exhibit an improved property of one or more selected from AUC, half-life, clearance, mean residence time, and volume of distribution (Vss), and can be shown in a given subject and route of administration as described herein. In some embodiments, the AUC of a payload in a particle of the disclosure is in a range from about 100% to about 100,000%, from about 100% to about 1000%, from about 150% to about 700%, or from about 200% to about 500% of the AUC of a naked payload, or wherein the AUC of the payload in the particle is about 150%, about 200%, about 250%, about 300%, about 350%, about 400%, about 450%, about 500%, or greater than 500% of the AUC of a naked payload. In some embodiments, the half-life of a payload in a particle of the disclosure is in a range from about 100% to about 100,000%, from about 100% to about 1000%, from about 100% to about 500%, from about 150% to about 400%, or from about 200% to about 300% of the half-life of a naked payload, or wherein the half-life of the payload in the particle is about 150%, about 200%, about 250%, about 300%, or greater than 400% of the half-life of a naked payload. In some embodiments, the clearance of a payload in a particle of the disclosure is in a range from about 1% to about 100%, from about 10% to about 90%, from about 20% to about 80%, from about 30% to about 70%, or from about 40% to about 80% of the clearance of a naked payload, or wherein the clearance of the payload in the particle is about 3%, about 5%, about 10%, about 15%, about 20%, about 25%, about 30%, about 40%, about 50%, about 60%, about 70%, or about 80% of the clearance of a naked payload. In some embodiments, the mean residence time of a payload in a particle of the disclosure is in a range from about 100% to about 100,000%, from about 100% to about 1000%, from about 150% to about 700%, or from about 200% to about 500% of the mean residence time of a naked payload, or wherein the mean residence time of the payload in the particle is about 150%, about 200%, about 250%, about 300%, about 350%, about 400%, about 450%, about 500%, or greater than 500% of the mean residence time of a naked payload.

Methods of Making

This disclosure provides a method of preparing a particle comprising a core comprising a water-insoluble polymer, a payload, and a first amphiphile, comprising obtaining a first solution comprising a water-insoluble polymer, a payload and a first amphiphile in a water-miscible solvent; and mixing the first solution with an aqueous second solution to form an aqueous composition comprising a particle comprising the water-insoluble polymer; the payload; and the first amphiphile.

In some embodiments, the method further comprises mixing the aqueous composition with a solution comprising a second amphiphile. The second amphiphile can thus form a shell surrounding the particle comprising the water-insoluble polymer; the payload; and the first amphiphile.

Figure 1:
FIG. 1 is a schematic of particle components.
Figure 1:
Figure 1:
Figure 1:
Figure 1:
Figure 1:
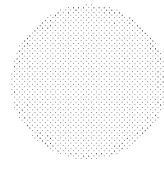
Figure 1:
Figure 2:
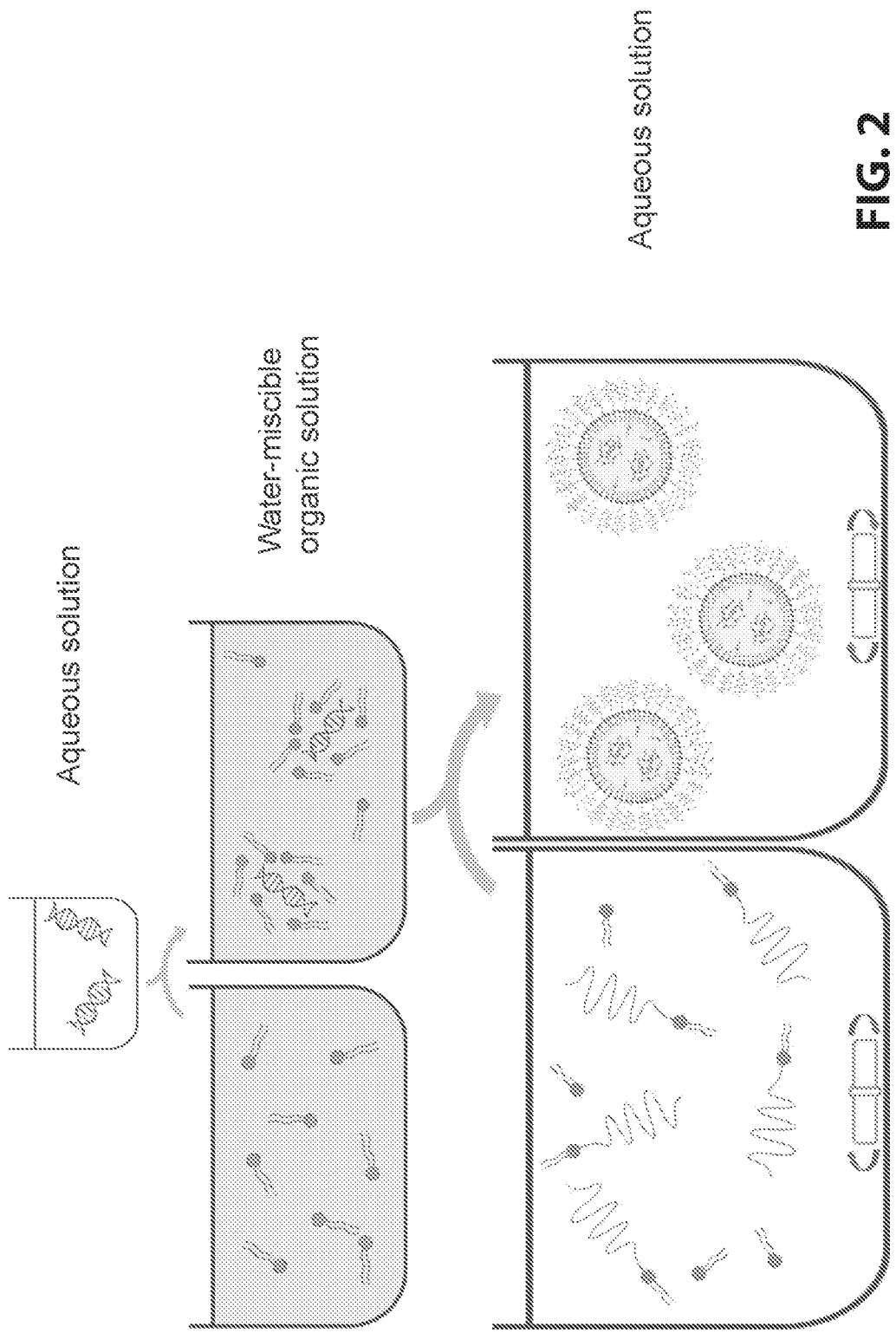
FIG. 2 is a diagram of the process for particle formulation.

The particles of the disclosure can be made by self-assembly under one-step precipitation methods described herein. The process can avoid use of detergents, sonication, or other harsh formulation techniques, and thus offers a simple and convenient synthetic approach which may be amenable to clinical use. In a non-limiting embodiment, the process may be performed as shown in FIG. 2. The water-insoluble polymer (e.g., poly(D,L-lactic acid) (PLA), poly (D,L-glycolic acid) (PLGA), poly(ε-caprolactone) (PCL), poly(ethylene glycol)-co-poly(D,L-lactic acid) (PEG-PLA), PEG-PLGA, PEG-PCL, and/or mixtures of the polymers or copolymers) and the first amphiphile can be first dissolved in water-miscible solvent (e.g., acetone, dimethylformamide, and/or methanol). The payload (e.g., a nucleic acid (e.g., siRNA, microRNA, mRNA, and/or DNA), protein, peptide, small molecular drug, and/or imaging agent) can be dissolved in water to form a first aqueous solution, and then added to the first organic solution to form a second aqueous solution. Optionally, the resulting second aqueous solution can be added to a third aqueous solution containing a second amphiphile. During the diffusion of the water-miscible solvent into the aqueous media, the water-insoluble polymer precipitates out together with the first amphiphile-payload complex to form a particle core that can be optionally surface-coated with a layer of a second amphiphile.

In some embodiments, a targeting molecule is chemically conjugated to the second amphiphile before being subjected to the method of making. The targeting molecule is one or more of antibodies, antibody fragments, aptamers, peptides, aptides, sugars, small molecules, or combinations thereof. The targeting molecule can be presented on the surface of aforementioned particles (FIG. 3D) for targeting, e.g., drug delivery. In a non-limiting embodiment, an antigen molecule (e.g., a B-cell antigen or its epitope) can be chemically conjugated to the hydrophilic region of the second amphiphile before being subjected to the method of making. The antigen molecule is one or more of proteins, peptides, sugars, small molecules, or combinations thereof. The antigen molecule can be presented on the surface of the particles (FIG. 3E) for targeting, e.g., an immune response.

In some embodiments, the water-insoluble polymer-amphiphile organic solution can be directly added to an aqueous medium to yield particles (FIG. 3F) by the rapid diffusion of the water-miscible solvent into the aqueous medium and subsequent evaporation of the solvent. This particle can be surface-functioned with targeting molecules for targeted delivery (FIG. 3D) or can encapsulate a second payload for codelivery (FIG. 3E).

Methods of Use

The methods of the disclosure offer the ability to deliver a payload, e.g., a biomolecule, to the desired biological target.

This disclosure provides for a method of delivering a payload to a cell, comprising contacting the cell with an effective amount of a composition as described herein. In some embodiments, the contacting is in vitro. In some embodiments, the contacting is in vivo. In some embodiments, the cell is a blood cell, a cancer cell, and immune cell (e.g., a macrophage cell), an epithelial cell (e.g., a skin cell), a bacterial cell, or a virus-infected cell.

In some embodiments, the cell is a macrophage cell. For example, the macrophage cell can be a RAW 264.7 cell. The macrophage cell can be unstimulated or stimulated by, for example, lipopolysaccharide (LPS).

In some embodiments, the cell is a cancer cell. In some embodiments, the cancer cell is selected from a breast cancer cell, a colon cancer cell, a leukemia cell, a bone cancer cell, a lung cancer cell, a bladder cancer cell, a brain cancer cell, a bronchial cancer cell, a cervical cancer cell, a colorectal cancer cell, an endometrial cancer cell, an ependymoma cancer cell, a retinoblastoma cancer cell, a gallbladder cancer cell, a gastric cancer cell, a gastrointestinal cancer cell, a glioma cancer cell, a head and neck cancer cell, a heart cancer cell, a liver cancer cell, a pancreatic cancer cell, a melanoma cancer cell, a kidney cancer cell, a laryngeal cancer cell, a lip or oral cancer cell, a lymphoma cancer cell, a mesothioma cancer cell, a mouth cancer cell, a myeloma cancer cell, a nasopharyngeal cancer cell, a neuroblastoma cancer cell, an oropharyngeal cancer cell, an ovarian cancer cell, a thyroid cancer cell, a penile cancer cell, a pituitary cancer cell, a prostate cancer cell, a rectal cancer cell, a renal cancer cell, a salivary gland cancer cell, a sarcoma cancer cell, a skin cancer cell, a stomach cancer cell, a testicular cancer cell, a throat cancer cell, a uterine cancer cell, a vaginal cancer cell, and a vulvar cancer cell. For example, the cancer cell can be a lung cancer cell, such as an NCI-H460 cell.

The present disclosure also provides for a method of treating a disease or condition in a subject in need thereof, comprising administering to the subject a therapeutically effective amount of a composition as described herein.

As used herein, a subject is a mammal, which can include a mouse, a rat, a guinea pig, a farm animal, such as a pig, a goat, a horse, or a cow, a non-human primate, such as a cynomolgus monkey, or a human. In some embodiments, the subject is a human.

The compositions of the disclosure may be used in any method of treating a disease or condition beneficially treated by administration of a payload, e.g., a biomolecule, in a subject.

The methods of the disclosure can be used to treat a cancer in a subject. Cancers include, but are not limited to, an adrenal cancer, a breast cancer, a colon cancer, a leukemia, a bile duct cancer, a bone cancer, a lung cancer (e.g., non-small cell lung cancer, small cell lung cancer, and lung carcinoid tumor), a bladder cancer, a brain cancer, a bronchial cancer, a cervical cancer, a colorectal cancer, an endometrial cancer, an ependymoma, a retinoblastoma, a gallbladder cancer, a gastric cancer, a gastrointestinal cancer, a glioma, a head and neck cancer, a heart cancer, a liver cancer, a pancreatic cancer, a melanoma, a kidney cancer, a laryngeal cancer, a lip or oral cancer, a lymphoma, a mesothioma, a mouth cancer, a myeloma, a nasopharyngeal cancer, a neuroblastoma, an oropharyngeal cancer, an ovarian cancer, a thyroid cancer, a penile cancer, a pituitary cancer, a prostate cancer, a rectal cancer, a renal cancer, a salivary gland cancer, a sarcoma, a skin cancer, a stomach cancer, a testicular cancer, a throat cancer, a uterine cancer, a vaginal cancer, and a vulvar cancer.

A payload (e.g., a biomolecule) can be useful to treat a cancer. In some embodiments, the payload comprises a therapeutic monoclonal antibody, including, but not limited to, abagovomab, adecatumumab, afutuzumab, alacizumab pegol, altumomab pentetate, amatuximab, anatumomab mafenatox, apolizumab, arcitumomab, bavituximab, bectumomab, belimumab, bevacizumab, bivatuzumab mertansine, blinatumomab, brentuximab vedotin, cantuzumab mertansine, cantuzumab ravtansine, capromab pendetide, cetuximab, citatuzumab bogatox, cixutumumab, clivatuzumab tetraxetan, dacetuzumab, demcizumab, detumomab, drozitumab, ecromeximab, eculizumab, elotuzumab, ensituximab, epratuzumab, etaracizumab, farletuzumab, figitumumab, flanvotumab, galiximab, gemtuzumab ozogamicin, girentuximab, ibritumomab tiuxetan, imgatuzumab, ipilimumab, labetuzumab, lexatumumab, lorvotuzumab mertansine, nimotuzumab, ofatumumab, oregovomab, panitumumab, pemtumomab, pertuzumab, tacatuzumab tetraxetan, tositumomab, trastuzumab, totumumab, zalutumumab.

A payload (e.g., a biomolecule) can comprise a polynucleotide (e.g., siRNA, miR, mRNA) targeting the expression and/or activity of one or more proteins (e.g., an enzyme, e.g., a kinase) associated with a cancer. In some embodiments, the polynucleotide can target a protein selected from the group consisting of: kinesin spindle protein (KSP), RRM2, keratin 6a (K6a), HER1, ErbB2, a vascular endothelial growth factor (VEGF) (e.g., VEGFR1, VEGFR3), a platelet-derived growth factor receptor (PDGFR) (e.g., PDGFR-α, PDGFR-β), epidermal growth factor receptor (EGFR), a fibroblast growth factor receptor (FGFR) (e.g., FGFR1, FGFR2, FGFR3, FGFR4), EphA2, EphA3, EphA4, HER2, HER3, HER4, INS-R, IGF-1R, IR-R, CSF1R, KIT, FLK-II, KDR/FLK-1, FLK-4, flt-1, c-Met, Ron, Sea, TRKA, TRKB, TRKC, FLT3, VEGFR/Flt2, Flt4, EphA1, EphB2, EphB4, Pim1, Pim2, Pim3, Tie2PKN3, PLK1, PLK2, PLK3, Src, Fyn, Lck, Fgr, Btk, Fak, SYK, FRK, JAK, Abl, Kit, KDR, CaM-kinase, phosphorylase kinase, MEKK, ERK, mitogen activated protein (MAP) kinase, phosphatidylinositol-3-kinase (PI3K), an AKT (e.g., Akt1, Akt2, Akt3), TGF-βR, KRAS, BRAF, a cyclin-dependent kinase (e.g., CDK1, CDK2, CDK4, CDK5, CDK6, CDK7, and CDK9), GSK3, a CDC-like kinase (CLK) (e.g., CLK1, CLK4), an Aurora kinase (e.g., Aurora A, Aurora B, and Aurora C), a mitogen-activated protein kinase kinase (MEK) (e.g., MEK1, MEK2), mTOR, protein kinase A (PKA), protein kinase C (PKC), protein kinase G (PKG), and PHB1.

The methods of the present disclosure can be used to treat an inflammatory disease, which includes arthritis, multiple sclerosis, rheumatoid arthritis, psoriasis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis, Paget's disease of bone, palindromic rheumatism, patellofemoral pain syndrome, Pellegrini-Stieda syndrome, pigmented villonodular synovitis, *piriformis* syndrome, plantar fasciitis, polyarteritis nodos, polymyalgia rheumatica, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, reperfusion injury, retrocalcaneal bursitis, rheumatic fever, rheumatoid vasculitis, rotator cuff tendinitis, sacroiliitis, *salmonella* osteomyelitis, sarcoidosis, saturnine gout, Scheuermann's osteochondritis, scleroderma, septic arthritis, seronegative arthritis, *shigella* arthritis, shoulder-hand syndrome, sickle cell arthropathy, Sjogren's syndrome, slipped capital femoral epiphysis, spinal stenosis, spondylolysis, *staphylococcus* arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis. Inflammatory diseases or conditions with an inflammatory component not triggered by autoimmunity are also included. See, for example, Tabas, I; Glass, C. K. Science 339 (6116): page 169 (2013):

Chronic diseases associated with an inflammatory component not directly induced by an auto-immune process are the most common diseases of aging and represent our greatest health threats. These include most forms of cardiovascular disease, type 2 diabetes, and virtually all neurodegenerative diseases. In each case, a nonautoimmune primary pathological process—for example, excess subendothelial apolipoprotein B—containing lipoproteins, saturated fatty acids, or formation of protein aggregates, respectively—results in the generation of DAMPs [damage-associated molecular patterns] that are detected by PRRs [pattern recognition receptors]. Moreover, the inflammatory response itself may amplify the production of disease-specific DAMPs, resulting in positive-feedback loops that accelerate the underlying disease process. For example, inflammation promotes formation of oxidized phospholipids that may serve as important DAMPs in atherosclerosis and may enhance the formation of β-amyloid and tau aggregates in Alzheimer's disease.

A payload (e.g., a biomolecule) can be useful to treat an inflammatory disease or condition. While improvements in recent years have led to advancements in the treatment of inflammatory diseases, significant challenges remain that may be overcome using a method of the present disclosure. See, for example, Tabas, I; Glass, C. K. Anti-Inflammatory Therapy in Chronic Disease: Challenges and Opportunities. Science 339 (6116): 166-172 (2013), which is herein incorporated by reference in its entirety. In some embodiments, the payload is a cytokine useful to treat an inflammatory disease, such as transforming growth factor-beta (TGF-beta), an interferon (e.g., interferon-alpha, interferon-beta, interferon-gamma), a colony stimulating factor (e.g., granulocyte colony stimulating factor (GM-CSF)), thymic stromal lymphopoietin (TSLP), and an interleukin (e.g., interleukin-1, interleukin-2, interleukin-3, interleukin-4, interleukin-5, interleukin-6, interleukin-7, interleukin-8, interleukin-10, interleukin-12, interleukin-13, interleukin-15, interleukin-17, interleukin-18, interleukin-22, interleukin-23, and interleukin-35). In some embodiments, the payload is a therapeutic antibody or an Fc fusion protein useful in the treatment of an inflammatory disease. Anti-inflammatory antibodies include adalimumab, alemtuzumab, atlizumab, canakinumab, certolizumab, certolizumab pegol, daclizumab, efalizumab, fontolizumab, golimumab, infliximab, mepolizumab, natalizumab, omalizumab, ruplizumab, ustekinumab, visilizumab, zanolimumab, vedolizumab, belimumab, otelixizumab, teplizumab, rituximab, ofatumumab, ocrelizumab, epratuzumab, eculizumab, and briakinumab. Exemplary useful Fc fusion proteins to treat inflammatory diseases include atacicept, abatacept, alefacept, etanercept, and rilonacept.

The methods of the disclosure can be used to treat viral infections, as an alternative to traditional vaccines. Many current vaccines against microbial pathogens comprise live attenuated or non-virulent strains of the causative microorganisms. Many vaccines comprise killed or otherwise inactivated microorganisms. Other vaccines utilize purified components of pathogen lysates, such as surface carbohydrates or recombinant pathogen-derived proteins. Vaccines that utilize live attenuated or inactivated pathogens typically yield a vigorous immune response, but their use has limitations. For example, live vaccine strains can sometimes cause infectious pathologies, especially when administered to immune-compromised recipients. Moreover, many pathogens, particularly viruses, undergo continuous rapid mutations in their genome, which allow them to escape immune responses to antigenically distinct vaccine strains. Given the difficulty of vaccine development, many vaccines are in extremely short supply. In some instances, vaccine shortages occur because not enough manufacturers devote their facilities to vaccine production to keep up with demand. In some cases, vaccine shortages are attributed to low potency of the vaccine, which means a large amount of vaccine product must be administered to each individual in order to achieve a prophylactic effect. For example, some vaccines cannot be administered as an intact organism (even if attenuated or killed) because they cause infectious pathologies. Instead, such vaccines usually comprise purified pathogen components, which typically lead to a much less potent immune response.

The methods of the disclosure can be used to prevent or to treat a viral disease in a subject. In some embodiments, the viral disease is selected from the group consisting of: Adenovirus infections, Herpes virus infections (e.g., HSV-1, HSV-2 and varicella zooster virus infections), Papillomavirus infections (e.g., HPV-1, HPV-2, HPV-5, HPV-6, HPV-11, HPV-13, HPV-16, and HPV-18), Parvovirus infections, Polyomavirus infections, Poxvirus infections, Arbovirus infection, Arenavirus infections, Astrovirus infections, Birnavirus infections, Bunyavirus infections, Calicivirus infections, Coronavirus infections, Flavivirus infections, Hantavirus infections, Hepatitis virus infections (e.g., Hepatitis A, Hepatitis B, Hepatitis C, and Hepatitis D), Mononegavirus infections (e.g., Bornavirus infections, Filovirus infections (e.g., Ebola virus, Marburg virus, and Cueva virus), Paramyxovirus infections (e.g., respiratory syncytial virus), and Rhabdovirus infections), Nidovirales Infections, Orthomyxoviridae infections (e.g., influenza virus infections), Picornavirus infections (e.g., Enterovirus infections), Reovirus infections (e.g., Rotavirus infections), Retrovirus infections (e.g., lentivirus infections, e.g., HIV infections), and Togavirus infections (e.g., Rubivirus infections).

A payload (e.g., a biomolecule) can be useful to prevent or to treat a viral disease. In some embodiments, the payload comprises a nucleic acid (e.g., siRNA) that can prevent the replication of a virus causing disease. In a non-limiting example, Bunyaviruses comprise genomes that contain a large (L), medium (M), and small (S) RNA segment. The L segment encodes for the RNA-dependent RNA polymerase, required for viral RNA replication and mRNA synthesis. The M segment encodes for the viral glycoproteins, which are exhibited on the surface of the viruses and assist in attaching to and entering a host cell. The S segment encodes the nucleocapsid protein. A payload (e.g., an siRNA) can target one or more regions of the L, M, and S segments of a Bunyavirus in order to silence expression of that segment, thereby preventing replication of the virus.

The methods of the disclosure can be used to treat a disease or a condition in need of enzyme replacement in a subject. For example, MPS disorders (mucopolysaccharidoses) are lysosomal storage diseases caused by the inability to produce specific enzymes, which in turn leads to an abnormal storage of mucopolysaccharides. In some embodiments, the disease in need of enzyme replacement is selected from the group consisting of: Gaucher disease, Fabry disease, Hurler syndrome (MPS I H), Scheie syndrome (MPS I S), Hurler-Scheie syndrome (MPS I H-S), Hunter syndrome (MPS II), Sanfilippo syndrome (e.g. Sanfilippo A (MPS III A), Sanfilippo B (MPS III B), Sanfilippo C (MPS III C), and Sanfilippo D (MPS III D)), Morquio syndrome (e.g. Morquio A (MPS IV A) and Morquio B (MPS IV B)), Maroteaux-Lamy syndrome (MPS VI), Sly syndrome (MPS VII), MPS IX (hyaluronidase deficiency), I-cell disease (ML II), Pseudo-Hurler polydystrophy (ML III), and Glycogen storage disease type II (Pompe disease).

A payload (e.g., a biomolecule) can be useful to treat a disease in need of enzyme replacement. In some embodiments, the payload comprises a protein (e.g., an enzyme) that is deficient and/or less active in a subject suffering from a disease in need of enzyme replacement. In some embodiments, the protein comprises one or more proteins selected from the group consisting of: agalsidase beta, imiglucerase, velaglucerase alfa, taliglucerase, alglucosidase alfa, laronidase, idursulfase, and galsulfase.

In some embodiments, a payload consists essentially of, or consist of, one or more species as described herein.

Administration

When employed as pharmaceuticals, the particles of the invention can be administered in the form of pharmaceutical compositions. Thus the present disclosure provides a composition comprising a particle, or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the particle of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active particle, soft and hard gelatin capsules, suppositories, sterile injectable solutions and sterile packaged powders.

In preparing a formulation, the active particle can be milled to provide the appropriate particle size prior to combining with the other ingredients. If the active particle is substantially insoluble, it can be milled to a size of less than 200 mesh. If the active particle is substantially water soluble, the size can be adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the subject by employing procedures known in the art.

In some embodiments, the pharmaceutical composition comprises silicified microcrystalline cellulose (SMCC) and at least one particle described herein, or a pharmaceutically acceptable salt thereof. In some embodiments, the silicified microcrystalline cellulose comprises about 98% microcrystalline cellulose and about 2% silicon dioxide w/w.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active particle may be effective over a wide dosage range and is generally administered in a therapeutically effective amount. It will be understood, however, that the amount of the particle actually administered will usually be determined by a physician, according to the relevant circumstances, including the condition to be treated, the chosen route of administration, the actual particle administered, the age, weight, and response of the individual subject, the severity of the subject's symptoms and the like.

The therapeutic dosage of a particle of the present invention can vary according to, e.g., the particular use for which the treatment is made, the manner of administration of the particle, the health and condition of the subject, and the judgment of the prescribing physician. The proportion or concentration of a particle of the invention in a pharmaceutical composition can vary depending upon a number of factors including dosage, chemical characteristics (e.g., hydrophobicity), and the route of administration. For example, the particles of the invention can be provided in an aqueous physiological buffer solution containing about 0.1 to about 10% w/v of the particle for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the particle selected, formulation of the excipient, and its route of administration. Effective doses can be extrapolated from dose-response curves derived from in vitro or animal model test systems.

The liquid forms in which the particles and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the particle of the invention. The topical formulations can be suitably packaged in tubes of, e.g., 100 g which are optionally associated with instructions for the treatment of the select indication, e.g., psoriasis or other skin condition.

The amount of particle or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the particle preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a particle of the present invention can vary according to, e.g., the particular use for which the treatment is made, the manner of administration of the particle, the health and condition of the subject, and the judgment of the prescribing physician. The proportion or concentration of a particle of the invention in a pharmaceutical composition can vary depending upon a number of factors including dosage, chemical characteristics (e.g., hydrophobicity), and the route of administration. For example, the particles of the invention can be provided in an aqueous physiological buffer solution containing about 0.1 to about 10% w/v of the particle for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the particle selected, formulation of the excipient, and its route of administration. Effective doses can be extrapolated from dose-response curves derived from in vitro or animal model test systems.

EXAMPLES

The invention is further described in the following examples, which do not limit the scope of the invention described in the claims.

Materials

Cationic amino molecules including ethylenediamine core-poly (amidoamine) (PAMAM) generation 0 dendrimer (G0), ethylenediamine branched polyethylenimine ($M_w$~800) (PEI), polypropylenimine tetramine dendrimer, generation 1 (DAB), and diethylene triamine (114) were purchased from Sigma-Aldrich. Ester-terminated poly(D,L-lactide-co-glycolide) (PLGA, viscosity of 0.26-0.54 dL/g) was purchased from Durect Corporation. DSPE-PEGs (1,2-distearoyl-sn-glycero-3-phosphoethanolamine-N-[methoxy (polyethylene glycol)]) with PEG molecular weight 3000 (DSPE-PEG3K) and 5000 (DSPE-PEG5K), C16 PEG5000 ceramide (ceramide-PEG5K), 1,2-dioleoyl-3-trimethylammonium-propane (chloride salt) (DOTAP), and 1,2-di-O-octadecenyl-3-trimethylammonium propane (chloride salt) (DOTMA) were obtained from Avanti Polar Lipids, and soybean lecithin from Alfa Aesar. Lipofectamine 2000 (Lipo2K) was purchased from Invitrogen. Steady-Glo luciferase assay system was purchased from Promega. siRNAs targeting luciferase (siLuc) and PHB1 (siPHB1), and fluorescent dye-labeled siRNAs (DY547-siRNA, DY647-siRNA, and DY677-siRNA) were acquired from Dharmacon.

The siRNA sequences are as follows: siLuc:
SEQ ID No. 1: 5'-CUU ACG CUG AGU ACU UCG AdTdT-3' (sense) and
SEQ ID No. 2: 5'-UCG AAG UAC UCA GCG UAA GdTdT-3' (antisense); and siPHB1:
SEQ ID No. 3: 5'-GCG ACG ACC UUA CAG AGC GUU-3' (sense); and
SEQ ID No. 4: 5'-CGC UCU GUAAGG UCG UCG CUU-3' (antisense).

DY547 and DY647 were labeled at the 5'-end of the sense strand of siLuc. DY677 was labeled at the 5'-end of both the sense and antisense strand of siLuc. MitoTracker Green (Life Technologies) was resuspended in dimethyl sulfoxide (DMSO; Sigma) and used at a final concentration of 200 nM. Alexa Fluor 488 phalloidin was purchased from Life Technologies. Antibodies used in this work included the following: anti-caspase 3, anti-caspase 9, anti-cleaved caspase 3, anti-cleaved caspase 9, anti-PARP, anti-EEA1, and anti-LAMP1 (Cell Signaling); Alexa Fluor® 488 Goat-anti Rabbit IgG (Life Technologies); anti-PHB1 (Abcam); and anti-β-actin (Sigma).

Measurements and General Protocols

Surface Charge Measurement

To measure the change of surface charge associated with lipid-PEG dissociation, NPs (5 mg/mL) were first incubated with 4% serum albumin at 37° C. At a predetermined time point, NP suspension was ultra-centrifuged, and washed with pure water. The NP pellet was then re-suspended for zeta potential measurement using dynamic light scattering (DLS).

Serum Stability Study

For the siRNA stability test, naked siRNA, NP(siRNA) or lipid-siRNA complexes were added to 100% murine serum (1:1 v/v) and incubated at 37° C. for the indicated times (0, 6, 12, and 24 hours). After incubation, siRNA NPs and siRNA-lipid complexes were ultra-centrifuged for 15 min. The pellet was dissolved in chloroform and siRNA was extracted with 0.1% SDS/0.5 M NaCl aqueous solution. Then the siRNA extracts or naked siRNA were loaded and separated on E-Gel® precast agarose gels (4%) containing ethidium bromide (Life Technologies) and visualized under UV light.

siRNA Release Kinetics

To determine the release kinetics, DY547-labeled siRNA was first encapsulated into the hybrid NPs. A suspension of NPs in PBS was aliquoted (100 µL) into semipermeable minidialysis tubes (MWCO 100 kDa; Pierce) and dialyzed against frequently renewed PBS (pH 7.4) at 37° C. with gentle stirring. At a predetermined time, one minidialysis tube was removed and the NPs were disintegrated with DMSO. The fluorescence intensity of DY547-siRNA (ex/em: 530/590 nm) was measured using Synergy HT multi-mode microplate reader (BioTek Instruments Inc.).

Lipid-PEG Dissociation Kinetics

The dissociation of lipid-PEG molecules from NPs in simulated serum (4% serum albumin in PBS) was studied using a modified method based on spectrophotometric measurement of a complex formed between PEG and barium iodide (Cheng, T. L., Chuang, K. H., Chen, B. M. & Roffler, S. R. Bioconjug. Chem. 23, 881-899 (2012)). NPs were first incubated in albumin solution at 37° C. At a predetermined time point, NP suspension was ultra-centrifuged, washed with de-ionized water, and re-suspended in 100 µL water. Then the NP solution (1.25 mg/mL at PLGA polymer weight) was mixed with 100 µl DMSO, 20 µl $BaCl_2$ (5%) and 20 µl $I_2$ solution (0.1 N, Alfa Aesar). Calibration curve was prepared with corresponding lipid-PEG solution with same concentration of PLGA (1.25 mg/mL) and G0-C14 (0.125 mg/mL). After incubation at room temperature for 15 minutes, absorbance at 535 nm was measured on the microplate reader.

Cell Culture

Luciferase-expressing HeLa (Luc-HeLa) cells and RAW264.7 macrophage cells were maintained in Dulbecco's Modified Eagle's Medium (DMEM; Invitrogen) with high glucose, 10% (v/v) fetal bovine serum (FBS; Sigma). Non-small cell lung cancer A549 cells were maintained in F-12K medium (Invitrogen) supplemented with 10% (v/v) FBS. NCI-H460 cells were maintained in RPMI-1640 medium (Invitrogen) supplemented with 10% (v/v) FBS. All cells were incubated at 37° C. in 5% $CO_2$.

Luciferase Silencing

Luc-HeLa cells were seeded into 96-well plates (5,000 cells per well) and allowed to attach in growth medium at 37° C. in a 5% CO2 incubator overnight. Cells were then transfected with NP(siLu) or Lipo2K-siLuc complexes at siRNA concentration of 50 nM, 10 nM, 5 nM, and 1 nM for 24 hours unless otherwise specified. Lipo2K-siLuc complexes were prepared according to the manufacturer's protocol. Luc-HeLa cells were then washed with fresh medium and further cultured in medium for another 48 hours unless otherwise specified. The expression of firefly luciferase in HeLa cells was determined using Steady-Glo luciferase assay kits. Cell number or cytotoxicity was measured using AlamarBlue assay. The luminescence or fluorescence intensity was measured using microplate reader. All the in vitro transfection experiments were performed in triplicate.

NP Uptake and Intracellular Trafficking

For cellular uptake kinetics study, HeLa cells or RAW264.7 cells were seeded into 96-well plates and allowed to attach for 24 hours. Then the cells were incubated with NP(DY547-siRNA) at the siRNA concentration of 50 nM for different periods of time (1, 3, 6, 12, 18, and 24 hours), and then washed with PBS, fixed with 4% paraformaldehyde, and stained with Hoechst (2 µg/mL) for nuclei identification. For the uptake mechanism study with small molecule inhibitors, HeLa cells were first pre-incubated for 30 minutes with the small molecules, and then treated with NP(DY547-siRNA) for 6 hours in the presence of endocytic inhibitors. 5-(N-ethyl-N-isopropyl) amiloride (EIPA) was used as the macropinocytosis inhibitor, filipin as the caveolae-mediated endocytosis inhibitor, and chlorpromazine as the clathrin-mediated endocytosis inhibitor (Cayman Chemical). For the uptake mechanism study with endocytic probes, HeLa cells were seeded on cover slips. Uptake experiments were conducted with addition of AF488-labeled probes (transferrin, cholera toxin B and dextran, Life Technologies) in the last hour of the 2-hour NP incubation period. Subsequently, the cells were washed with PBS, fixed with 4% paraformaldehyde, and stained with Hoechst (2 µg/mL) for nuclei identification. Images were acquired on laser scanning confocal fluorescence microscope (Leica SP5 X, Leica Microsystems) or Inverted Fluorescence Microscope (Zeiss Axiovert 200) and analyzed using Fiji/Image-J software.

To monitor the intracellular trafficking of the NPs, HeLa cells were first pre-incubated with NP(DY547-siRNA) for 3 hours (pulse), followed by 0-3 hour chase. Cells were then washed and immunostained with primary antibodies for EEA1(C45B10) or LAMP1(D2D11) (Cell Signaling), and AF488 linked secondary antibodies according to the protocol described below. Images were acquired on Leica SP5 X confocal fluorescence microscope and analyzed using Fiji/ImageJ software.

Immunofluorescent Staining

For immunofluorescent staining, cells were first washed with ice-cold PBS, fixed in 4% paraformaldehyde at room temperature for 15 minutes, followed by three washes with PBS (5 minutes each). Subsequently, cells were permeabilized by incubation in 0.2% Triton X-100-PBS for 8 minutes on ice and blocked with PBS blocking buffer containing 2% normal goat serum, 2% BSA and 0.2% gelatin for 1 hour at room temperature. Cells were incubated in appropriated diluted primary antibody for 1 hour at 4° C. overnight. After rinsing the cells three times with PBS, fluorescent dye linked secondary antibodies were applied for 1 hour at room temperature. The cells were then washed again with PBS, counterstained with Hochest 33342 or DAPI and mounted on slides with Prolong Gold antifade mounting media (Life Technologies). For mitochondrial staining, MitoTracker Green was added into cells and incubated for 1 hour before fixation according to the manufacturer's instructions (Life Technologies). For actin staining, cells were incubated with Alexa Fluor 488 phalloidin (Life Technologies). Images for intracellular trafficking were acquired on Leica SP5 X confocal fluorescence microscope. PHB1 and mitochondria staining were visualized using Leica DM-IRE2 inverted fluorescence microscope (Leica Microsystems). For in vivo immunofluorescence analysis, tumor tissue was snap frozen followed by harvesting and embedding in optimal cutting temperature compound (Tissue Tek). 7-μm cryostats sections were cut and collected on super frost-treated glass slides. Then tissue slices were stained as described above for imaging. Images were acquired on Inverted Fluorescence Microscope (Zeiss Axiovert 200).

Caspase-3/7 Activity Measurement

To assess caspase-3/7, 48 hours after NP treatment, A549 or NCI-H460 cells were seeded in white 96-well plates at a density of 5,000 cells/well in triplicates. After 24 hours post-seeding, caspase-3/7 activity was assayed using the Caspase-Glo 3/7 assay kits (Promega) as per manufacturer's instructions.

Flow Cytometry Analysis

Forty eight hours post-NP treatment, both NP(siPHB1)- and NP(siControl)-treated cells were seeded in 6-well plates and grown overnight. The supernatant and the cell monolayer were collected, washed with PBS, and processed for detection of apoptotic cells using the Annexin V-PE/7-AAD apoptosis detection kit (BD Biosciences) according to manufacturer's instructions.

Western Blot Analysis

Protein extracts were prepared using the modified radioimmunoprecipitation assay lysis buffer (50 mM Tris-HCl pH 7.4, 150 mM NaCl, 1% NP-40 substitute, 0.25% sodium deoxycholate, 1 mM sodium fluoride, 1 mM $Na_3VO_4$, 1 mM EDTA), supplemented with protease inhibitor cocktail (Cell Signaling) and 1 mM phenylmethanesulfonyl fluoride or complete Mini protease inhibitor tablets (Roche). Equal amounts of protein, as determined with a bicinchoninic acid (BCA) protein assay kit (Pierce/Thermo Scientific) according to the manufacturer's instructions, were resolved on SDS-PAGE gels and transferred to nitrocellulose or polyvinylidene difluoride membrane. The blots were blocked with 5% nonfat dry milk or 3% BSA in TBST (50 mM Tris-HCl, pH 7.4 and 150 mM NaCl, and 0.1% Tween 20) and then incubated with appropriate primary antibodies. Signals were detected with horseradish peroxidase-conjugated secondary antibodies and enhanced chemiluminescence (ECL) detection system (Pierce). When indicated, membranes were subsequently stripped for reblotting.

Specifically, A549 or NCI-H460 cells were seeded on 6-well plates (200,000 cells/well) and transfected with NP(siPHB1), NP(siControl) or Lipo2K-siPHB1 complexes with 40 nM siRNA. Two days after transfection, cell lysates were prepared in lysis buffer (Cell Signaling) containing protease inhibitor cocktail (Cell Signaling) and 1 mM phenylmethanesulfonyl fluoride. Protein concentration was measured by using BCA Protein Assay kit (Pierce). An equal amount of protein (30 μg) was separated by Novex® Tris-Glycine 4-12% gradient gels (Invitrogen) and then transferred onto a polyvinylidene difluoride membrane (Bio-rad). The membrane was then incubated with anti-PHB1 and β-actin antibodies at 4° C. overnight. After incubation with the HRP-linked anti-rabbit secondary antibodies, signals were visualized by chemiluminescence detection reagents (Cell Signaling). All antibodies were purchased from Cell Signaling.

In Vitro Cell Proliferation and NP Cytotoxicity

For cell proliferation study, A549 or NCI-H460 cells were plated on 12-well plates (20,000 cells/well) and allowed to attach overnight. The cells were transfected with NP(siPHB1) or NP(siControl) for 24 hours, and then washed with fresh medium for further incubation. At different time points, cell number or cytotoxicity was measured by AlamarBlue assay according to the manufacturer's protocol. The AlamarBlue assay agent is non-toxic, which allows us to continuously monitor the cell proliferation in real time. After each measurement, the AlamarBlue agents were washed away and replaced with fresh growth medium for further cell growth. To examine the cytotoxicity of combination treatment by NP(siPHB1) and cisplatin, A549 or NCI-H460 cells were seeded in 96-well plates and allowed to adhere overnight. Then the cells were transfected with NP(siPHB1) or NP(siControl) at the siRNA concentration of 10 nM for 24 hours. One or two days after transfection, cells were incubated with cisplatin at different concentrations for another 72 hours. The cytotoxicity was then measured with AlamarBlue assay.

Animals

Animals were obtained from the Charles River Laboratories. All in vivo studies were performed in accordance with National Institutes of Health animal care guidelines and in strict pathogen-free conditions in the animal facility of Brigham and Women's Hospital. Animal protocol was approved by the Institutional Animal Care and Use Committees on animal care (Harvard Medical School). The animals were allowed free access to sterile food pellets and water.

Animal Models of NSCLC Xenograft

For the NCI-H460 tumor xenograft model, $3 \times 10^6$ cells in 100 μL of culture medium were implanted in the subcutaneous space on the bilateral flanks of 4-5-week-old female athymic nude mice. Once tumors were established, animals were intravenously injected with saline, NP(siControl), or NP(siPHB1) (600 μg/kg siRNA) for three consecutive days. Two days after the last injection, the mice were sacrificed, and the tumors were harvested and snap-frozen. The tumor tissue was cut to small pieces and weighed; and 5 μl of lysis buffer was added to per milligram of tissue. Western-blot was performed as described above. Tumor tissues were fixed with 4% paraformaldehyde and embedded in paraffin. Tissue sections were stained for TUNEL assay according the manufacturer's protocol. The tumor size was measured by caliper and calculated as volume=length×(width)$^2$/2. Data are presented as mean±SD (n=4 mice per group). P<0.01; *P<0.001, one-way ANOVA.

For A549 tumor xenograft model, $3\times10^6$ cells were suspended in 1:1 (v/v %) media and Matrigel (BD Biosciences) and implanted subcutaneously into the flank of 4-5-week-old female athymic nude mice.

Pharmacokinetic Study

For in vivo pharmacokinetic studies, normal BALB/c mice were intravenously injected with fluorophore (DY647)-labeled siRNA NPs or naked DY647-siRNA through the tail vein. At different time points, blood was drawn retroorbitally and siRNA fluorescence was measured using the BioTek microplate reader (BioTek Instruments Inc., Winooski, Vt.). Standard curve was generated by measuring the fluorescence intensity of different amounts of NP(DY647-siRNA) or free DY647-siRNA added in blood from untreated mice. Total blood volume was estimated as 58.5 mL blood per kg of body weight.

Biodistribution

For in vivo biodistribution study, female athymic nude mice bearing NCI-H460 xenograft were intravenously injected with near-infrared fluorophore (DY677)-labeled siRNA NPs or naked DY677-siRNA through the tail vein. 24 hours after administration, mice were imaged using the Syngene PXi imaging system (Synoptics Ltd). Organs and tumors were also harvested and imaged. To quantify the siRNA accumulation, organs and tumors harvested from mice were weighted and homogenized. Fluorescence of the homogenate was measured using the Syngene PXi imaging system and quantified by ImageJ.

Statistics

Statistical analyses of the data were performed with SPSS program 16.0 by using two tails student's t-test. All experiments, unless otherwise stated, were performed in triplicate. Error bars used in this work are standard deviations (S.D.), unless otherwise noted. A p<0.05 is considered statistically significant (*p<0.05, p<0.01, and *p<0.001).

Example 1

Synthesis of Lipid-Polymer Hybrid NPs

Example 1A siRNA

As illustrated in FIG. 2, the lipid-polymer hybrid NPs self-assemble together with siRNA through a robust two-step approach. Aqueous siRNA was first mixed with the acetone solution containing cationic lipids (or lipid-like compounds) and PLGA polymer with a 1:20 volume ratio. With water rapidly and homogeneously dispersing in acetone, the negatively charged siRNA molecules self-assembled with cationic lipids (e.g., G0-C14) into NPs with a size in the range of about 20-30 nm (FIG. 4A), as measured by dynamic light scattering (DLS).

In brief, 5 mg PLGA and a certain amount of cationic lipid or lipid-like compound (e.g., G0-C14) are dissolved in 1 mL acetone solvent. A 50 μL siRNA (4 nmol) solution is mixed with the acetone solution to form siRNA/cationic lipid nanocomplexes. Next, the polymer solution with the nanocomplexes was added dropwisely into a 20 mL aqueous solution containing 4 mg lipid-PEG (e.g., DSPE-PEG5K) and 0.32 mg lecithin. The NPs formed instantly upon mixing. The residual acetone in the suspension was evaporated by continuously stirring the suspension at room temperature for 2 hours. NPs were washed three times in Amicon tubes (MWCO 100 kDa; Millipore) to remove any remaining water-miscible solvent and free compounds with ice-cold water, and concentrated in 1 mL phosphate buffered saline (PBS) solution. The size and surface charge (zeta potential) were determined by Dynamic Light Scattering or DLS (15-mW laser, incident beam of 676 nm; Brookhaven Instruments Corporation). NP samples for transmission electron microscopy (TEM) were stained with 1% uranyl acetate and imaged using Tecnai $G^2$ Spirit BioTWIN microscope (FEI Company) operating at 80 kV.

Acetone has little to no apparent effect on the integrity and bioactivity of siRNA (FIGS. 5A and 5B). By adding the acetone solution to a rapid mixing, bulk aqueous solution of lecithin and lipid-PEG, the PLGA polymer and cationic lipid/siRNA complex were together nanoprecipitated to form a solid NP core surrounded by a lecithin/lipid-PEG shell.

Figure 6A:
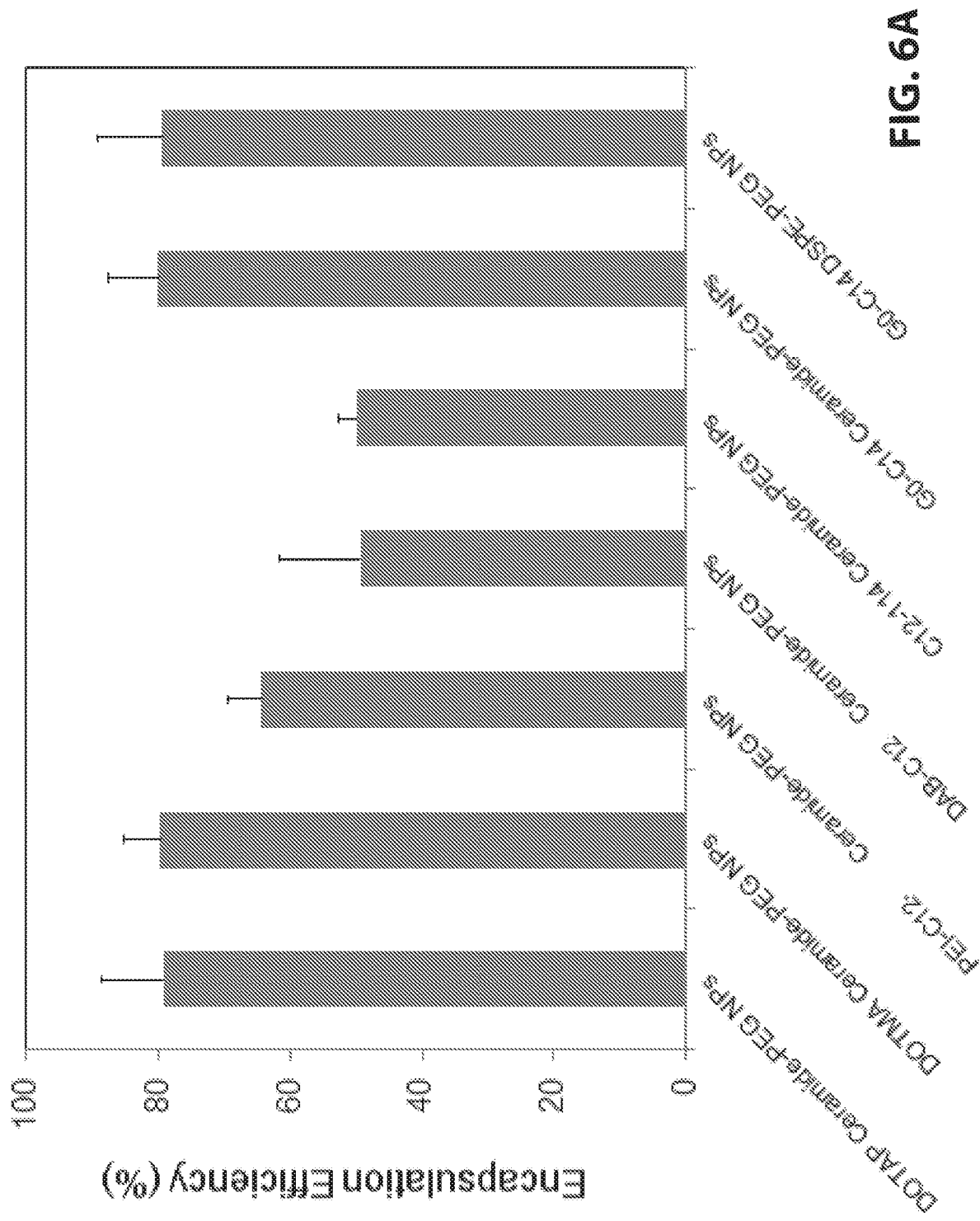
FIG. 6A: Encapsulation efficiency of DY547-labeled siRNA (DY547-siRNA) loaded NPs with different cationic lipids and lipid-PEGs.
Figure 6B:
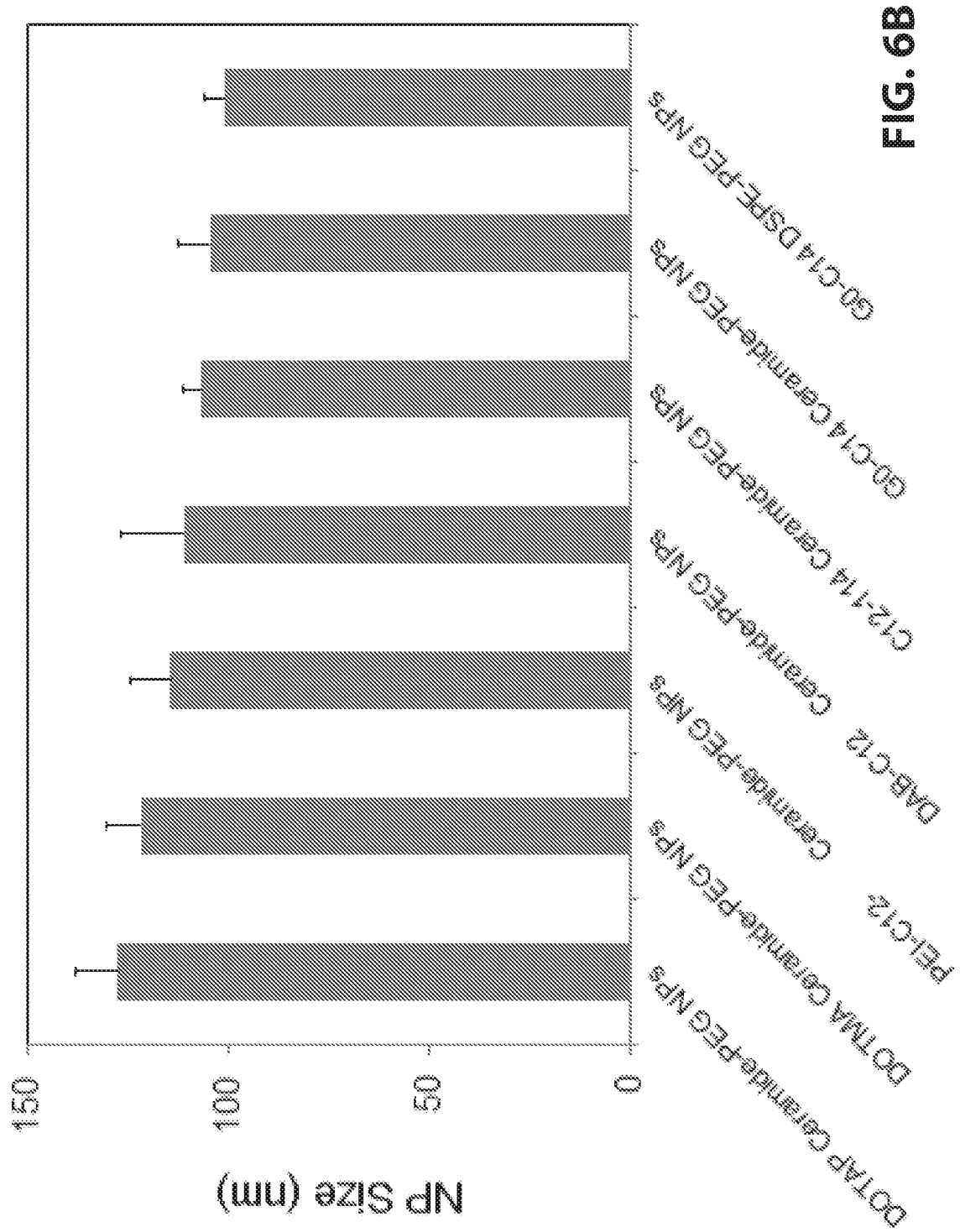
FIG. 6B: Size of NPs with different cationic lipids and lipid-PEGs. For the determination of encapsulation efficiency, NPs were ultra-centrifuged, and the pellet was dissolved with DMSO. The amount of encapsulated DY547-siRNA (ex/em: 530/590 nm) was measured by Synergy HT microplate reader (BioTek Instruments Inc., Winooski, Vt.). NP size was determined by using a dynamic light-scattering method (15-mW laser, incident beam of 676 nm; Brookhaven Instruments Corporation).
Figure 6C:
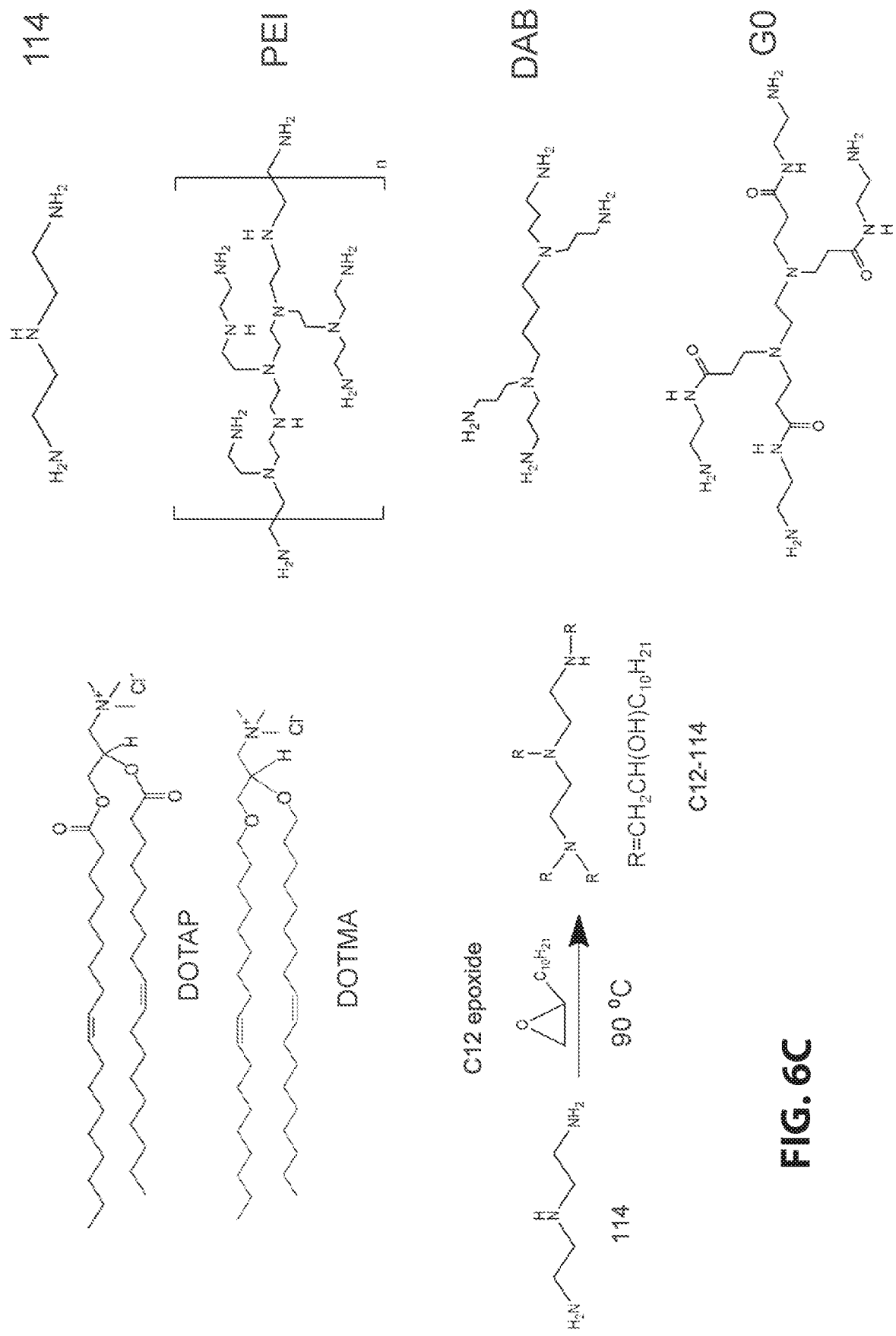
FIG. 6C shows the chemical structure of cationic lipids or lipid-like compounds, including cationic lipid DOTAP and DOTMA, the synthesis of cationic lipid-like compounds through ring opening reaction, and amino moieties of the cationic lipid-like compounds.

The effect of cationic lipids and lipid-PEGs on siRNA encapsulation efficiency and NP size is shown in FIG. 6. Cationic lipid-like compounds were synthesized by reacting alkyl epoxides with a selection of amines (FIG. 6C), according to a previously described procedure (Xu, X., et al., Proc. Natl. Acad. Sci. U.S.A. 110, 18638-18643 (2013); Love, K. T., et al. Proc. Natl. Acad. Sci. U.S.A. 107, 1864-1869 (2010)). Substoichiometric amounts of epoxide were added to increase the proportion of products with one less tail than the total possible for a given amine monomer. The amine (1 equiv) and epoxide (½N−1 equiv, where N is the number of secondary amines plus 2× number of primary amines in the amine starting material) were reacted under vigorous stirring at 90° C. for 2 d. For example, G0-C14 compound was synthesized by mixing PAMAM dendrimer G0 with 1,2-epoxytetradecane at a molar ratio of 1:7. The crude reaction mixture was separated by chromatography on silica with a gradient elution from $CH_2Cl_2$ to 75:22:3 $CH_2Cl_2$/MeOH/$NH_4OH$.

Figure 7A:
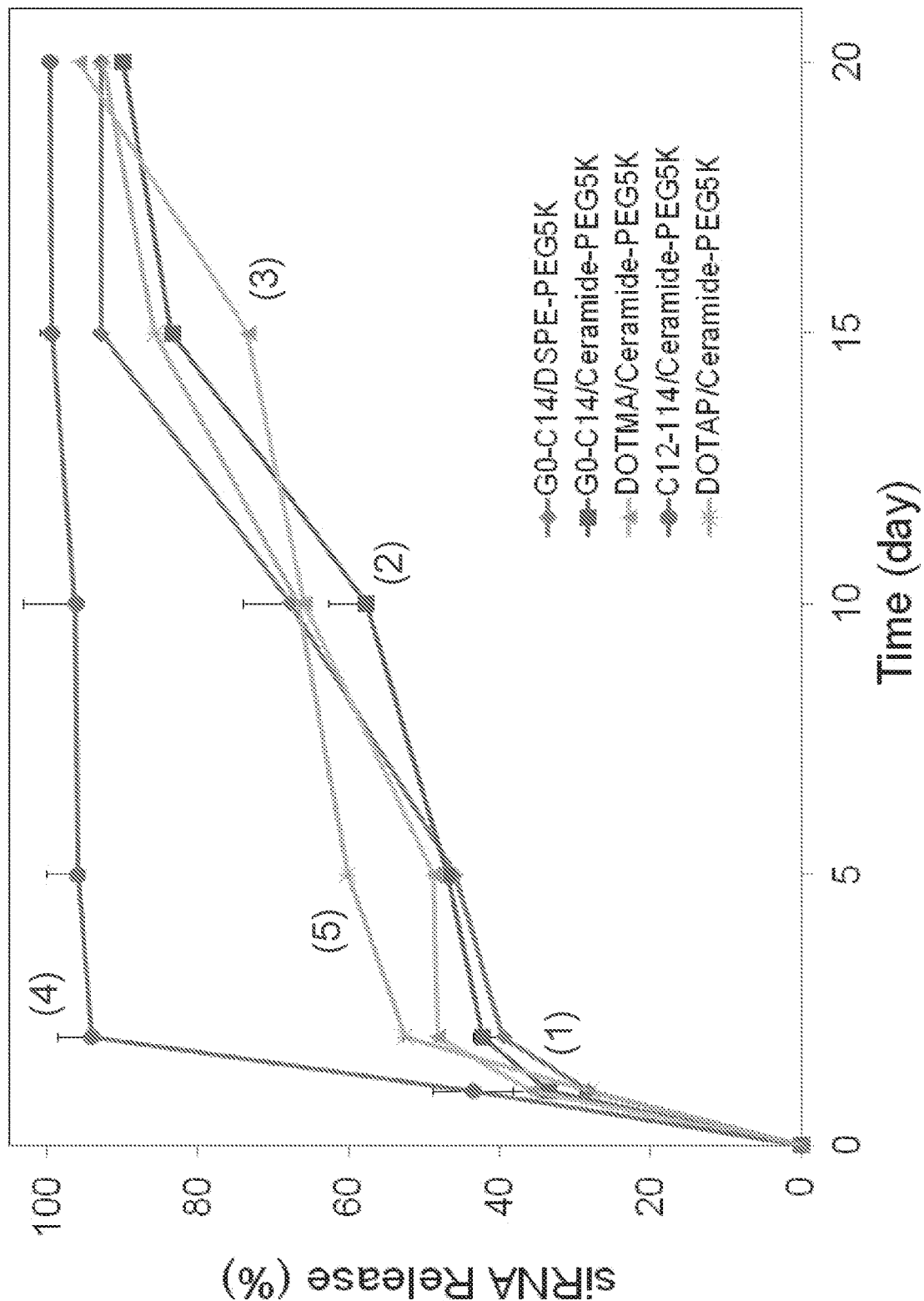
FIG. 7A shows the in vitro siRNA release profiles of NPs composed of different cationic lipids or lipid-PEGs. Curves: (1) G0-C14 cationic lipid, DSPE-PEG5K shell, (2) G0-C14 cationic lipid, ceramide-PEG5K shell, (3) DOTMA cationic lipid, ceramide-PEG5K shell, (4) C12-114 cationic lipid, ceramide-PEG5K shell, (5) DOTAP lipid, ceramide-PEG5K shell. For release kinetics measurement, a suspension of DY547-siRNA loaded NPs was dialyzed against PBS buffer (pH 7.4) in semipermeable minidialysis tubes (MWCO 100 kDa; Pierce) at 37° C. with stirring. At a predetermined time, an aliquot of the NP suspension was removed and dissolved with DMSO. The fluorescence intensity (ex/em: 530/590 nm) was measured by Synergy HT multi-mode microplate reader (BioTek Instruments Inc., Winooski, Vt.).
Figure 7B:
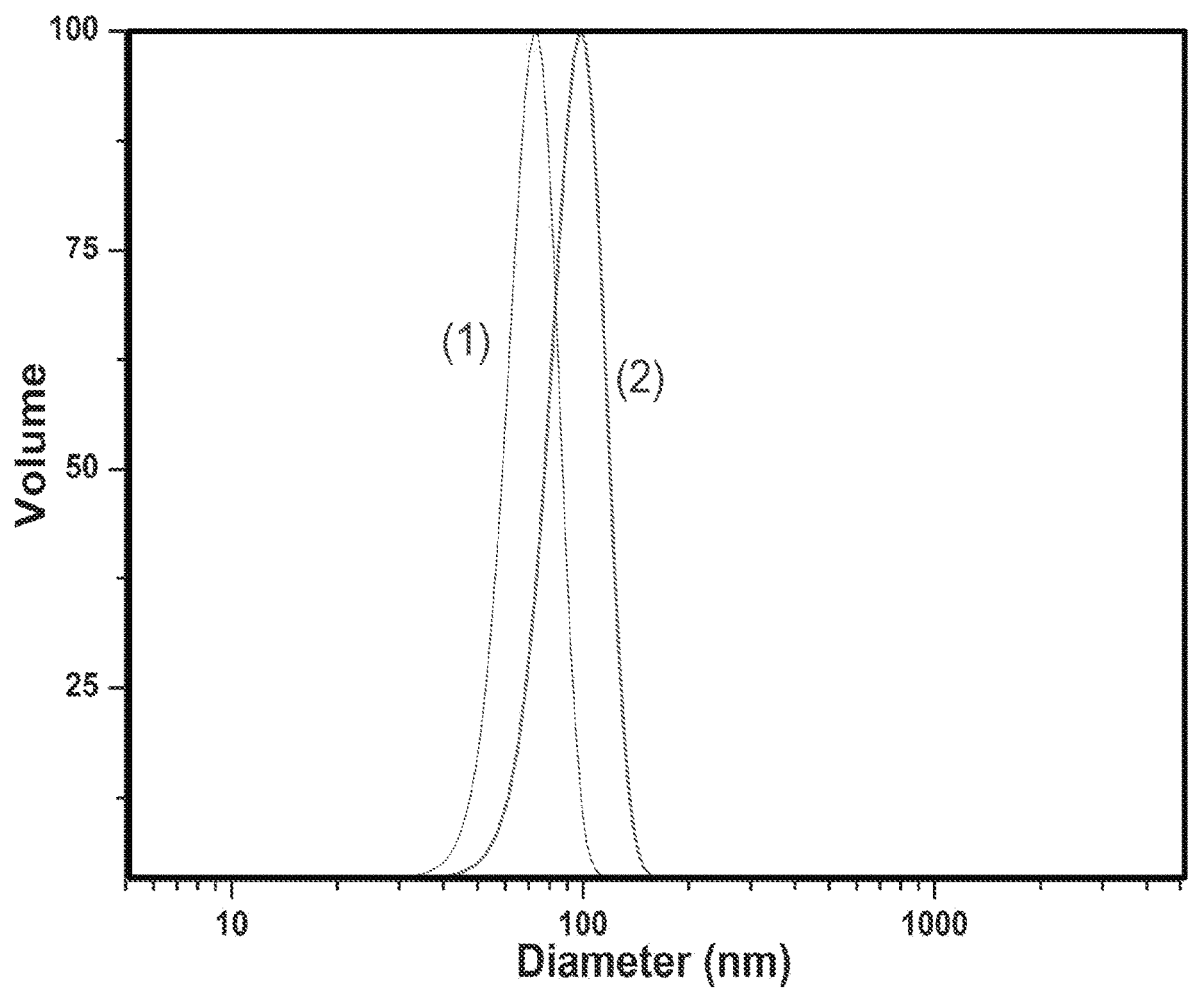
FIG. 7B shows size distribution of the G0-C14/DSPE-PEG NPs prepared using acetone vs. dimethylformamide, as measured by DLS.

With G0-C14 as the cationic lipid component, the hybrid NP was about 100 nm in size (FIGS. 4A and 4B), with siRNA encapsulation efficiency at about 80% and a loading of about 640 pmol siRNA/mg PLGA. Different cationic lipids and lipid-PEG molecules were also demonstrated to have an influence on the particle size, siRNA encapsulation and release kinetics (FIG. 6A-6C, 7A). Notably, the size of the G0-C14 siRNA NPs can be further modified, e.g., reduced to about 70 nm when the water-miscible solvent is changed from acetone (curve (2)) to dimethylformamide (curve (1), FIG. 7B). As compared to previous lipid-polymer hybrid RNAi NPs that were generally prepared by double emulsion and solvent evaporation technique (see, e.g., Shi, J., Xiao, Z., Votruba, A. R., Vilos, C. & Farokhzad, O. C. Differentially charged hollow core/shell lipid-polymer-lipid hybrid nanoparticles for small interfering RNA delivery. Angew. Chem. Int. Ed. Engl. 50, 7027-7031 (2011); Xu, X., et al. Enhancing tumor cell response to chemotherapy through nanoparticle-mediated codelivery of siRNA and cisplatin prodrug. Proc. Natl. Acad. Sci. U.S.A. 110, 18638-18643 (2013); Shi, J., et al. Hybrid lipid-polymer nanoparticles for sustained siRNA delivery and gene silencing. Nanomedicine: NBM 10, 897-900 (2014); Diez, S., Migueliz, I. & Tros de Ilarduya, C. Targeted cationic poly (D,L-lactic-co-glycolic acid) nanoparticles for gene delivery to cultured cells. Cell. Mol. Biol. Lett. 14, 347-362 (2009); Wilson, D. S., et al. Orally delivered thioketal nanoparticles loaded with TNF-alpha-siRNA target inflammation and inhibit gene expression in the intestines. Nat. Mater. 9, 923-928 (2010)), this self-assembled hybrid NP is smaller, more uniform and can be easily made, while retaining comparable siRNA encapsulation efficiency. In addition, the solid PLGA polymer core offers a more rigid and stable nanostructure that can better protect the encapsulated siRNA than the lipid-siRNA complex (lipoplex) structure. Stability tests showed that the siRNA within the NPs underwent no noticeable degradation in serum within 24 hours, while free siRNA was quickly digested. In comparison to the siRNA complex with G0-C14 and lipid-PEG (lipid-siRNA complex), over 70% siRNA degradation was observed after 24-hour incubation in serum.

Notably, the siRNA NPs can be stored at −80 degree C. freezer for a long period of time (e.g., 12 months) without changing the NP size and losing the siRNA bioactivity, as demonstrated in FIG. 28.

Example 1B microRNA microRNAs (miRs) have tremendous therapeutic promise for different diseases including cancer, inflammatory diseases like atherosclerosis, and others, as they can target multiple proteins which often affect integrated functions and pathways toward a common endpoint. For example, miR-21 has been shown to promote inflammation resolution in atherosclerosis through silencing PDCD4 in macrophages, leading to the enhanced expression of IL-10 that is a potent pro-resolving protein with links to human coronary artery disease.

The particle platform developed above has been applied to miR delivery. The size (~100 nm) of miR NPs is similar to siRNA NPs, as measured by TEM and dynamic light scattering (DLS) (FIGS. 30A and 30B).

Example 1C mRNA mRNA has demonstrated huge potential for the development of therapeutics and vaccines. As a proof-of-concept study, the expression of eGFP on DC2.4 dendritic cells after incubation with eGFP mRNA-loaded NPs. DC2.4 cells were transfected with eGFP mRNA NPs at the concentration of 0.2 μg/mL for 24 h, then washed with PBS, and further incubated with cell culture medium. At 0, 1, and 3 days after transfection, images were acquired on inverted fluorescence microscope (Zeiss Axiovert 200) to examine the expression of eGFP. Significant expression of eGFP was observed in DC2.4 cells at 3 days after transfection, as indicated by the green fluorescence in FIG. 31A. Notably, the mRNA NP treatment led to 86.7% eGFP positive cells, which is much more efficient than Lipo2K-mRNA treatment with only 23.4% positive transfection (FIG. 31B). In addition, the mRNA NPs show no toxicity under the experimental conditionals for DC2.4 transfection (FIG. 31C).

Example 1D

Protein Loaded Particles

Proteins are promising therapeutic agents for diseases treatment and can work as antigens for effective vaccine development. For example, many genetic diseases are caused by a loss of function or lack of production of particular enzymes such as alpha galactosidase in Fabry disease. Without a cure, the victim faces a life of suffering. However, to remedy the symptoms, enzyme replacement is possible, be it through protein delivery. By relying on a NP delivery vehicle, the enzyme can be protected from the harsh environment in the body and could possibly be directed to particular cells through modifications, thus reducing possible side effects and improving therapeutic efficacy compared to free enzyme.

The particle platform disclosed herein can also be used for protein/enzyme delivery. Results in FIG. 32 show the features of the protein particles. Proteins can be encapsulated at a concentration as high as 20 mg/mL without significant increase in NP size. DMSO is one suitable solvent for protein NP formulation, leading to small particle size, high encapsulation efficiency, and the retaining of protein activity (>80%).

Example 1E

Peptide Particles

Targeted NP delivery shows the promise to further enhance drug accumulation and penetration in disease tissues. For example, targeting moiety iRGD, which binds to $\alpha v\beta 3$ and $\alpha v\beta 5$ integrins on cancer cells, can be conjugated to DSPE-PEG-COOH using EDC/NHS chemistry. The DSPE-PEG-iRGD bioconjugate can then be mixed with unconjugated DSPE-PEG in water as the solution for precipitation as described in the methods herein, to yield iRGD-NPs for targeted drug delivery. FIG. 33 shows that the iRGD-targeted NPs can enhance the siRNA uptake in PC3 and DU145 prostate cancer cells, as compared to non-targeted NPs.

Example 1F

Fluorescent Particles

Theranostic NPs, which simultaneously carry therapeutic and imaging agents, enable real-time monitoring of pharmacokinetics, biodistribution, and tissue accumulation of nanotherapeutics. This can therefore facilitate the evaluation and optimization of nanotherapeutics in preclinical and clinical studies, and can be used to prescreen cancer subjects to determine those likely to respond well to nanotherapeutic interventions and exclude those who may suffer from severe off-target toxicity. In addition, by tracking therapeutic responses, it could also help clinicians make decisions about dosage, frequency, drug choice, and treatment strategies. Moreover, theranostic NP technologies can be very useful in analyzing drug distribution at the target site, visualizing drug release in the extra- and intracellular environment, and facilitating triggered drug release.

Figure 34A:
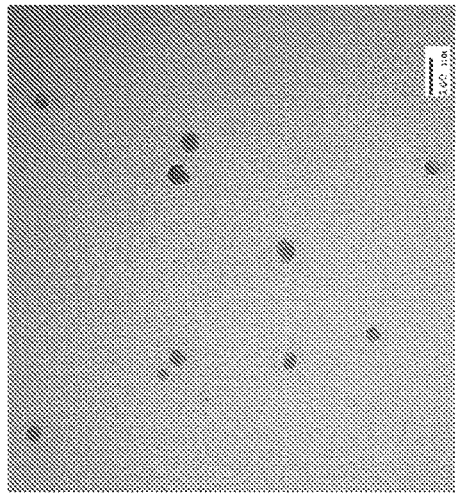
Figure 34B:
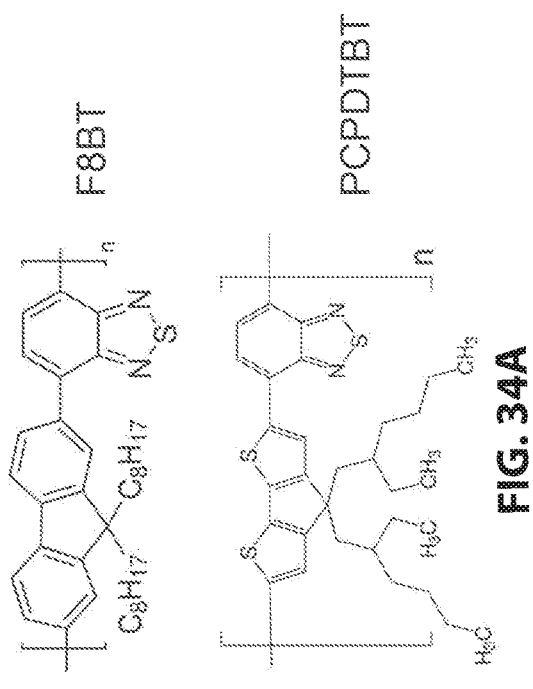

In this example, fluorescent polymers (e.g., F8BT and PCPDTBT in FIG. 34A) were used to form NPs loaded with G0-C14/siRNA complexes. The NP formulation uses the methods of making as described herein, with fluorescent polymers. FIG. 34B shows the TEM image of these NPs.

Example 2

NP-Mediated siRNA Delivery In Vitro

The siRNA release profiles from NPs composed of different cationic lipids or lipid-PEGs are shown in FIG. 7. The degree and rate of payload (e.g., siRNA) release can depend on the water-insoluble polymer and the first amphiphile within the core.

Example 2A

HeLa Cells

Figure 8A:
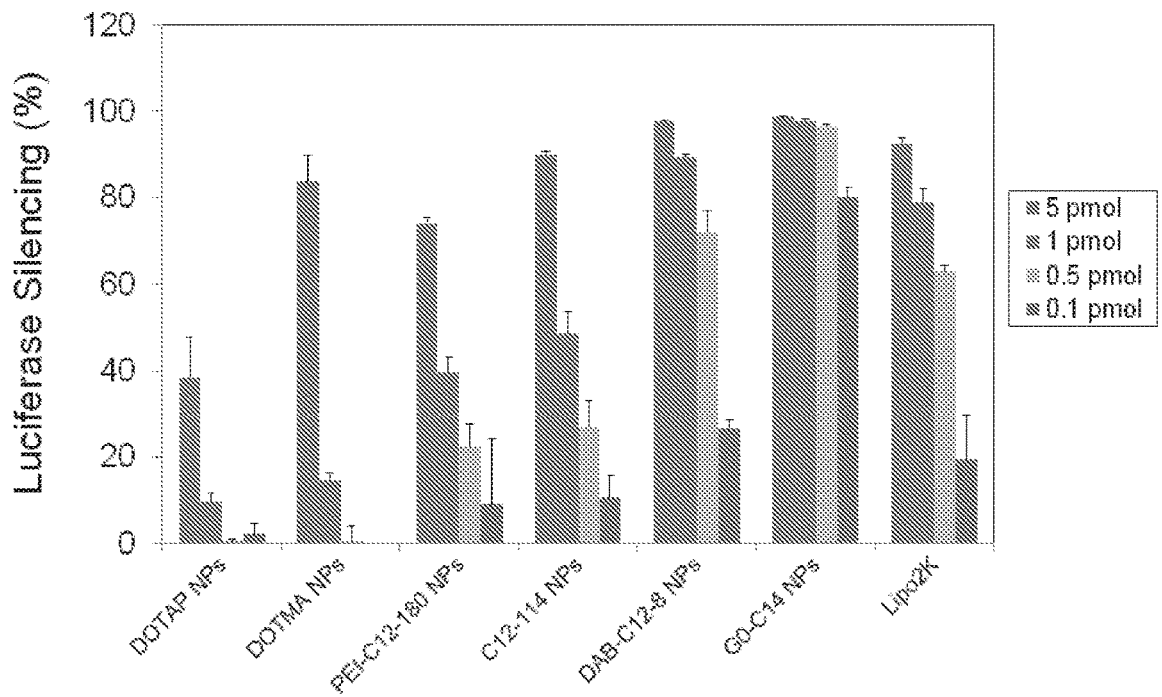
FIG. 8A: Luciferase silencing in luciferase-expressed HeLa (Luc-HeLa) cells by lipofectamine 2000 (Lipo2K) or NPs with different cationic lipids.
Figure 8B:
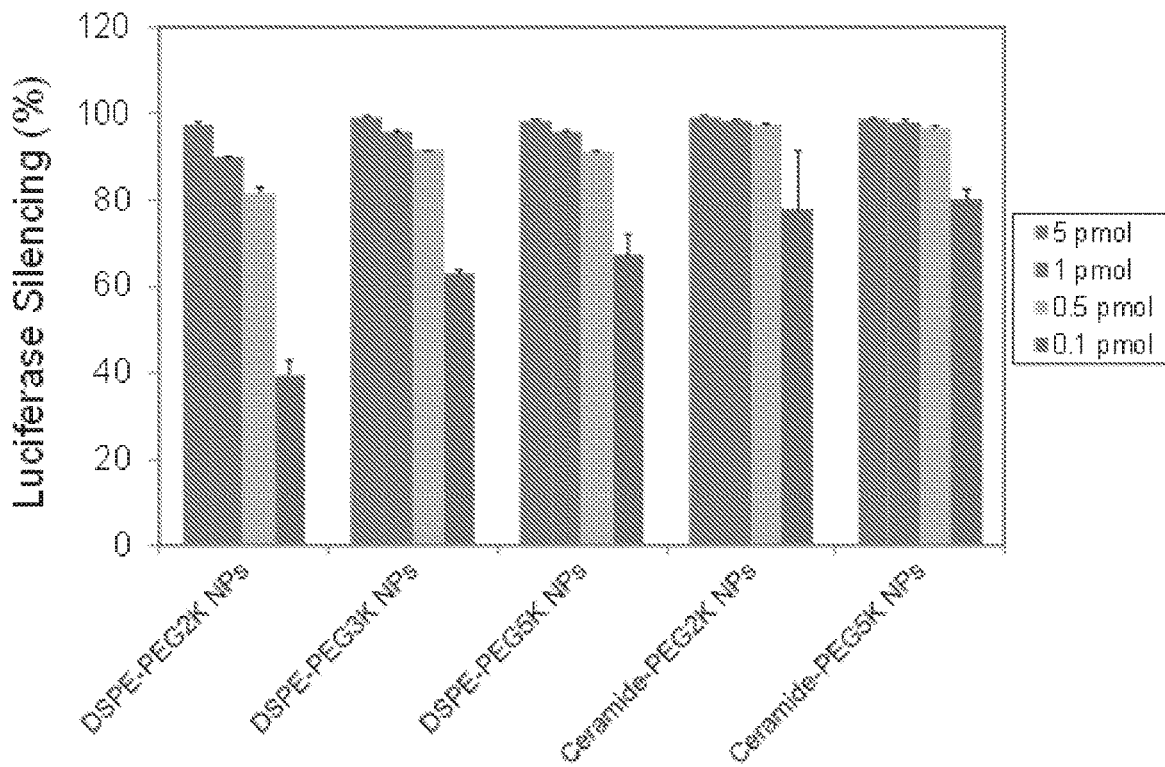
FIG. 8B: Luciferase silencing by NPs with different lipid-PEGs. The cationic lipid G0-C14 is used in all of NPs and the N/P (nitrogen/phosphorus) ratio is kept at 10:1. For the luciferase silencing assay, Luc-HeLa cells were transfected with NP(siLuc) or Lipo2K-siLuc complexes for 24 h at concentration of 50 nM, 10 nM, 5 nM, and 1 nM. The cells were then washed with fresh medium and further incubated for two days. The expression of firefly luciferase in Luc-HeLa cells was determined by Luciferase assay kit.
Figure 9A:
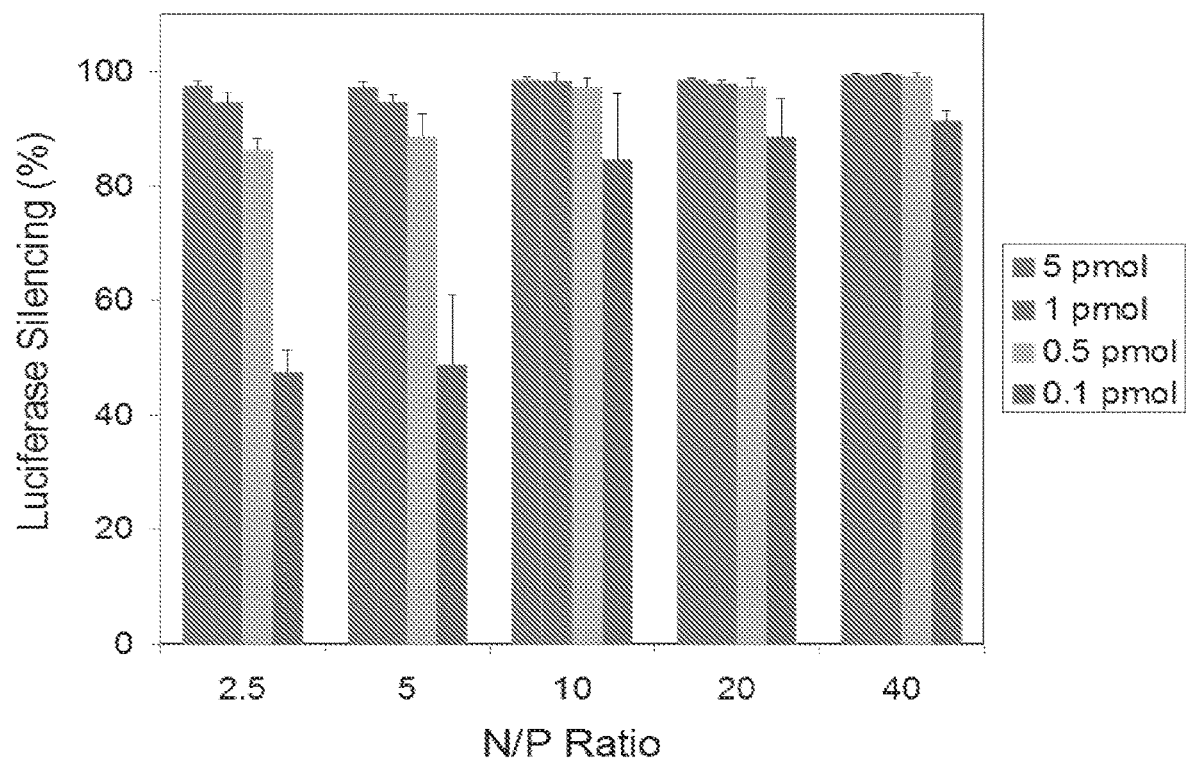
FIG. 9A: Encapsulation efficiency of DY547-siRNA loaded NPs with G0-C14 as the inner cationic lipid.
Figure 9B:
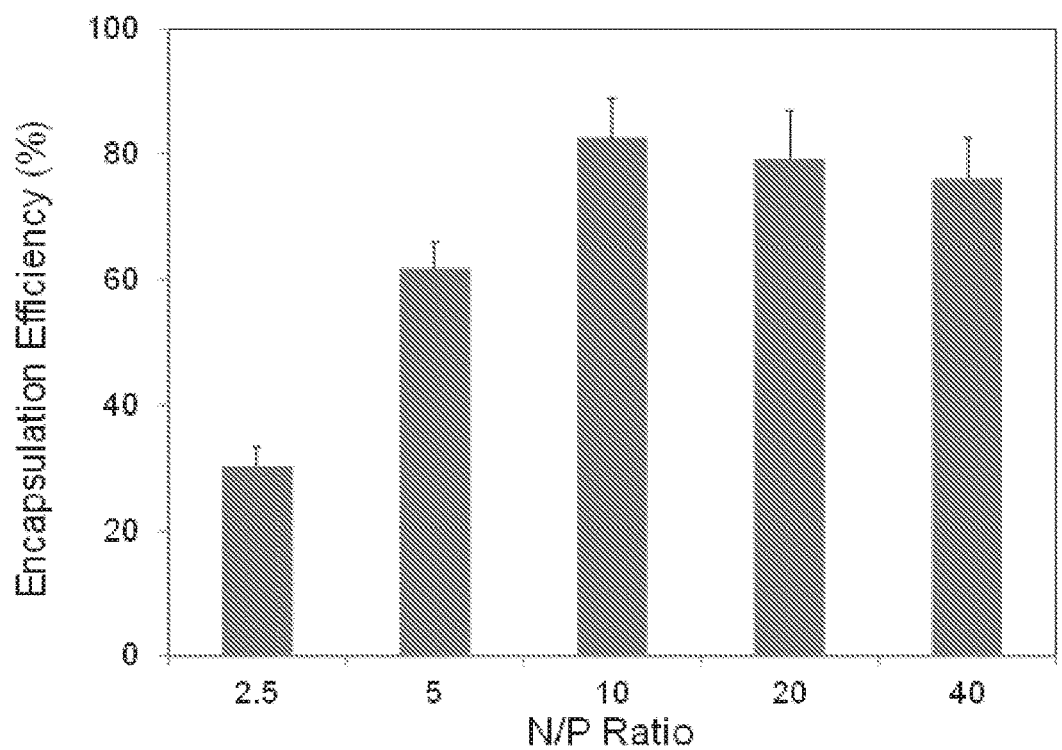
FIG. 9B: Luciferase silencing of Luc-Hela cells by NP(siLuc) with different N/P ratios. Luc-HeLa cells were transfected with NPs for 24 h and then washed with cell culture medium. The expression of firefly luciferase in Luc-HeLa cells was determined by Luciferase assay kit at 2 days after transfection. Results show that a decrease of encapsulation efficiency and luciferase silencing were observed with N/P ratio higher than 10/1. The N/P ratio of 10/1 was thus used for the preparation of siRNA NPs in all the following experiments.
Figure 10:
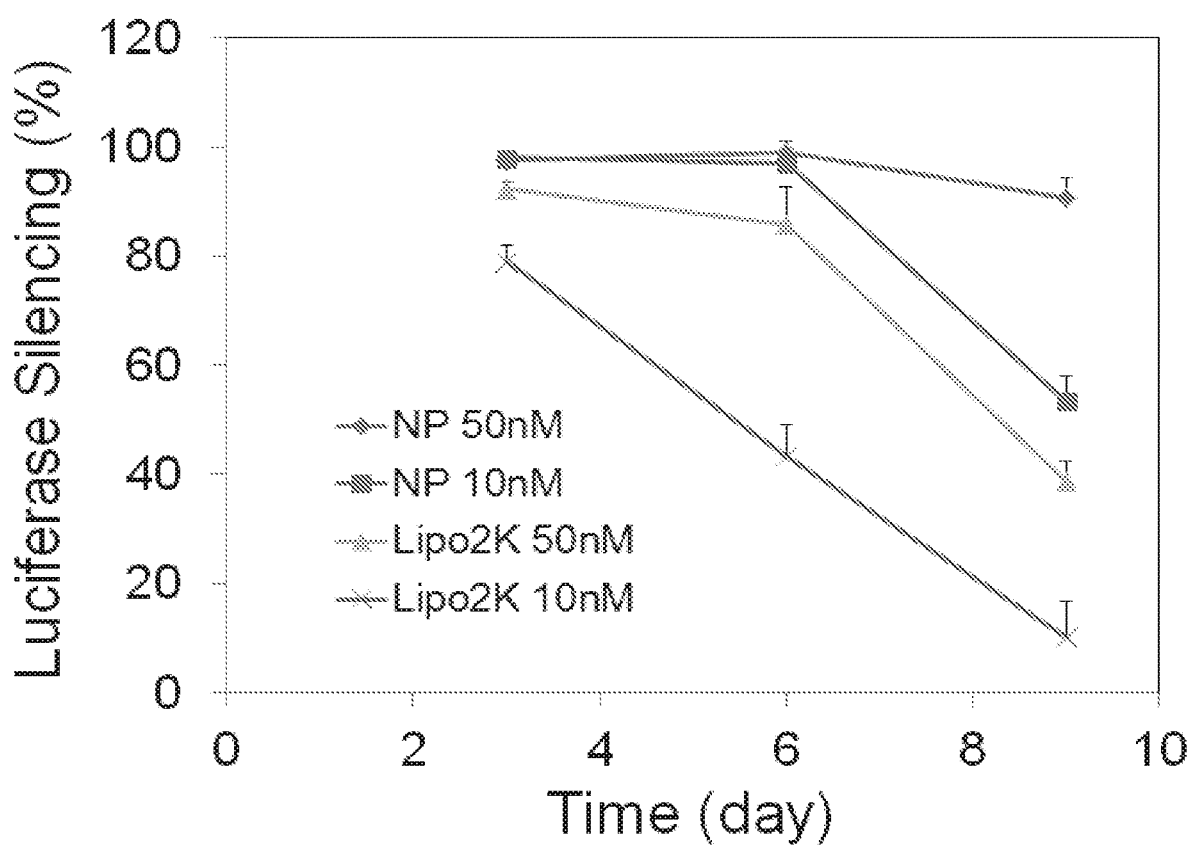
FIG. 10 shows sustained luciferase silencing after transfection with NP(siLuc) or Lipo2K-siLuc complexes. Cells transfected with NP(siLuc) exhibited slower recovery of luciferase expression compared with those transfected with Lipo2K. Around 91% silencing of luciferase expression could still be maintained at 9 days after transfection with NP with 50 nM siLuc, while only ~38.7% of silencing could be achieved with the Lipo2K counterpart. The excellent luciferase silencing at 9 days after transfection may be attributed to both the high silencing efficacy and the sustained siRNA release property. The NPs were prepared with G0-C14 cationic lipid with N/P ratio of 10/1. Luc-HeLa cells were transfected for 24 h and then washed with cell culture medium and further incubated. The expression of firefly luciferase in HeLa cells was determined by Luciferase assay kit at 3, 6 and 9 days after transfection.

Firefly luciferase expressed HeLa (Luc-HeLa) cells were used for optimizing and understanding the lipid-polymer hybrid NP platform for effective siRNA delivery. As demonstrated in the dose-responsive luciferase silencing experiments, the choice of cationic lipids (or lipid-like compounds) greatly influenced the silencing efficacy of the siRNA NPs (FIG. 8A, 8B, 9A). NPs with different cationic lipids exhibited varied effectiveness on luciferase silencing. NPs prepared with DAB-C12-8 and G0-C14 cationic lipid-like compounds exhibited significantly higher silencing efficacy compared with the commercial product Lipo2K. A highly potent NP formulation was prepared with G0-C14, which is much more effective than the commercial transfection agent lipofectamine 2000 (Lipo2K). Nearly complete (>95%) luciferase silencing was obtained with 10-50 nM siRNA, and >80% silencing can be achieved even at 1 nM. No apparent cytotoxicity was observed under these conditions. Lipid-PEG molecules exhibited little influence on luciferase silencing after 24 h of NP transfection with the Luc-HeLa cells. Moreover, G0-C14 NPs had longer sustained gene silencing compared to Lipo2K (FIG. 10). Over 90% silencing could still be maintained 9 days after transfection with G0-C14 NPs (50 nM siRNA), while only ~38% was silenced for Lipo2K under the same condition. In addition, the effect of N/P ratio, which was defined as the ratio of cationic amino groups (N) of G0-C14 to phosphate groups (P) of siRNA, was also examined for optimal encapsulation and silencing efficacy with the use of minimal amount of cationic lipids (FIG. 9A-9B). The N/P ratio of 10 was selected for following NP formulations unless otherwise specified.

Figure 16A:
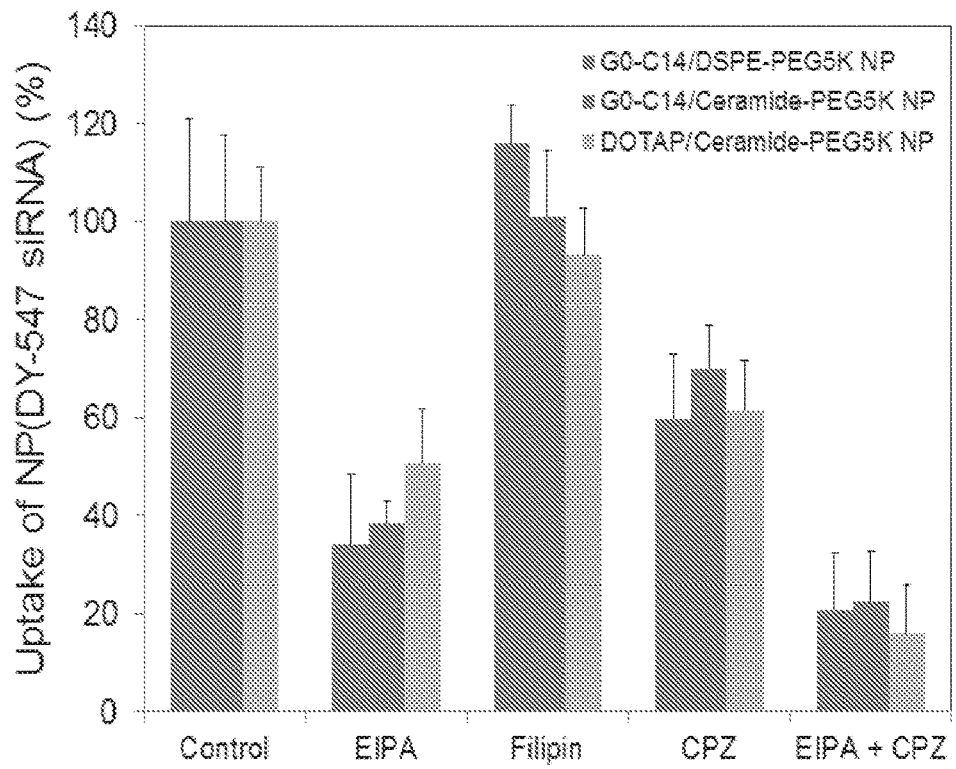
FIG. 16 shows the endocytosis pathway of the intracellular uptake of siRNA NPs in HeLa cells. (A) Percentage of NP uptake with the presence of different specific endocytic inhibitors as compared with untreated control. EIPA (5-(N-ethyl-N-isopropyl) amiloride), a macropinocytosis inhibitor; Filipin, a caveolae-mediated endocytosis inhibitor; and chlorpromazine, a clathrin-mediated endocytosis inhibitor, were used for this study. NP uptake was inhibited by both macropinocytosis and clathrin-mediated endocytosis inhibitors. (B) Co-localization (Pearson's correlation co-efficiency) of NP(DY547-siRNA) with specific dye-labeled endocytic probes. Dextran for macropinocytosis, cholera toxin B subunit for caveolae-mediated endocytosis, and transferrin for clathrin-mediated endocytosis were used for this study. (C) Confocal microscopy image of co-localization of NPs with endocytic probes. Red signal: DY547-siRNA NPs; Green signal: Alexa Fluor 488-labeled endocytic probes. 1st row: dextran, 2nd row: cholera toxin B subunit, 3rd row: transferrin; Light areas: overlay of DY547-siRNA with endocytic probes. Scale bar: 10 µm. For the uptake mechanism study with small molecule inhibitors, HeLa cells were first pre-incubated for 30 min with the small molecules, and then incubated with NP(DY547-siRNA) for 6 h with the inhibitors. For the uptake mechanism study with endocytic probes, experiments were conducted with addition of AF488-labeled probes (transferrin, cholera toxin B, and dextran) in the last 1 h of the 2 h NP incubation period. Subsequently, the cells were washed with PBS, fixed with 4% paraformaldehyde, and stained with Hoechst (2 µg/mL) for nuclei identification. Images were acquired on laser scanning confocal microscope (Leica SP5 X) or Inverted Fluorescence Microscope (Zeiss Axiovert 200) and analyzed using Fiji/Image-J software.
Figure 16B:
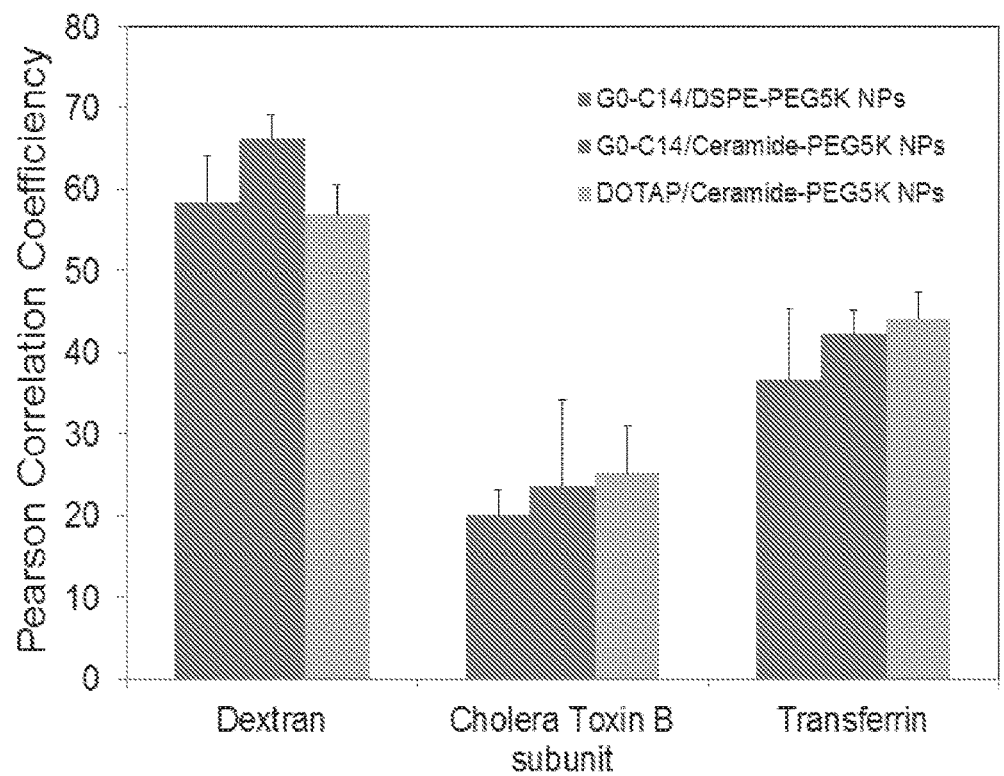
Figure 16C:
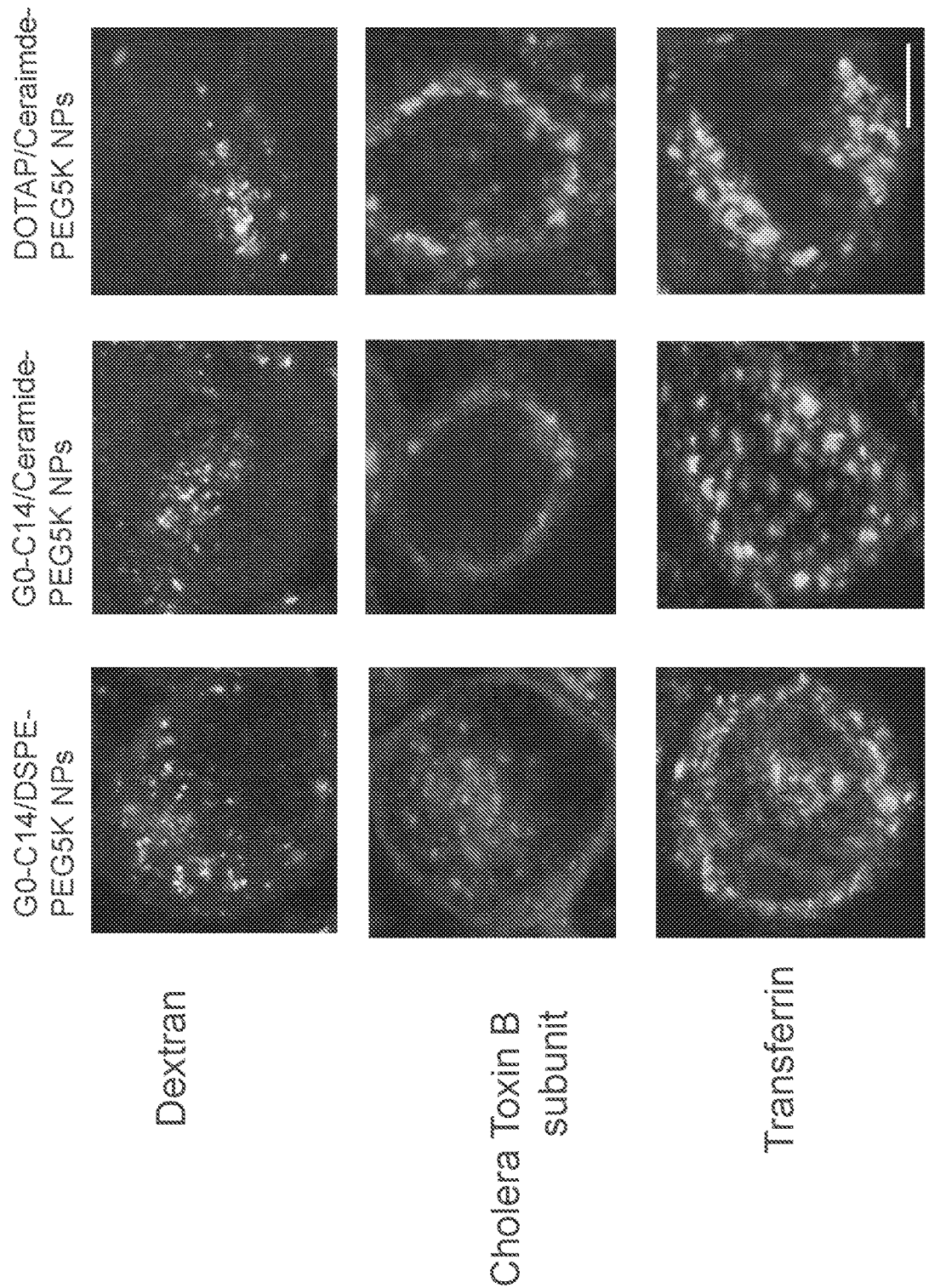
Figure 17A:
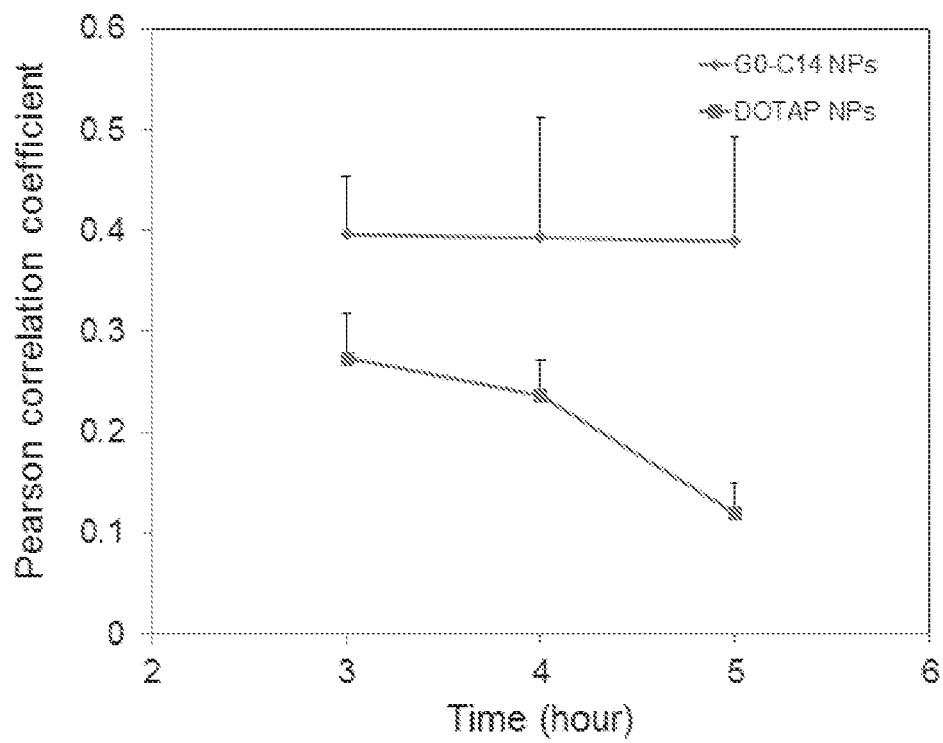
FIG. 17 shows the effect of cationic lipids on NP intracellular transportation. Intracellular trafficking of NP(DY547-siRNA) prepared with two different cationic lipids (G0-C14 and DOTAP) were tested in HeLa cells. (A) Quantification of co-localization (Pearson's correlation co-efficiency) of NP(DY547-siRNA) with early endosome marker (EEA1). (B) Quantification of co-localization (Pearson's correlation co-efficiency) of NP(DY547-siRNA) with late endosome and lysosome marker (LAMP1). (C-D) Confocal microscopy image of G0-C14 NPs or DOTAP NPs with EEA1. Red signal: NP(DY547-siRNA); Green signal: EEA1; Yellow signal: overlay of NP(DY547-siRNA) with EEA1. HeLa cells were first incubated with NP(DY547-siRNA) for 3 h (pulse), and then followed by 0-3 h chase by EEA1. Cells were then washed with PBS and fixed in 4% paraformaldehyde at room temperature for 15 min, followed by three washes with PBS for 5 min each. Subsequently, cells were incubated in blocking & permeabilization buffer for 60 min (PBS; 5% normal goat serum/0.2% Triton X-100). Cells or tissue were then incubated with primary antibodies for EEA1 or LAMP1 in dilution buffer (PBS; 1% BSA/0.2% Triton X-100) at 4° C. overnight. After rinsed three times with PBS, AF488 linked secondary antibodies were applied for 1 h at room temperature. The cell were then washed again with PBS for three times and mounted on slide with Prolong® gold antifade reagent (Cell Signaling) with Hoechst 33342 (Life technologies). Images were acquired with laser scanning confocal microscope (Leica SP5 X) and analyzed using Fiji/ImageJ software.
Figure 17B:
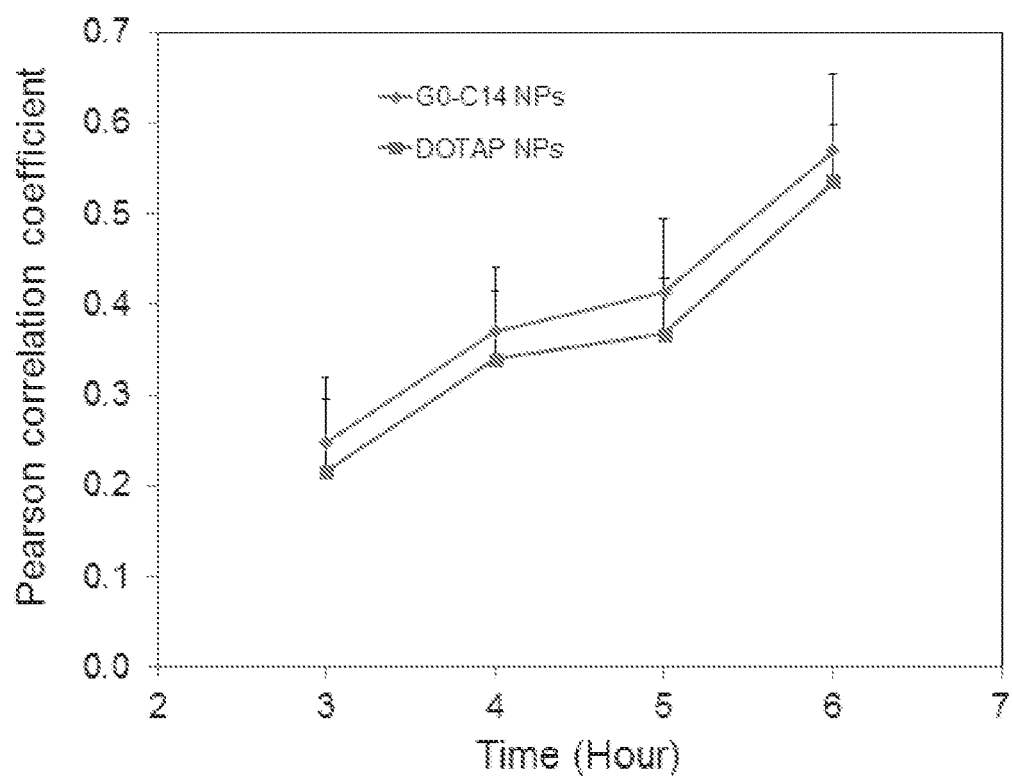

To understand the significant variation in silencing efficacy of the hybrid NPs prepared with different cationic lipids, the cellular behavior of two different NPs were investigated (G0-C14 vs. DOTAP). The two NPs exhibited similar surface charge (~0-5 mV), siRNA encapsulation efficiency and release profile, but the DOTAP NP was less effective in gene silencing than the G0-C14 one. The uptake of NPs in Luc-HeLa cells, which carried fluorophore DY547 labeled siRNA (DY547-siRNA), were compared. The two NPs featured very similar uptake kinetics and amounts in 24 hours (FIG. 13A, 13B). To study the mechanism for cellular internalization of the NPs, NP(DY547-siRNA) was incubated with Luc-HeLa cells in the presence of three specific endocytic inhibitors (5-N-ethyl-N-isopropamiloride (EIPA), filipin, or chlorpromazine (CPZ)) or dye-labeled probes (dextran, cholera toxin B, or transferrin), which represent three different endocytic pathways—macropinocytosis, caveolae- and clathrin-mediated endocytosis, respectively. The internalization pathway was indicated either by the reduction of NP uptake as a result of specific inhibitors or by the NP co-localization with the dye-labeled probes. In the inhibition study, a reduction of NP uptake in the range of about 50-65% upon the treatment of EIPA was observed, and a reduction in the range of about 30-40% upon treatment with CPZ for both G0-C14 and DOTAP NPs (FIG. 16A). Moreover, these two pathways may, to some extent, function independently, as higher inhibition of uptake (about 80%) was observed by co-incubating the two inhibitors (EIPA and CPZ) with NPs. Similarly, the probe co-localization experiment also confirmed the macropinocytosis and clathrin-mediated endocytosis pathways for cellular uptake of both NPs (FIG. 16B, 16C).

As no obvious difference was observed for the G0-C14 and DOTAP NPs in terms of cellular uptake kinetics and internalization pathways, their discrepancy of silencing efficacy could be attributed to the NP intracellular behavior. To monitor the various stages of NP transport through early endosomes, late endosomes and lysosomes, the time-dependent NP co-localization with specific markers was analyzed, including early endosome antigen 1 (EEA1) for early endosomes and lysosomal-associated membrane protein 1 (LAMP1) for late endosomes and lysosomes. NP(DY547-siRNA) was first incubated with the Luc-HeLa cells for 3 hours (pulse time). Then the cells were washed and maintained in fresh medium for another 0-3 hours (chase time), and fixed and immune-stained with EEA1 and LAMP1 antibodies. Interestingly, a higher correlation of G0-C14 NPs with EEA1 was observed than that of DOTAP NPs during the chase time period (FIG. 17A-17D), indicating the internalized NPs might influence the progression of early endosomes. One mechanistic study using cationic lipid NPs also demonstrated the delay in maturation of early endocytic compartment, and suggested that the escape of siRNA NPs mainly occurred in a moderately acidic, hybrid early-late endosomal compartment (Gilleron, J., et al. Image-based analysis of lipid nanoparticle-mediated siRNA delivery, intracellular trafficking and endosomal escape. *Nat. Biotechnol.* 31, 638-646 (2013)).

Example 2B siRNA Delivery to Venular Endothelium

A critical feature in the pathogenesis of inflammation is the ability of endothelial cells (ECs) to support tissue-specific multi-step adhesion cascades to recruit blood-borne leukocytes to the extravascular compartment. Leukocyte migration is essential for autoimmune and inflammatory diseases that can target virtually any tissue, including the intestine. It has been shown that leukocyte interactions with microvessels are restricted to postcapillary and collecting venules, whereas capillaries and arterioles do not support significant leukocyte adhesion. Therefore, by targeting venular endothelium, leukocyte recruitment can be blocked. The confocal fluorescence images in FIG. 29 illustrate that our siRNA NPs can effectively target venues in the adipose tissue.

Example 2C

Fluorescent Particles

Figure 34D:
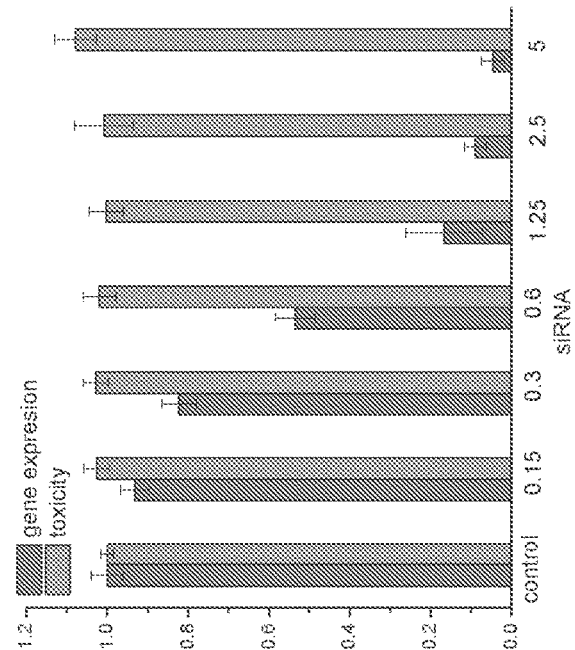
Figure 34C:
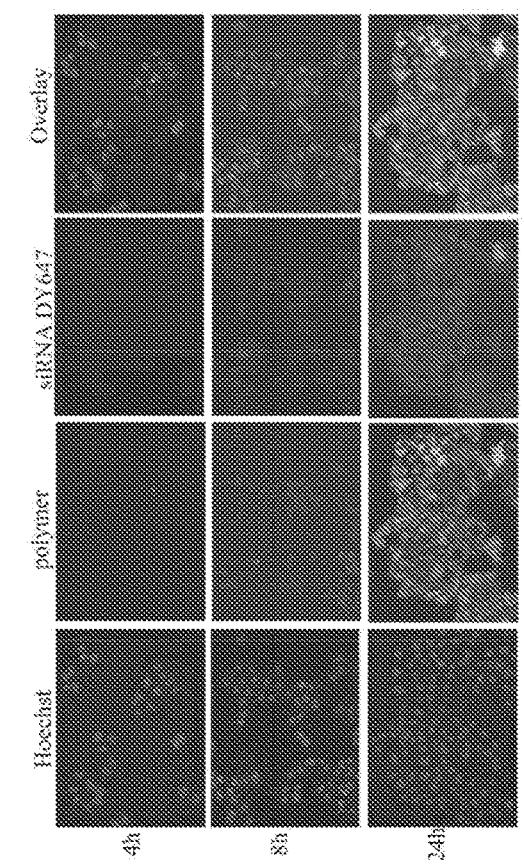
Figure 34E:
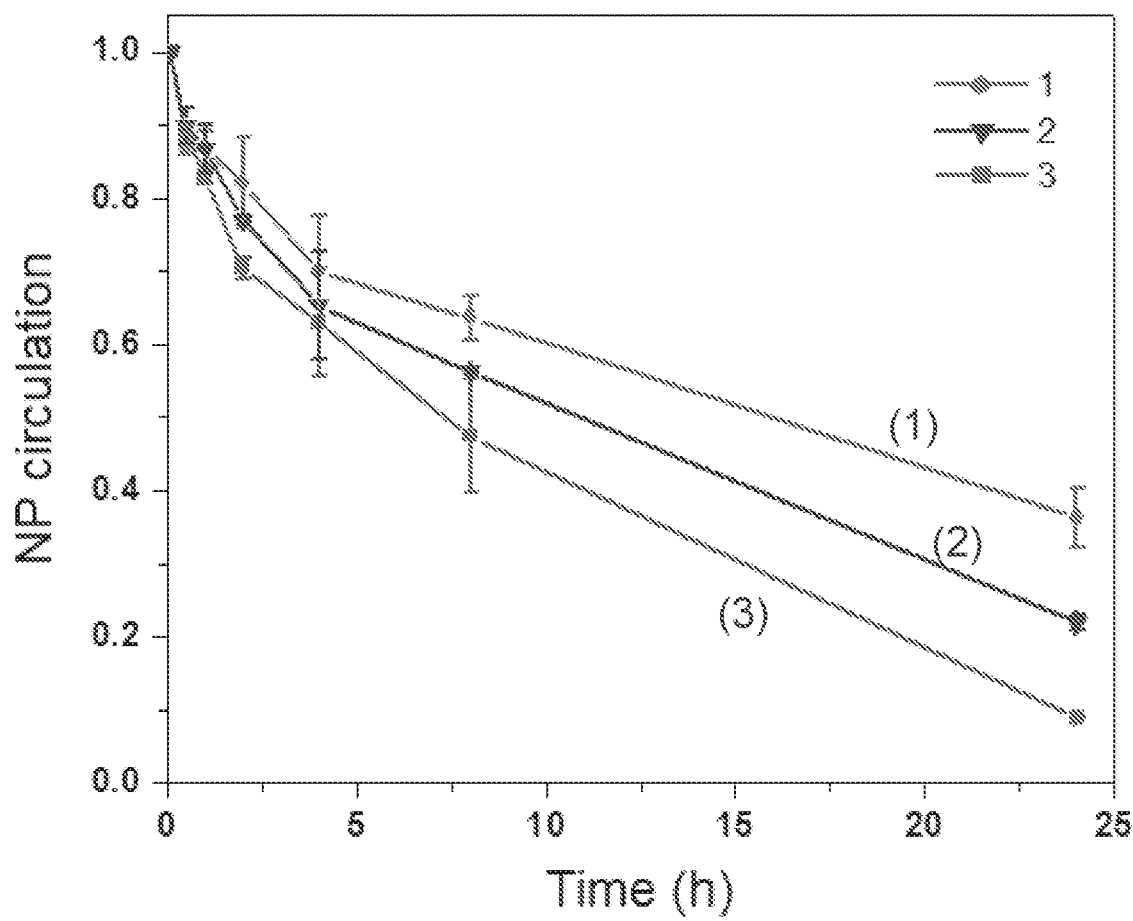

FIG. 34C demonstrates that the uptake of both polymer NPs and siRNAs of Example 1F can be imaged simultaneously. In addition to fluorescence imaging, these NPs also show effective gene silencing in cancer cells (FIG. 34D). More impressively, the fluorescent PCPDTBT-siRNA NPs exhibit extremely impressive circulation profiles in normal mice. As can be seen in FIG. 34E, the NP #1 has ~40% left in blood 24 h post intravenous injection.

Example 3

Effect of Lipid-PEG on Systemic siRNA Delivery

Figure 19A:
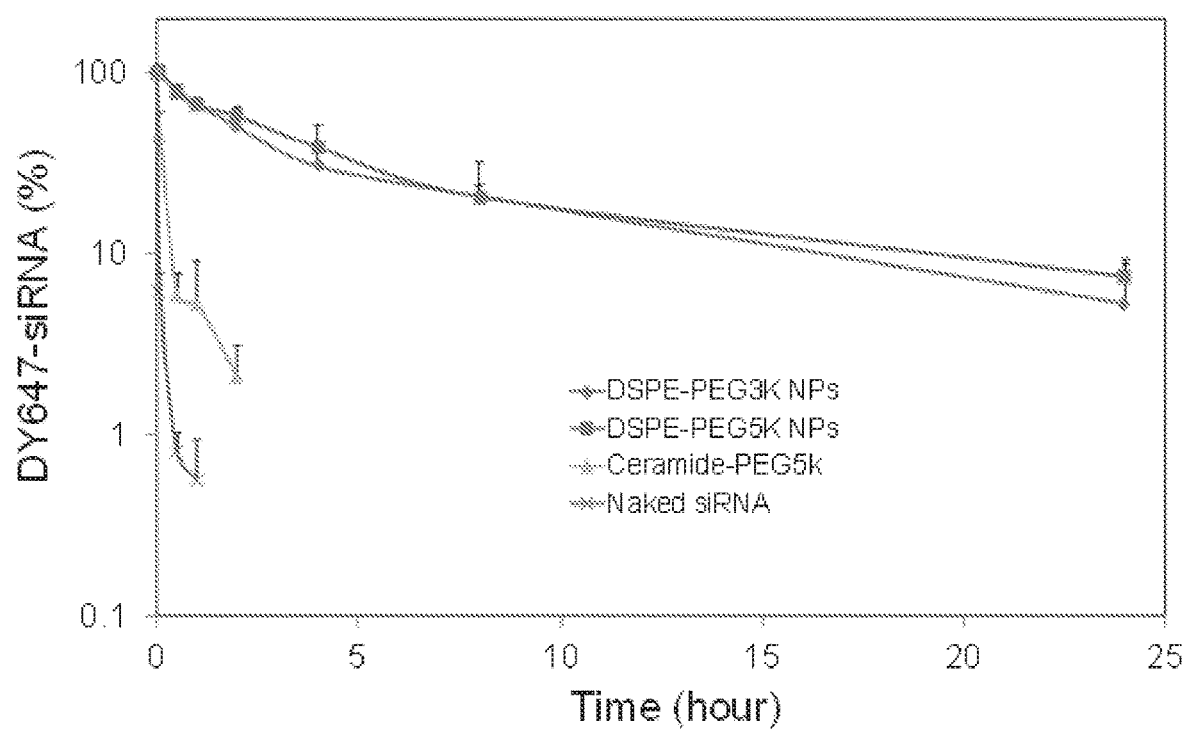
FIG. 19 shows in vivo pharmacokinetics. (A) Circulation profiles of different DY647-siRNA NPs and naked DY647-siRNA in BALB/c mice after intravenous injection. (B) Area under curve and (C) circulation half-life ($t_{1/2}$) of different DY647-siRNA NPs and naked DY647-siRNA.
Figure 19B:
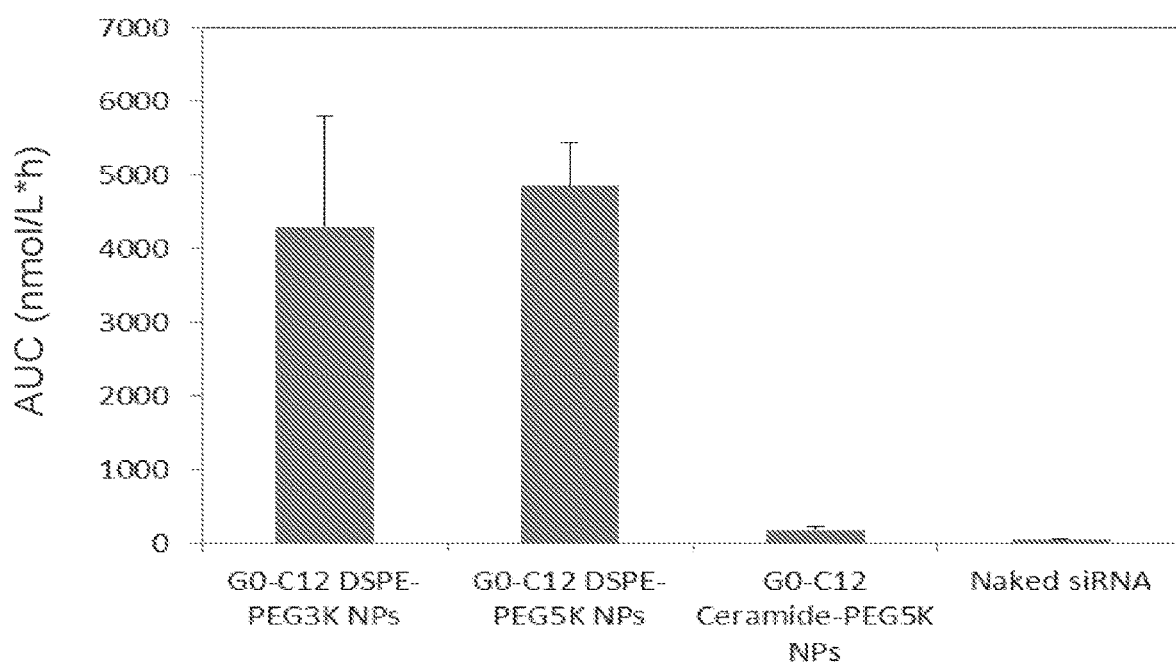
Figure 19C:
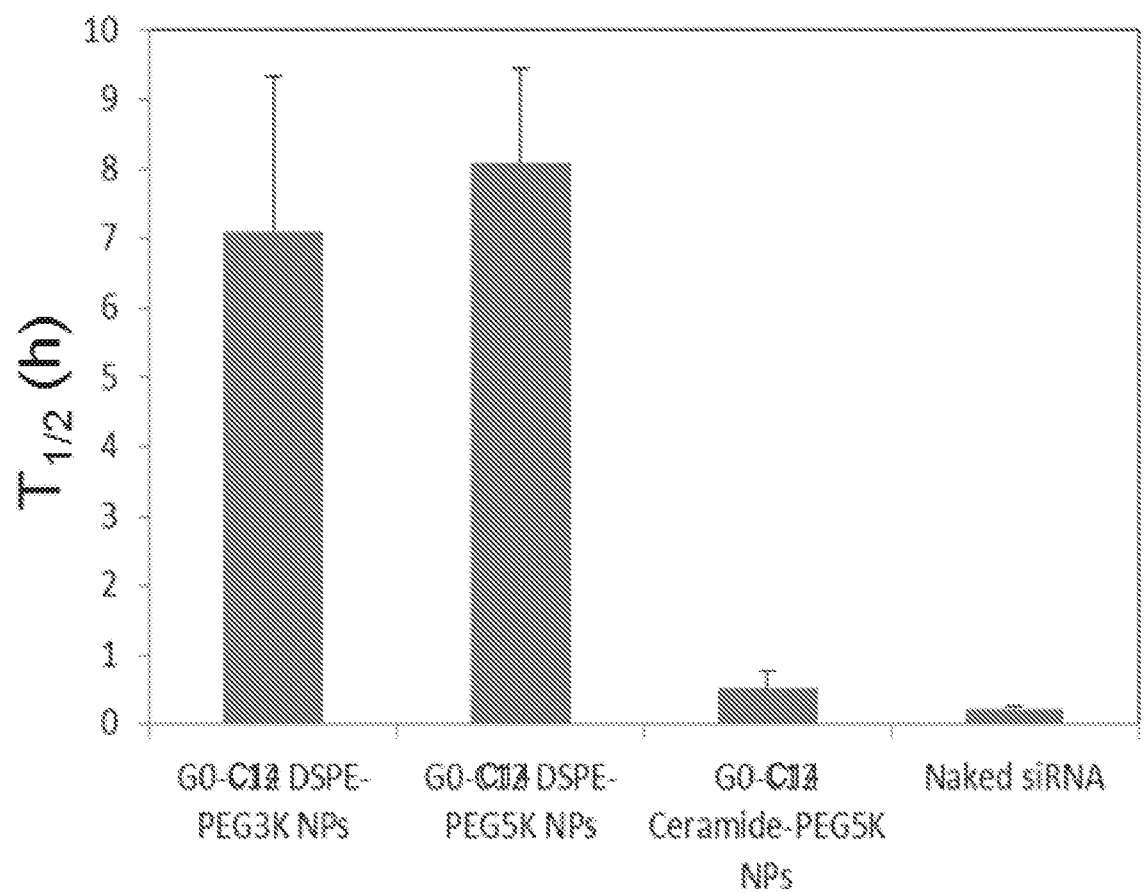
Figure 20B:
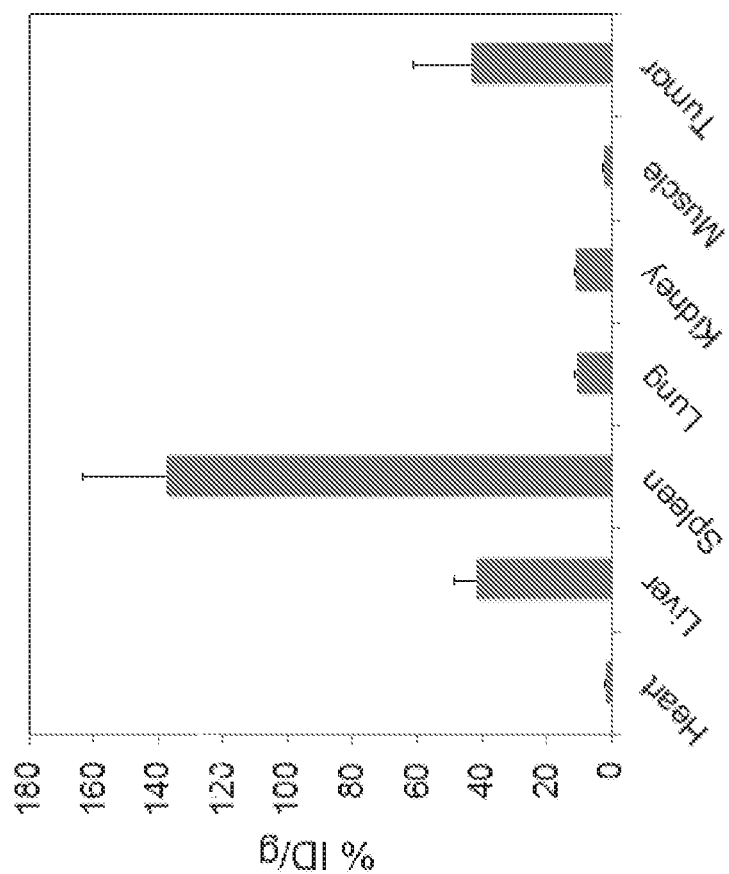
FIG. 20 shows in vivo biodistribution. (A) Representative tissues of mice bearing NCI-H460 xenografts at 24 h after intravenous injection with NP(DY677-siRNA) or naked DY677-siRNA. The florescence intensity is shown in pseudo-color. (B) Biodistribution quantification of NP(siRNA). (C) Whole-animal fluorescence imaging at 24 h after intravenous injection of NP(DY677-siRNA) or naked DY677-siRNA.
Figure 20A:
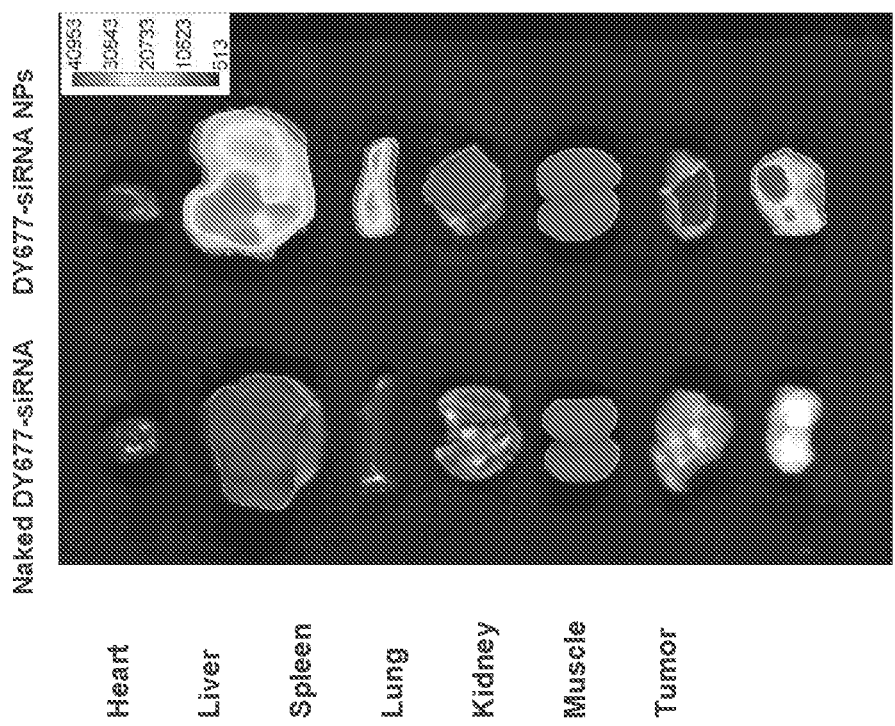
Figure 20C:
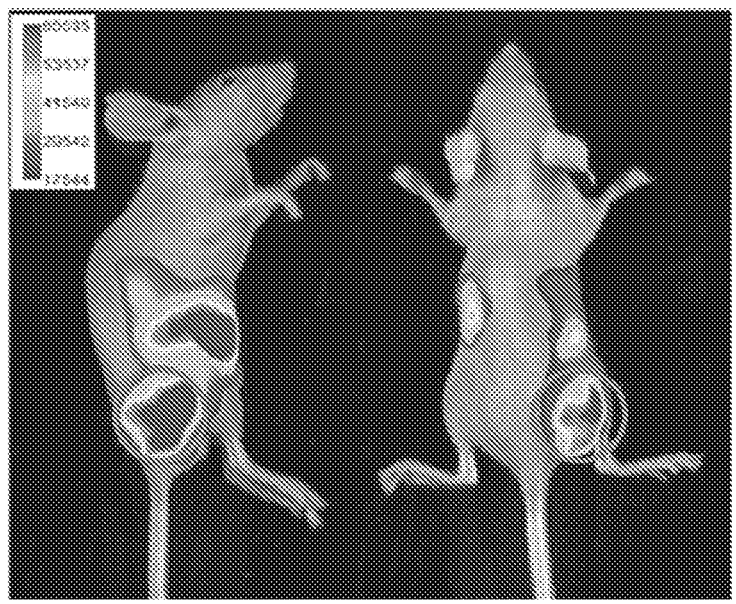
Figure 20C:

To evaluate the in vivo performance of these hybrid NPs for siRNA delivery, the pharmacokinetics (PK) was examined by injecting NP(DY647-siRNA) to normal BALB/c mice through the tail vein. Three different G0-C14 NP formulations were compared versus naked siRNA, with ceramide-PEG5K, DSPE-PEG5K, or DSPE-PEG3K as the surface lipid-PEG. As can be seen in FIG. 19A, naked siRNA was rapidly cleared from the blood circulation within 30 min. Ceramide-PEG5K NPs extended the circulation of siRNA with a half-life ($t_{1/2}$) of about 30 min. Both DSPE-PEG5K and DSPE-PEG3K NPs exhibited an improved circulation property with $t_{1/2}$ of about 7-8 h. Accordingly, DSPE-PEG NPs increased the area under the curve (AUC) by about 100-fold as compared to naked siRNA (FIG. 19B, 19C). Next, the NP biodistribution (BioD) and tumor accumulation upon systemic administration in mice bearing subcutaneous NCI-H460 tumor were determined. Xenografted nude mice were intravenously (IV) injected with NP(DY677-siRNA) or naked DY677-siRNA, and 24 hours later, organs and tumors were harvested. Long-circulating DSPE-PEG5K NPs demonstrated high tumor accumulation in the NCI-H460 xenograft (FIG. 20A-20C), while ceramide-PEG5K NPs and naked siRNA exhibited low or negligible signal in tumor. Quantification analysis showed a 10-fold higher accumulation of DSPE-PEG5K NPs per gram of tumor tissue than ceramide-PEG5K NPs. This high tumor accumulation of DSPE-PEG NPs could be attributed to the small size and long blood circulation of the NPs, both of which may facilitate the extravasation of NPs through leaky tumor microvasculature (Bertrand, N., Wu, J., Xu, X., Kamaly, N. & Farokhzad, O. C. Cancer nanotechnology: the impact of passive and active targeting in the era of modern cancer biology. *Adv. Drug Deliv. Rev.* 66, 2-25 (2014); Alexis, F., Pridgen, E., Molnar, L. K. & Farokhzad, O. C. Factors affecting the clearance and biodistribution of polymeric nanoparticles. *Mol. Pharm.* 5, 505-515 (2008)).

Figure 11A:
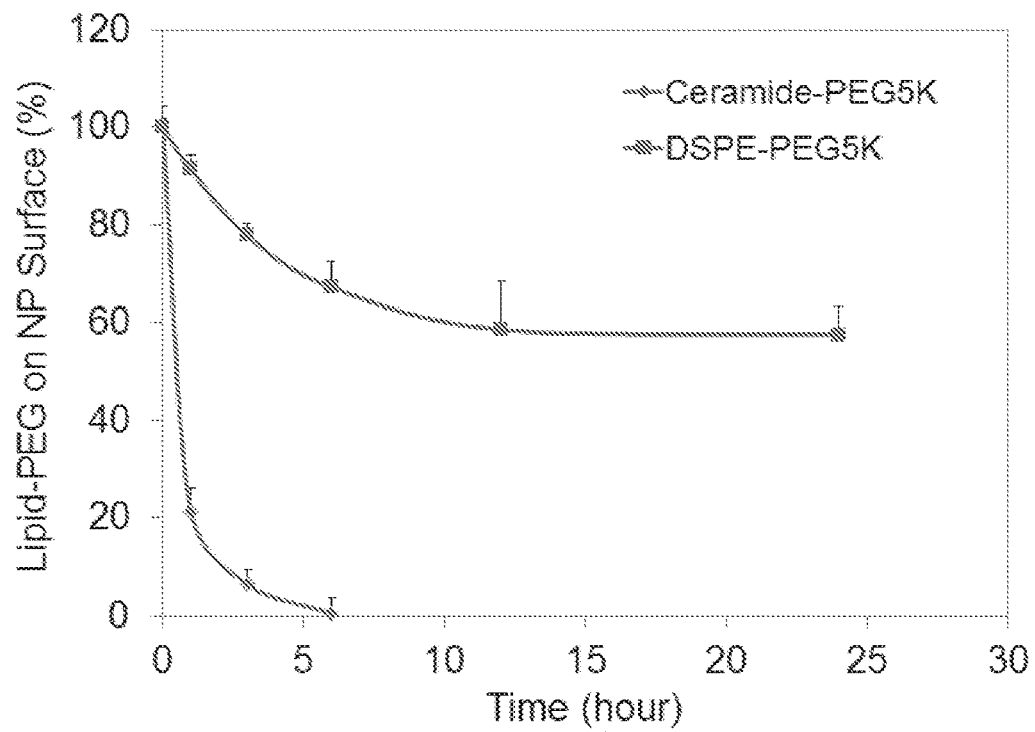
FIG. 11 shows the lipid-PEG dissociation kinetics and change of zeta potential of two different NPs (ceramide-PEG NP vs. DSPE-PEG NP) as a function of time. (A) The dissociation of lipid-PEG from NPs in simulated serum (4% serum albumin) was studied using a modified methods based on spectrophotometric measurement of a complex formed between PEG and barium iodide. NPs were incubated in simulated serum at 37° C. At a predetermined time point, NP suspension was ultra-centrifuged, washed with DI H2O, and resuspended. Then 100 µL of NP solution (1.25 mg/mL at polymer weight) was mixed with 100 µL of DMSO, 20 µL of $BaCl_2$ (5%) and 20 µl of $I_2$ solution (0.1 N). Calibration curve was prepared with corresponding lipid-PEG solution with same concentration of PLGA (1.25 mg/mL) and G0-C14 (0.125 mg/mL). After incubation at room temperature for 15 min, absorbance at 535 nm was measured on the microplate reader. (B) For zeta potential measurement, 40 µL of NPs (5 mg/mL) was incubated in 4% serum albumin at 37° C. At a predetermined time point, NP suspension was ultra-centrifuged, washed with pure H2O and ultra-centrifuged again. The pellet was re-suspended for zeta potential measurement (Brookhaven Instruments Corporation).
Figure 11B:
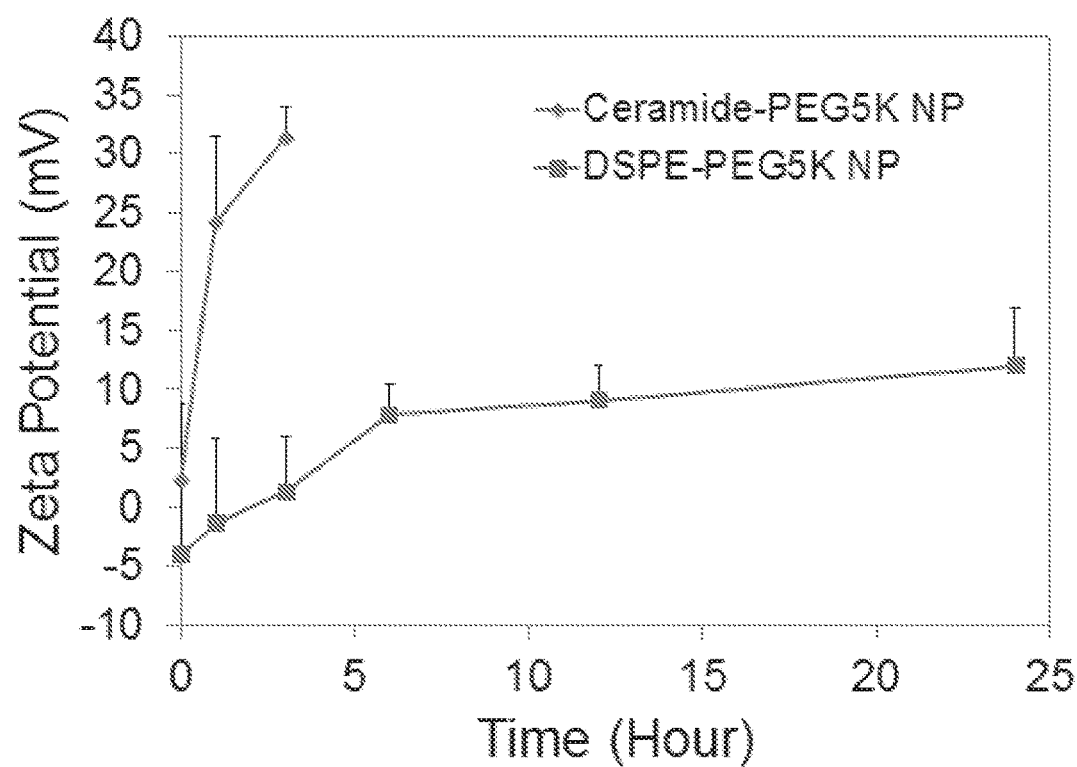

To explain the drastic difference in PK/BioD between DSPE-PEG and ceramide-PEG NPs, the effect of lipid-PEG on NP properties and behavior was systematically studied. According to the quantitative analysis of PEG molecules (Cheng, T. L., Chuang, K. H., Chen, B. M. & Roffler, S. R. Analytical measurement of PEGylated molecules. Bioconjug. Chem. 23, 881-899 (2012)), both NPs carried a similar amount of lipid-PEG on the particle surface, at about 9.5 weight % compared with the weight of the PLGA polymer. The dissociation kinetics of DSPE-PEG5K and ceramide-PEG5K were measured from respective NPs in the presence of serum albumin that is abundant in blood and can bind with diacyl lipids (Liu, H., et al. Structure-based programming of lymph-node targeting in molecular vaccines. Nature 507, 519-522 (2014)). FIG. 11A demonstrated not only the dissociation of both lipid-PEGs, but much faster release of ceramide-PEG5K than DSPE-PEG5K from NPs. After 6 hours, the ceramide-PEG5K on NP surfaces dwindled below the detection limit. The rapid detachment of ceramide-PEG5K, as compared to DSPE-PEG5K, may be attributed to its shorter and unsaturated alkyl chain, which may lead to lower phase transition temperature and higher fluidity of the lipid-PEG (Romberg, B., Hennink, W. E. & Storm, G. Sheddable coatings for long-circulating nanoparticles. Pharm. Res. 25, 55-71 (2008); Cevc, G. How membrane chain-melting phase-transition temperature is affected by the lipid chain asymmetry and degree of unsaturation: an effective chain-length model. Biochemistry 30, 7186-7193 (1991)), and fewer hydrophobic interactions with the PLGA core. Owing to the dissociation of lipid-PEGs and exposure of PLGA/cationic lipid/siRNA hybrid core, the NP surface charge (or zeta potential) also changed over time (FIG. 11B). Both DSPE-PEG5K and ceramide-PEG5K NPs were close to neutral charge initially. By incubation with albumin, the surface charge increased from 2.2 mV to 31.4 mV in 3 hours for ceramide-PEG5K NPs, and from −4.0 mV to 11.9 mV for DSPE-PEG5K NPs in 24 hours. The trend of surface charge change is consistent with the lipid-PEG dissociation kinetics.

Figure 14A:
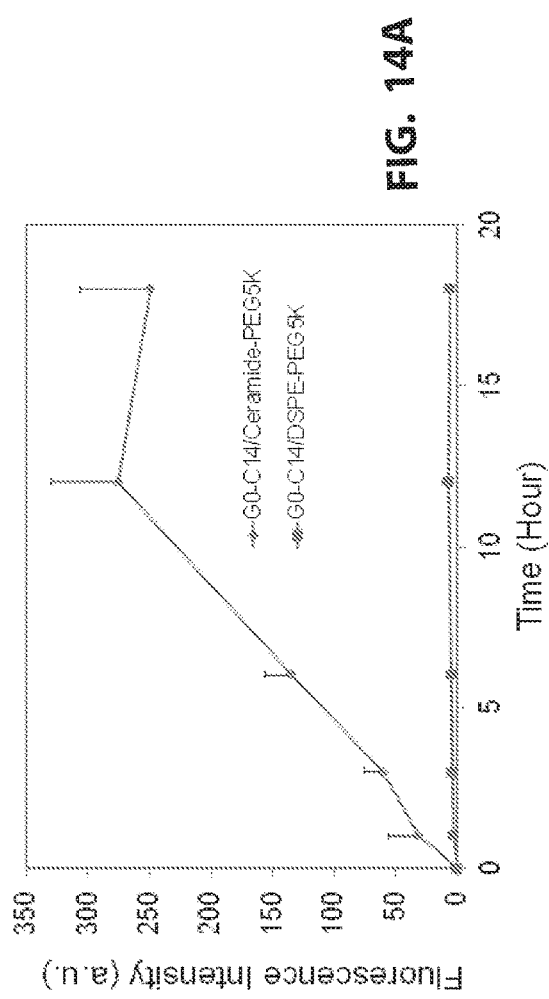
FIG. 14 shows NP uptake kinetics in RAW264.7 macrophage. (A) Quantification of cellular uptake kinetics of NPs prepared with two different lipid-PEGs (Ceramide-PEG5K vs. DSPE-PEG5K) in macrophage cells (RAW264.7). (B) Examples of uptake images at 3 h, 12 h, and 18 h. For the uptake kinetics study, RAW264.7 cells were incubated with NP(DY547-siRNA) for different time periods (1 h, 3 h, 6 h, 12 h, and 18 h), washed with PBS, fixed with 4% paraformaldehyde, and stained with Hoechst (2 µg/mL) for nuclei identification. Images were acquired on inverted fluorescence microscope (Zeiss Axiovert 200) and analyzed using Fiji/Image-J software.
Figure 14B:
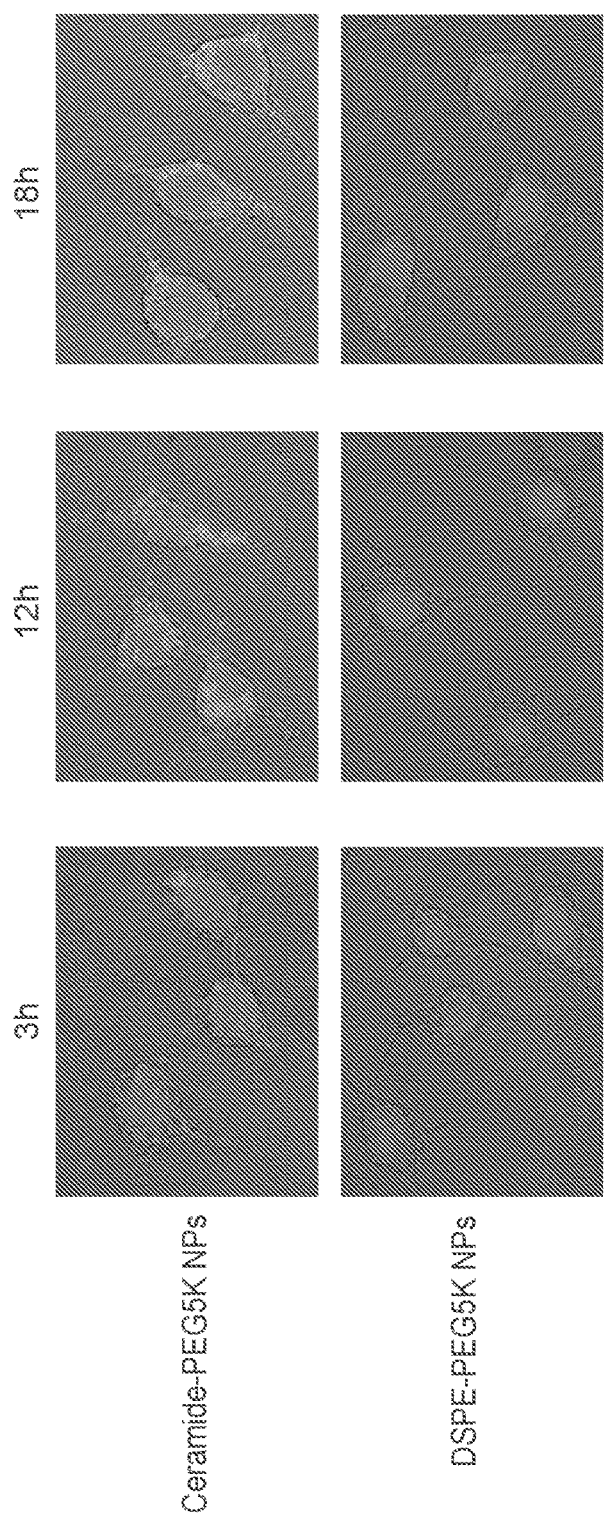

We then investigated the uptake kinetics of these two NPs in macrophage cells (RAW264.7), which represent a major cell type in MPS system for clearance of exogenous NPs. As shown in FIG. 14A-14B, ceramide-PEG5K NPs experienced much faster and higher cellular uptake than DSPE-PEG5K NPs, presumably due to the higher opsonization mediated by rapid change of surface properties of ceramide-PEG5K NPs. This in turn explained the much shorter circulation life of ceramide-PEG NPs in blood. In parallel, the effect of lipid-PEG on NP uptake by tumor cells (Luc-HeLa) was tested (FIG. 12A-12B). Similarly, rapid tumor cell uptake was noticed with ceramide-PEG5K NPs after 1 hour incubation, while DSPE-PEG5K NPs exhibited slow uptake within the first 6 hours of incubation followed by accelerated internalization. This is also correlated with the lipid-PEG release profiles in FIG. 11A. There was no observed difference in the endocytosis pathways for these two NPs (FIG. 16A-16C). The difference in uptake kinetics can also affect the gene silencing in tumor cells. Upon 6-hour incubation with Luc-HeLa cells, DSPE-PEG5K NPs were less effective for luciferase silencing compared with ceramide-PEG NPs. When the incubation time was extended to 24 hours, these two NPs exhibited comparable silencing efficacy.

Figure 15A:
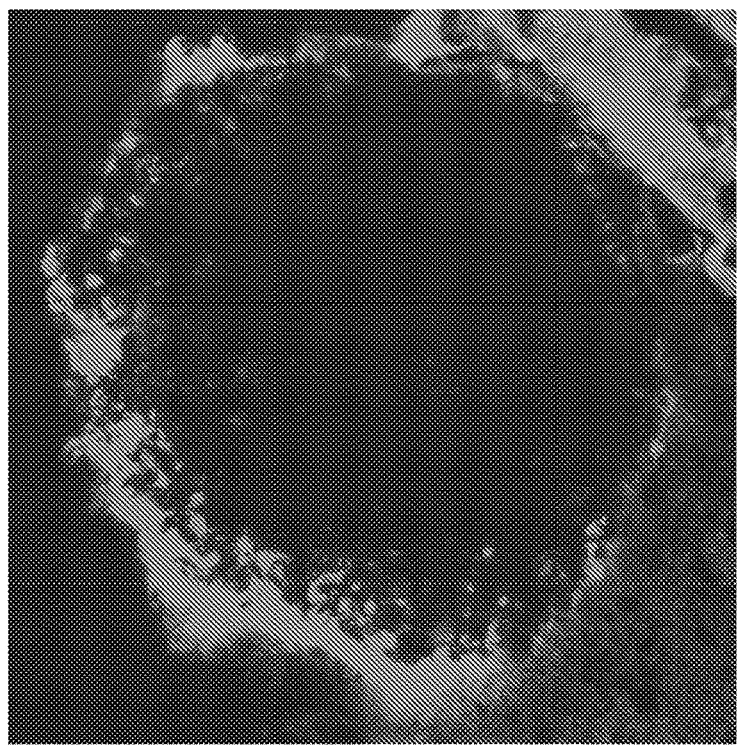
FIG. 15 shows diffusion of ceramide-PEG NPs (A) and DSPE-PEG NPs (B) in 3D in vitro tumor spheroid. For spheroid generation, 200 µl/well of A549 cell suspensions at densities 1×104 cells/mL with 2.5% Matrigel were dispensed into ULA 96-well round-bottomed plates (Corning B.V. Life Sciences). Cells were cultured for 4 days until a three-dimensional spheroid were formed. The spheroid was then incubated with NP(DY547-siRNA) with DSPE-PEG vs. ceramide-PEG for 24 h, and then washed with PBS and fixed with 4% paraformaldehyde. Images were acquired with laser scanning confocal microscope (Zeiss LSM510).
Figure 15B:
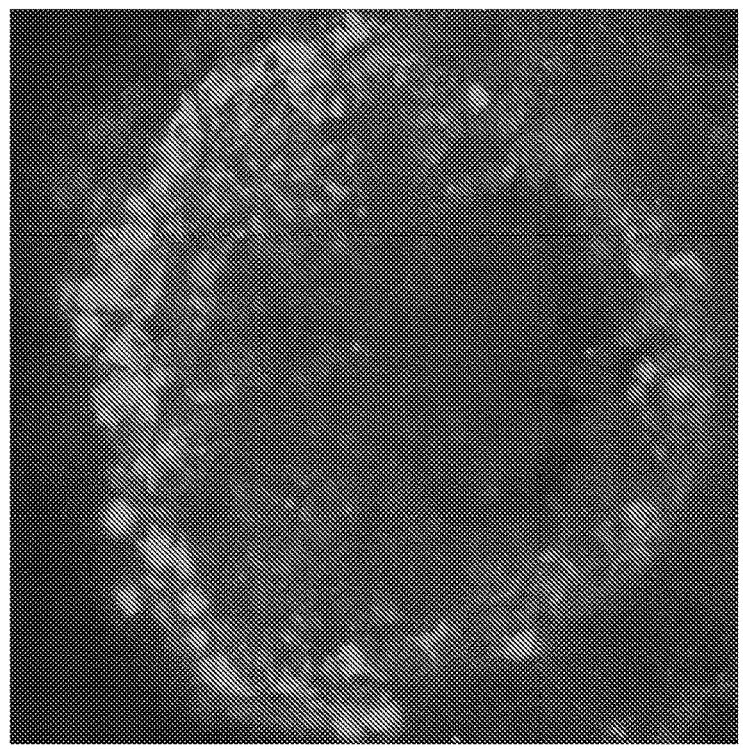

Furthermore, the tumor penetrability of these two NPs was also compared, which is another major factor in determining gene silencing efficacy in tumor (Jain, R. K. & Stylianopoulos, T. Delivering nanomedicine to solid tumors. Nat. Rev. Clin. Oncol. 7, 653-664 (2010)). The NP diffusion and distribution was evaluated using an in vitro 3D tumor spheroid of A549 cells. Deep penetration of DSPE-PEG NPs was observed in the 3D tumor matrix by confocal fluorescence microscopy, while majority of ceramide-PEG NPs were accumulated on the boundary of this tumor model (FIG. 15A-15B). This result indicates that slow detachment of DSPE-PEG could be compatible with NP penetration throughout tumor extracellular matrix, as compared to fast dissociation of ceramide-PEG.

Example 4

In Vitro Validation

Example 4A

PHB1-Targeted NSCLC Treatment

With the long circulating DSPE-PEG5K/G0-C14 NP for siRNA delivery, a potential therapeutic target PHB1 was assessed for NSCLC treatment. NSCLC accounts for around 85% of lung cancer that remains the leading cause of cancer-related mortality, and approximately 70% NSCLC subjects are at advanced stages of the disease at the time of diagnosis. PHB1 is a 32 kDa protein that belongs to a highly conserved protein family containing the stomatin/prohibitin/flotillin/HflK/C domain (also known as the PHB domain) found in organisms ranging from yeast to humans, and has been implicated in aging, obesity, diabetes, cancer and inflammatory diseases (Theiss, A. L. & Sitaraman, S. V. The role and therapeutic potential of prohibitin in disease. Biochim. Biophys. Acta 1813, 1137-1143 (2011)).

Figure 18A:
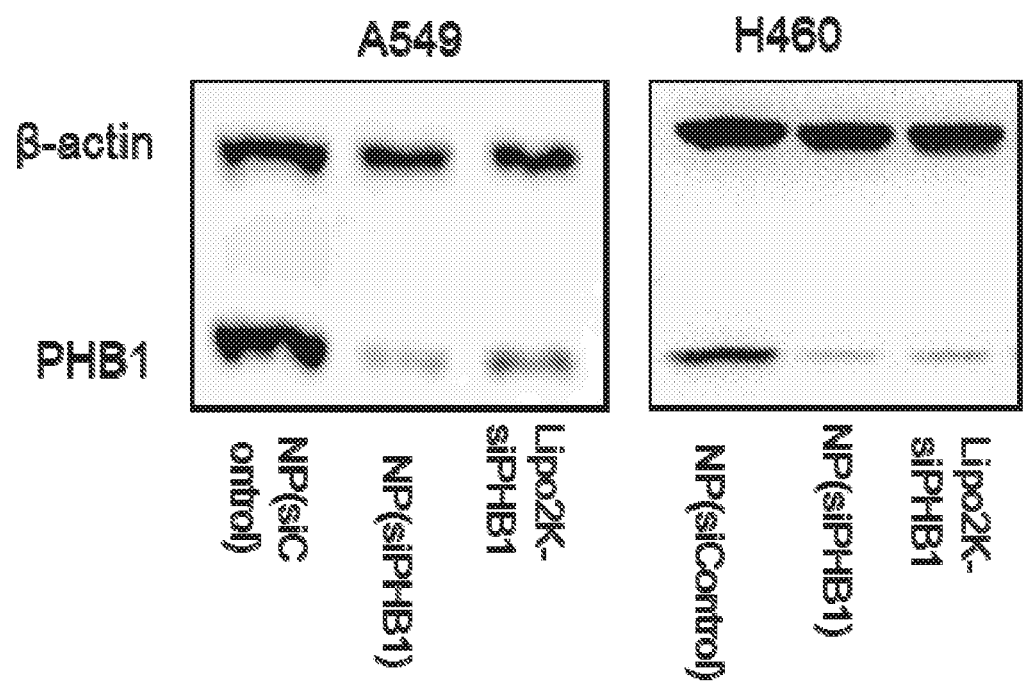
FIG. 18 shows in vitro PHB1 silencing and cell proliferation. (A) Western-blot analysis of Prohibitin1 (PHB1) protein level in A549 or NCI-H460 lung cancer cells after transfected with NP(siPHB1) or Lipo2K-siPHB1 complexes. More effective PHB1 silencing can be achieved with NP(siPHB1) vs. Lipo2K complexes. (B) Immunofluorescence image of PHB1 in NCI-H460 cells after transfected with NP(siPHB1) or Lipo2K-siPHB1 complexes. Red: β-actin; Green: PHB1; and Blue: nucleus. (C-D) Cell proliferation of A549 or NCI-H460 cells after transfected with NP(siPHB1) or NP(siControl). NP(siPHB1) can effectively inhibit the proliferation of A549 and NCI-H460 cells in vitro, while no obvious cellular toxicity was observed with NP(siControl).
Figure 18B:
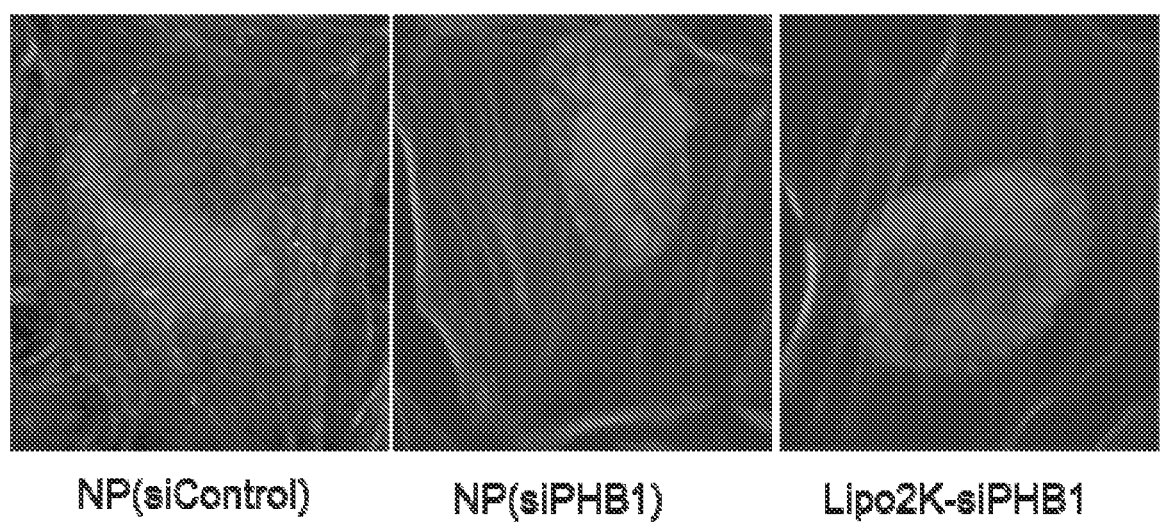
Figure 18C:
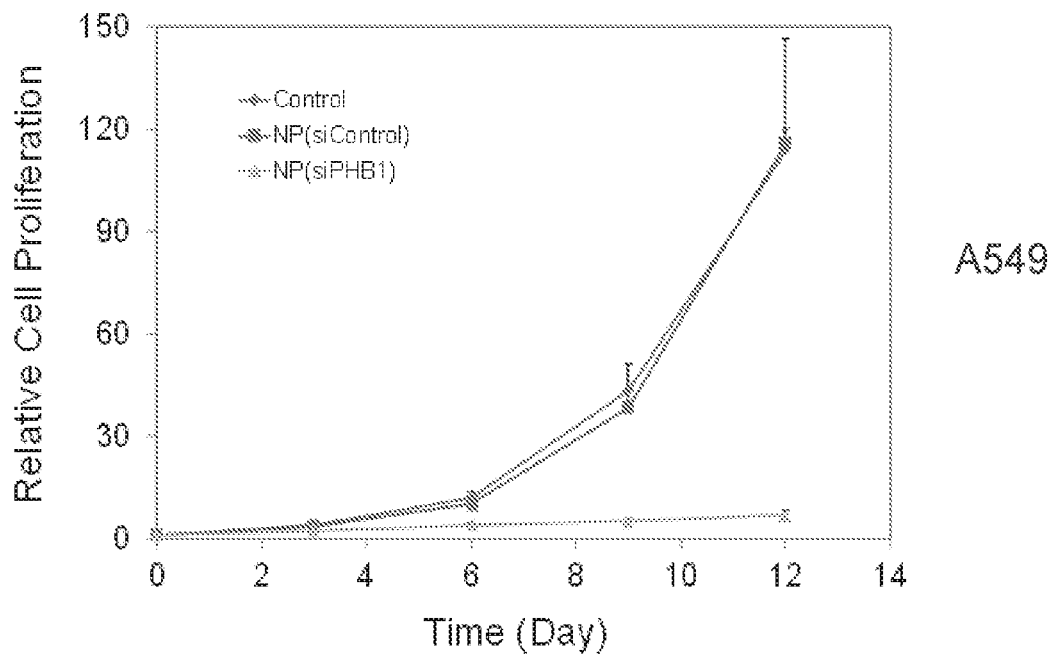
Figure 18D:
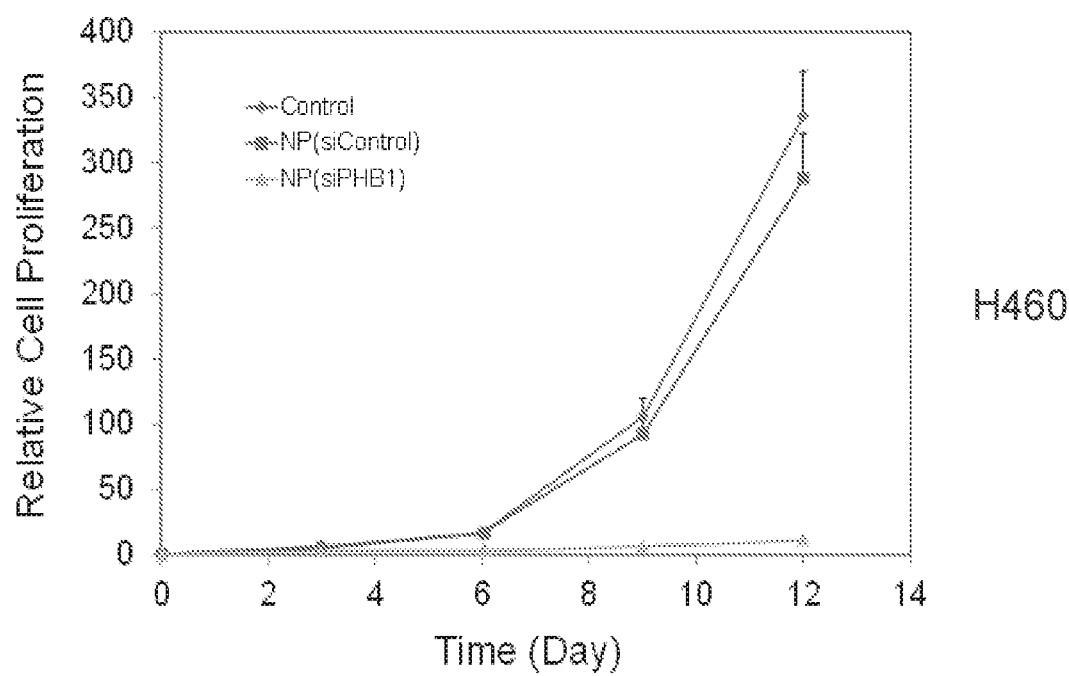

In cell proliferation analysis, NP(siPHB1) treatment for 6 hours resulted in drastic inhibition of cell proliferation as compared to NP(siControl) and no treatment control (FIG. 18C-18D). The cell number in the NP(siPHB1) group was only about 4% of that in the control groups after 12 days.

Example 4B

Mouse Macrophage Study with microRNA

Figure 32A:
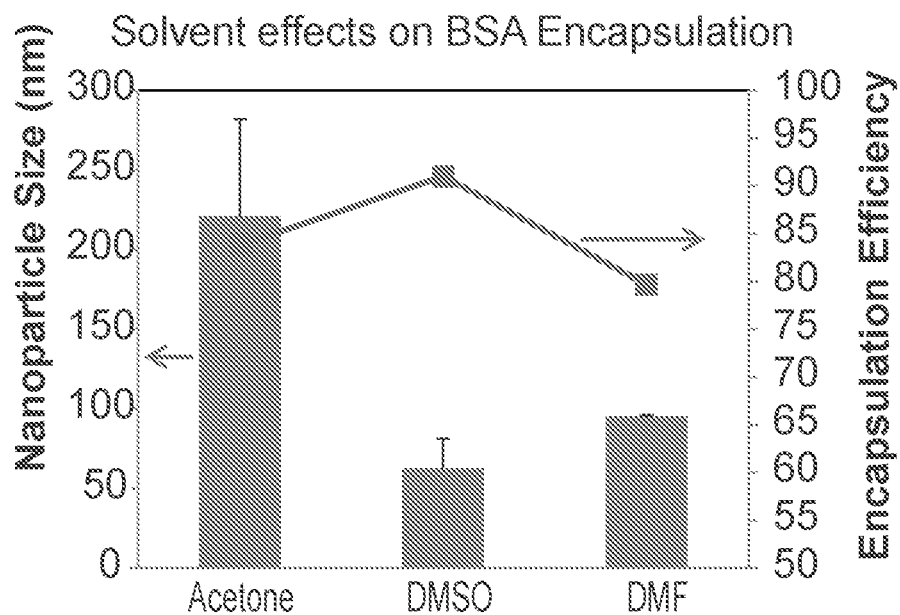
Figure 32B:
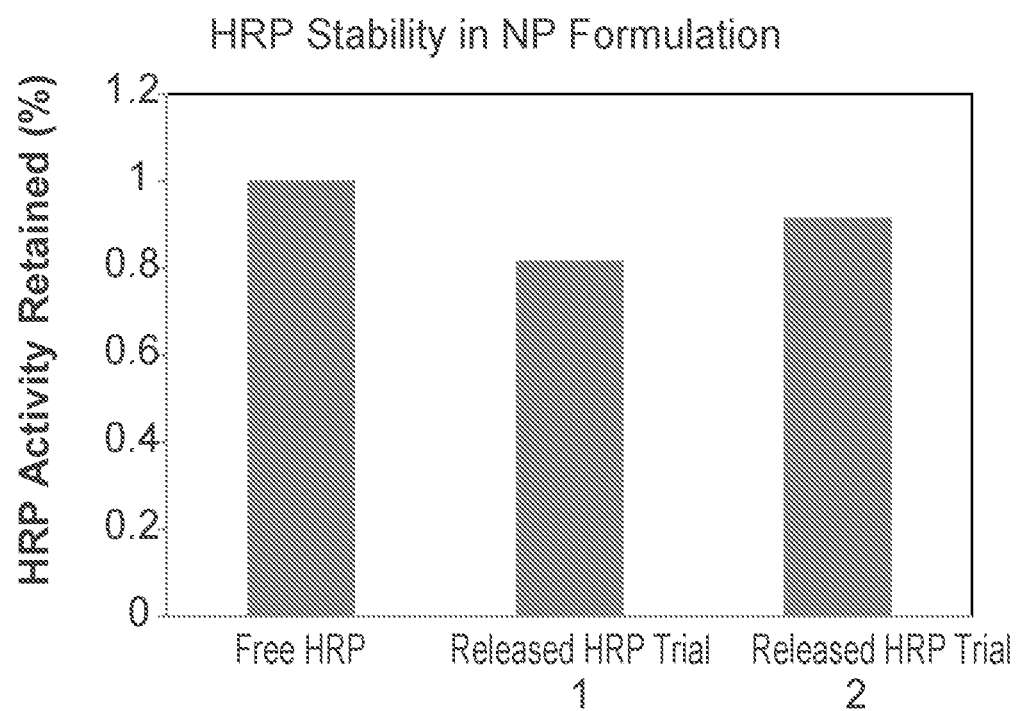
Figure 32C:
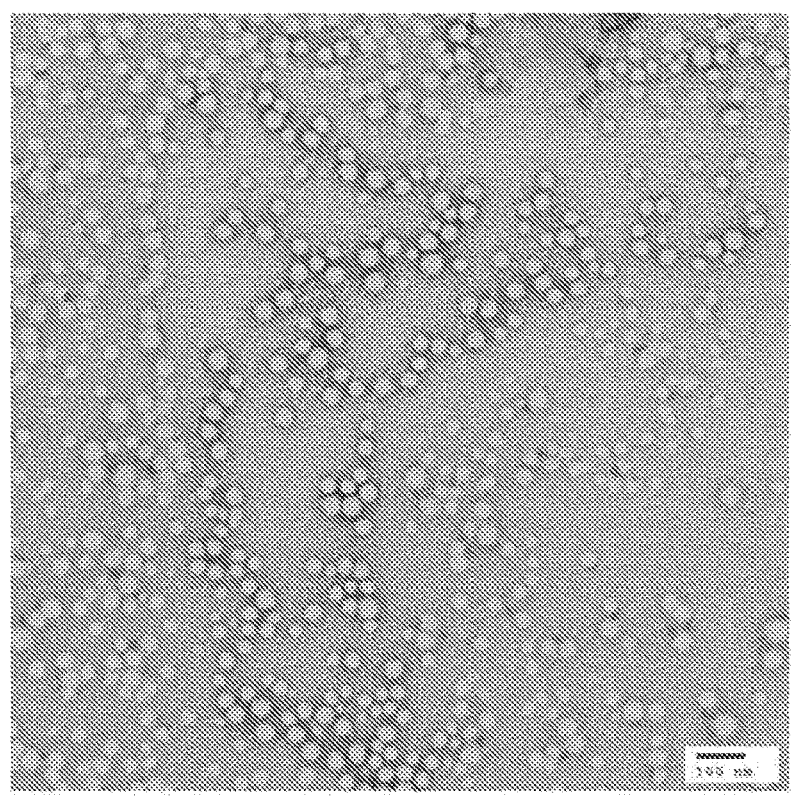
Figure 32D:
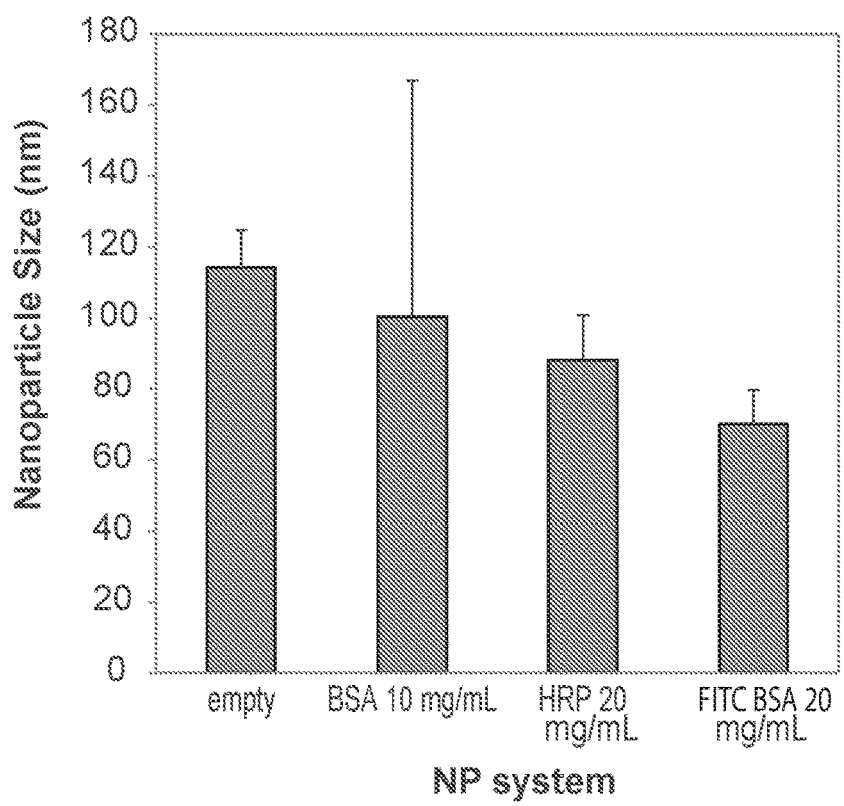

In vitro efficacy study with the particles made in Example 2B using mouse macrophages demonstrates that the miR-21 NPs (both DSPE-PEG NPs and ceramide-PEG NPs) can effectively silence the expression of PDCD4 in macrophage cells (FIG. 32C).

Example 4C

NP-Mediated eGFP mRNA Transfection in PC3 Cells

In vitro study of NP-mediated eGFP mRNA transfection in PC3 cells was conducted as follows. Cells were incubated with naked mRNA, mRNA-loaded NPs and Lipo2K/mRNA complexes (mRNA conc. 0.25 µg/well) for 16 h followed by 24 h incubation in fresh medium. Then the cells were fixed with 4% paraformaldehyde for 15 min at RT followed by staining with DAPI-containing mounting solution. Fluorescence images were taken with FV1000 confocal microscope (FIG. 35).

Transfection efficiency of mRNA-loaded NPs vs. Lipo2K/mRNA complexes in PC3 and DU145 cells was studied as follows. Cells were incubated with the NPs (FIG. 36 (A, C)) or lipo2K/mRNA complexes (FIG. 36 (B, D)) for 16 h. After washing with fresh media, cells were further incubated for 24 h prior to flow cytometric analysis. GFP mRNA was used as model mRNA and 10,000 cells were analyzed.

Example 5

In Vivo Therapeutic Efficacy and Safety Profile

Example 5A

In Vivo Validation of PHB1-Targeted Cancer Therapy

Figure 21A:
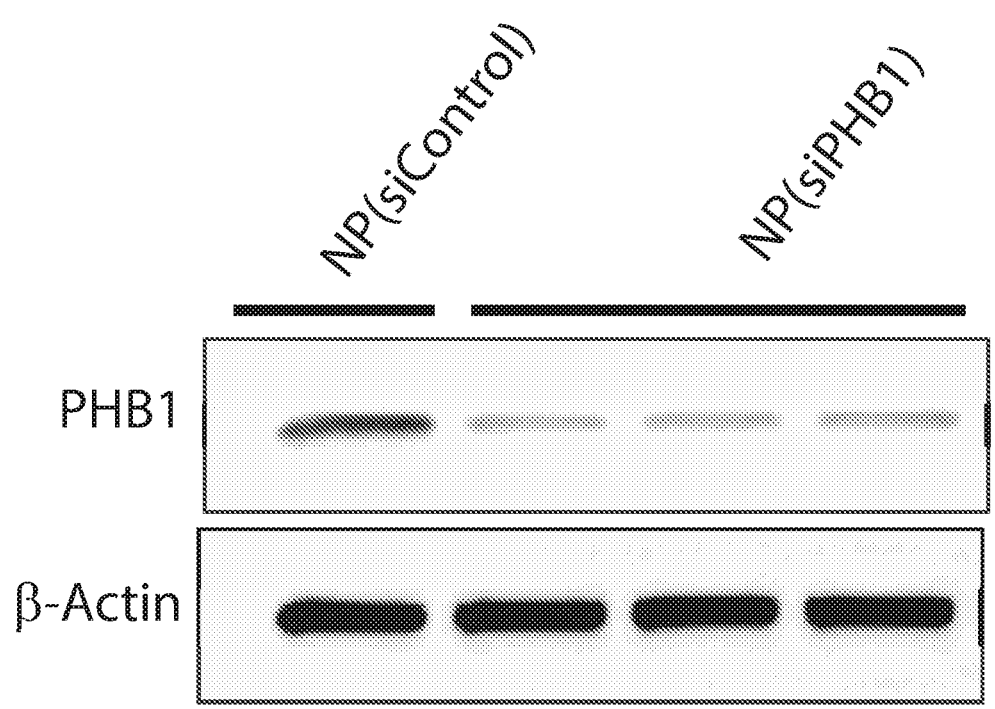
FIG. 21 shows in vivo silencing efficacy and TUNEL of tumor tissue. (A) Western-blot analysis of PHB1 protein level of in NCI-H460 tumor xenografts after intravenous injection of NP(siControl) or NP(siPHB1) (600 µg/kg) for three consecutive days. (B) Quantification of PHB1 protein level in NCI-H460 tumor xenografts. Systemic administration of NP(siPHB1) resulted in ~76.3% decrease in PHB1 expression relative to NP(siControl). (C) Apoptotic cell staining by TUNEL in NCI-H460 tumor tissue. (D) Quantification of TUNEL intensities. Intensity values are normalized to that of saline controls. Data are presented as mean±SD (n=3 per treatment group).
Figure 21B:
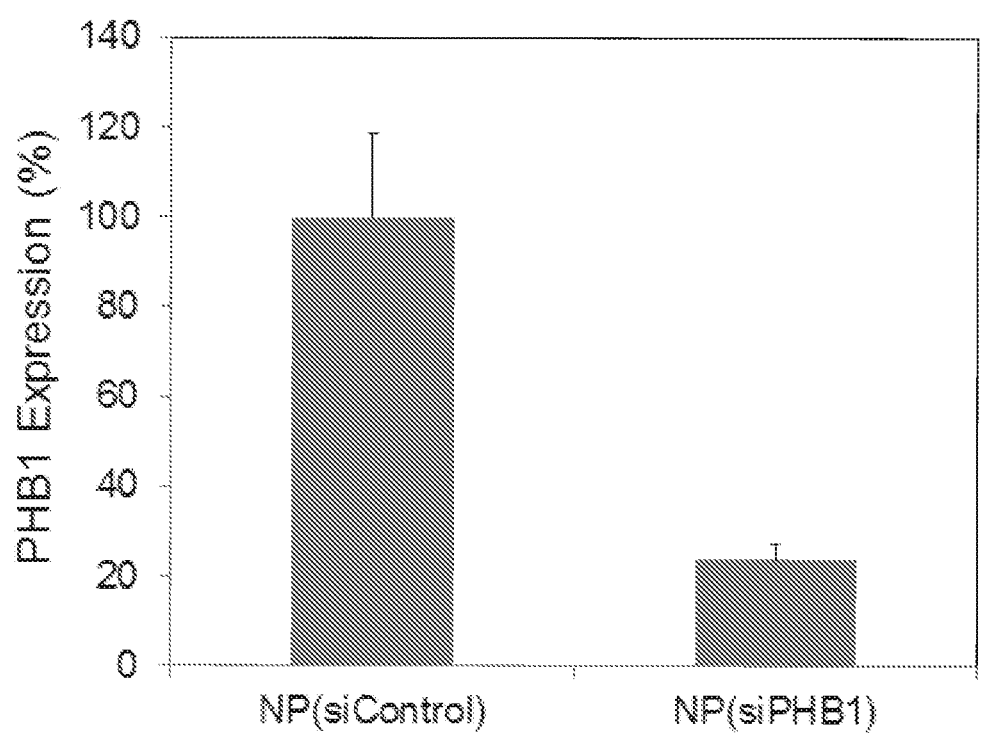
Figure 21C:
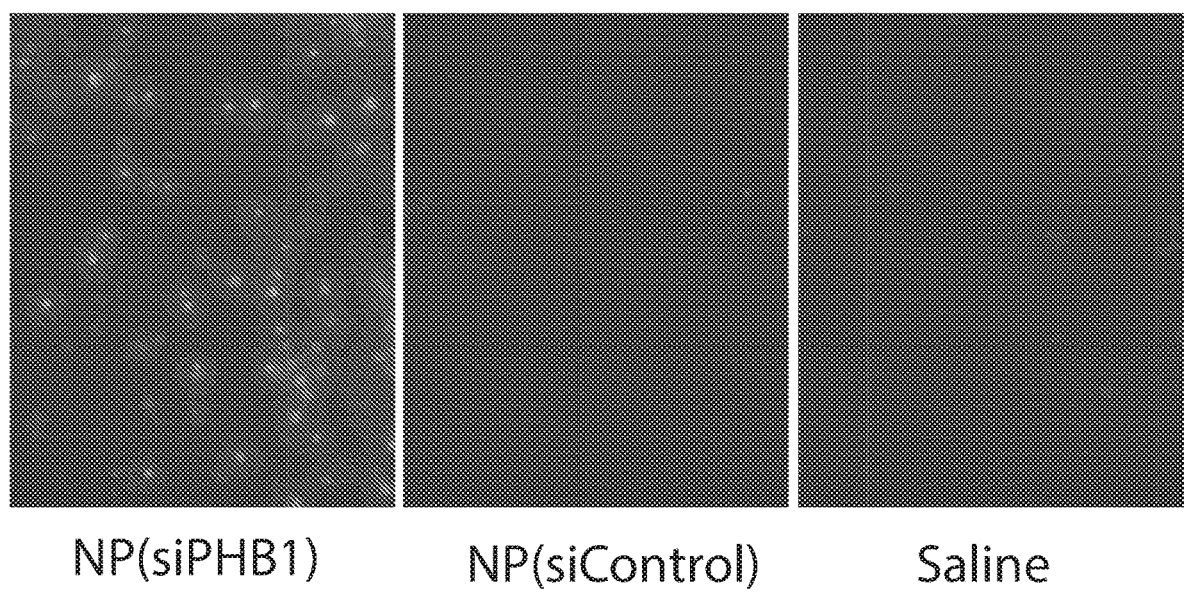
Figure 21D:
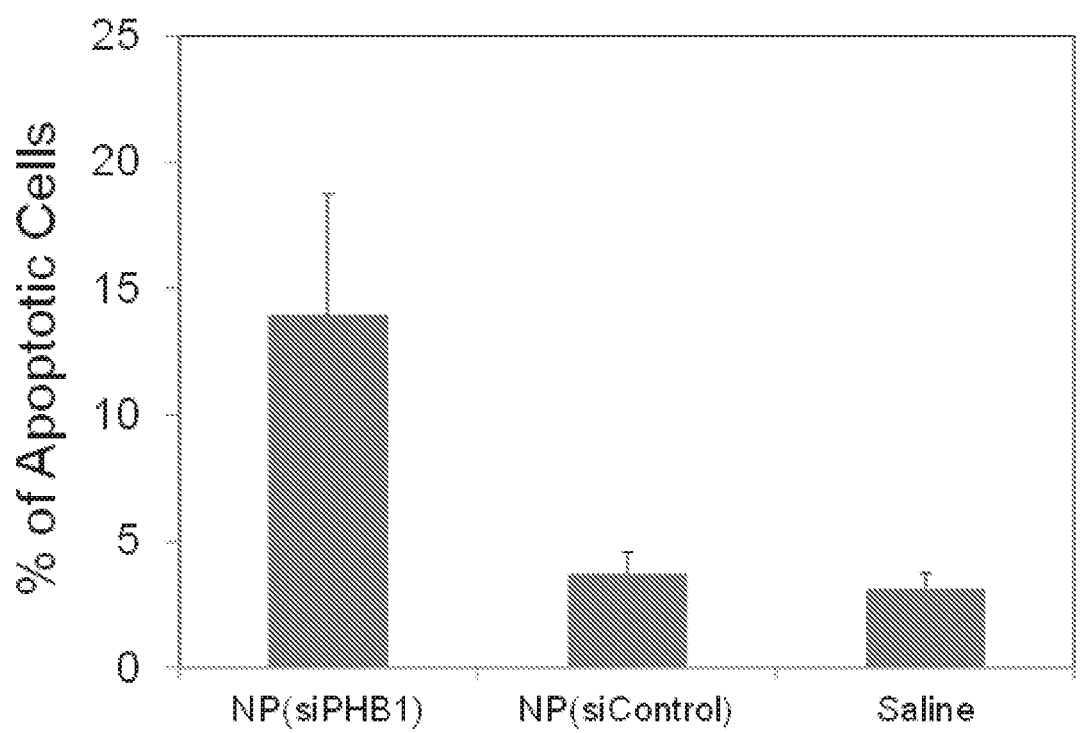
Figure 22A:
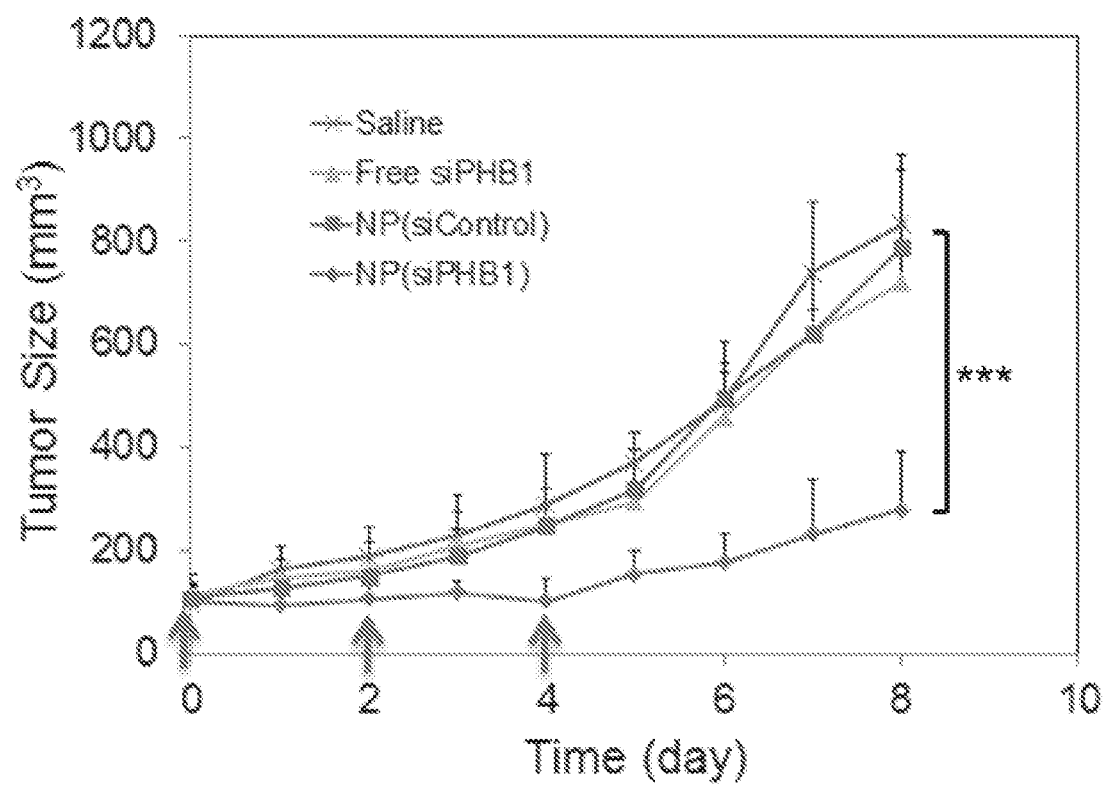
FIG. 22 shows therapeutic efficacy of NP(siPHB1) in NCI-H460 tumor xenograft. (A) Tumor volume change over the course of therapy. Administration schedule was indicated by arrowheads. (B) Images of the tumors at day 8. (C) Weight of NCI-H460 tumor at day 8. (D) Total body weight of NCI-H460 tumor-bearing mice over the course of therapy.
Figure 22B:
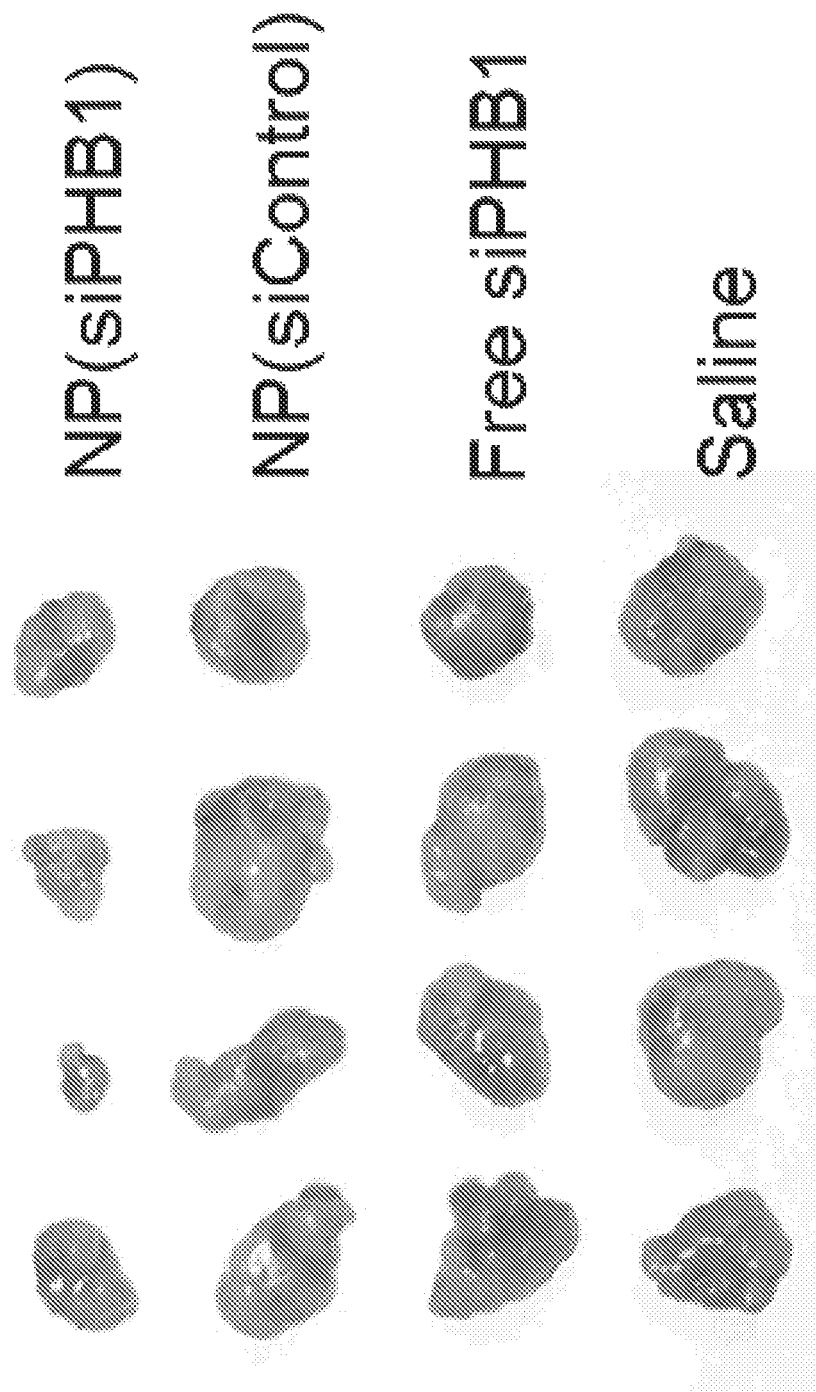
Figure 22C:
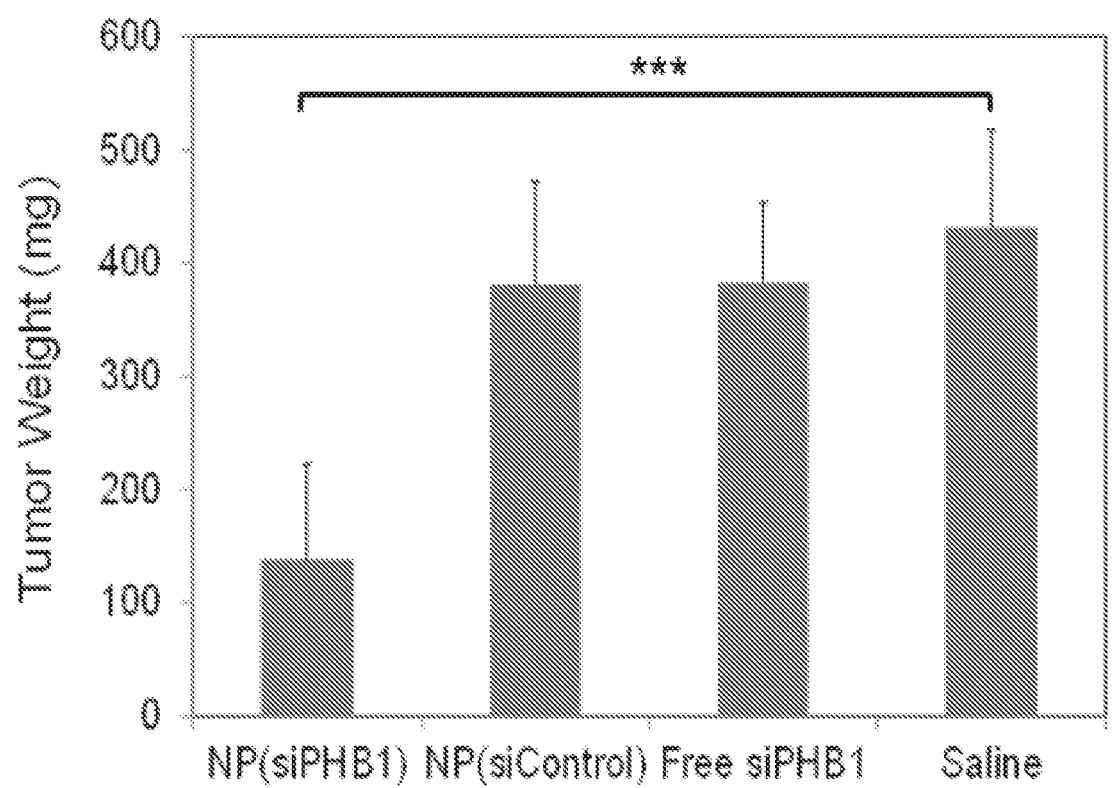
Figure 22D:
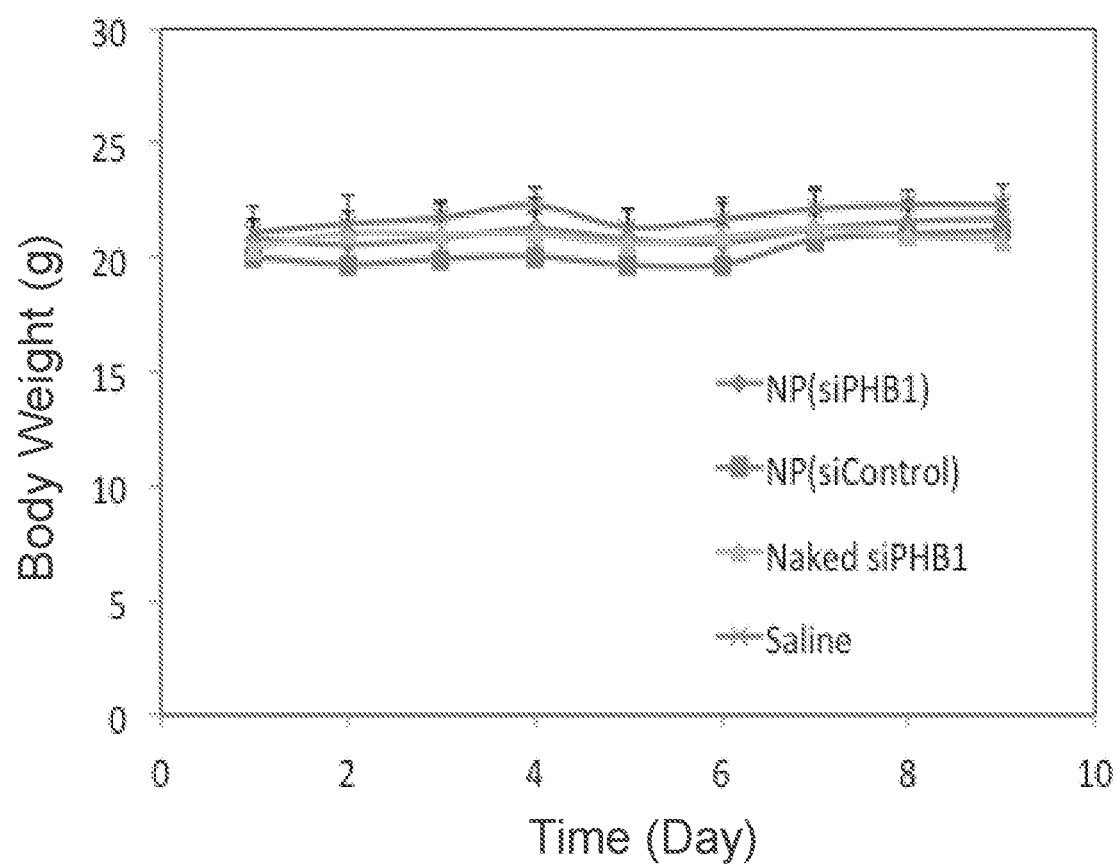
Figure 23A:
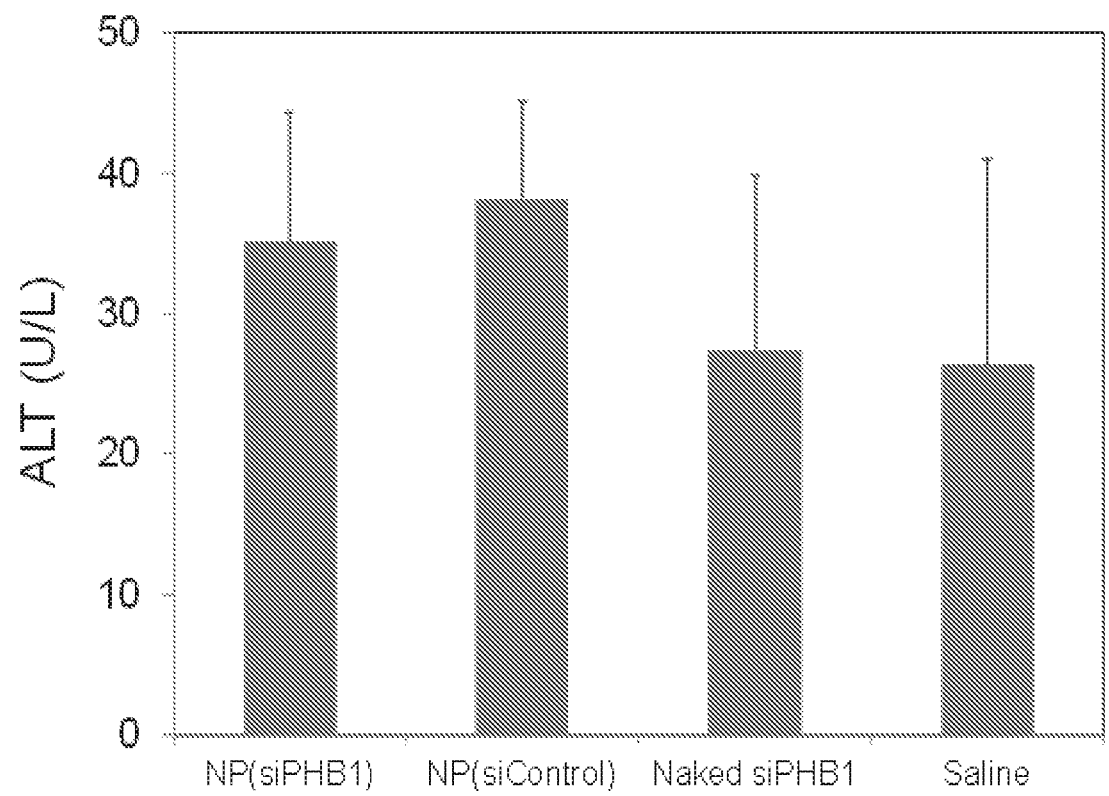
FIG. 23 shows the evaluation of NP toxicity in vivo. Serum levels of (A) alanine aminotransferase (ALT), (B) aspartate aminotransferase (AST), (C) blood urine nitrogen (BUN), (D) creatinine, and (E) troponin-1 were measured after 3 daily intravenous injections (600 µg siRNA/kg).
Figure 23B:
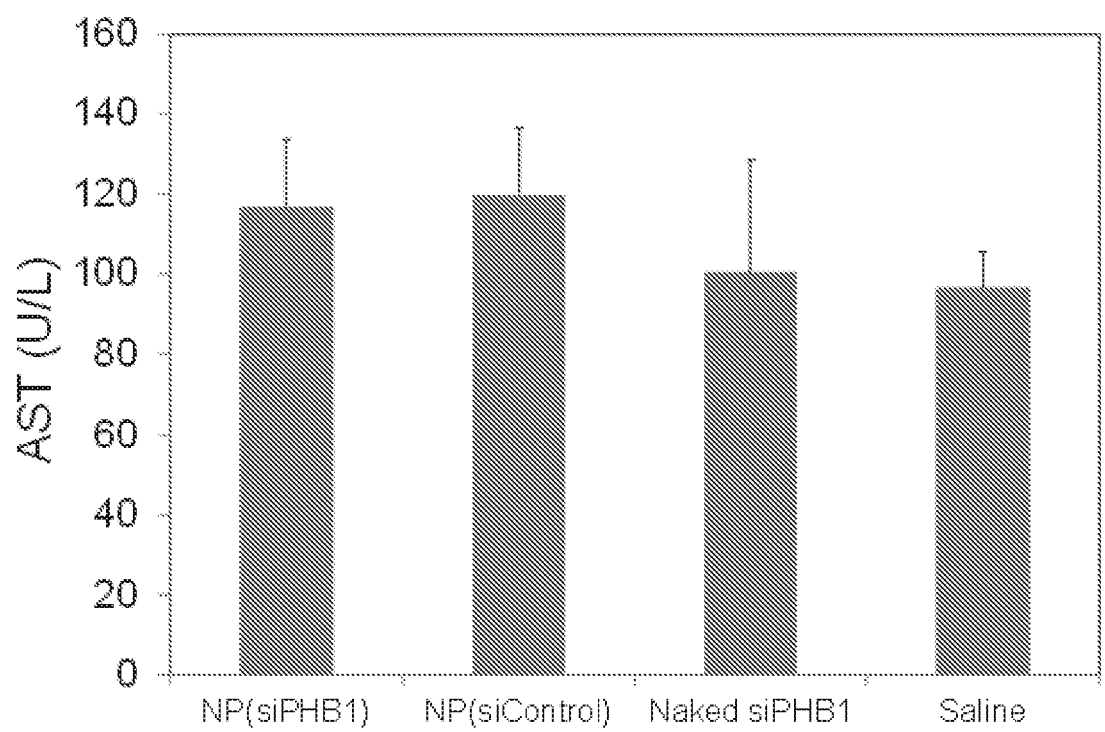
Figure 23C:
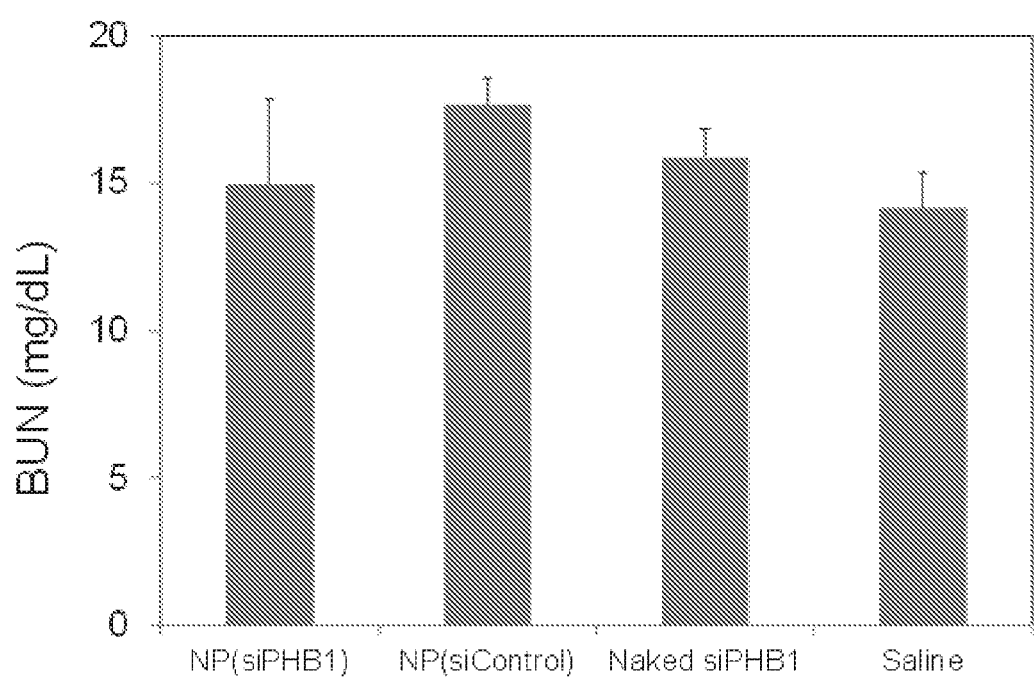
Figure 23D:
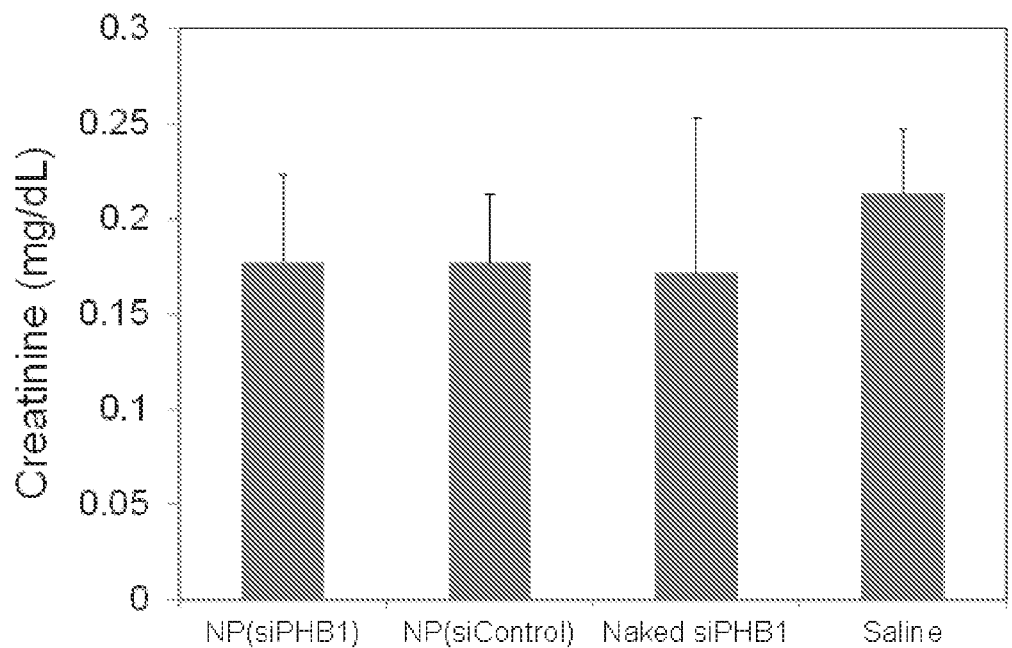
Figure 23E:
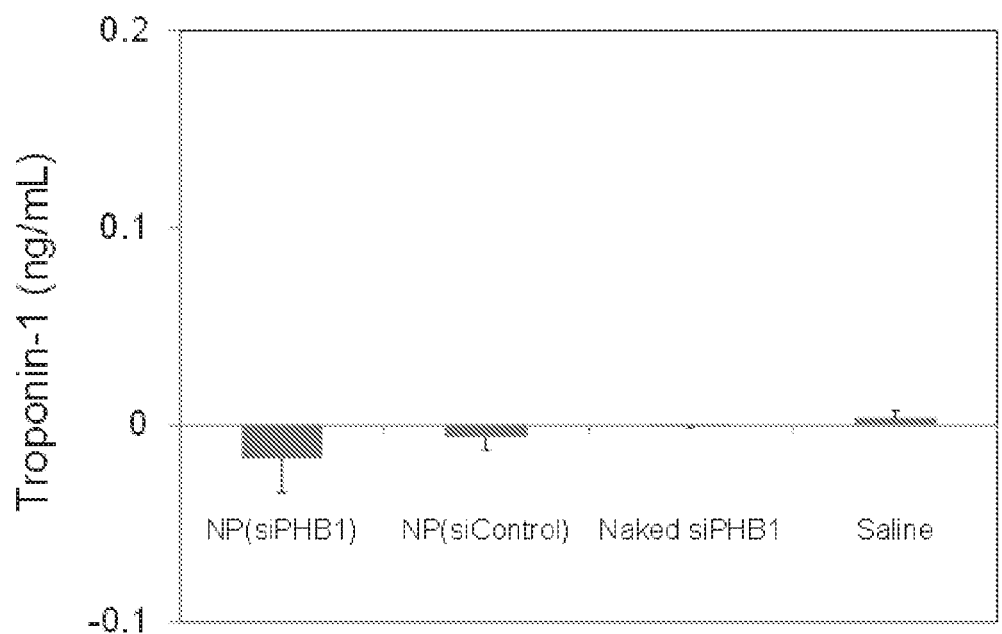

For in vivo validation of PHB1-targeted cancer therapy, whether the NP(siPHB1) is capable of silencing PHB1 in tumor tissue upon systemic administration was tested in a NCI-H460 xenograft model. Mice bearing a subcutaneous NCI-H460 tumor were injected with NP(siPHB1) or NP(siControl) through the tail vein for three consecutive days. For NCI-H460 xenograft model, when the tumor size reached about 100 mm$^3$, mice were randomly divided into four treatment cohorts (four mice per group). Different regimens including (i) saline, (ii) naked siPHB1 (iii) NP(siControl), (iv) NP(siPHB1) were administrated intravenously at a dose of 600 µg siRNA per kilogram of animal weight every 2 days for three times. Two days after the final injection, PHB1 levels in the xenograft tumor were analyzed by Western blot, and the cell apoptosis was evaluated by TUNEL staining. Results showed that NP(siPHB1) induced about 76% decrease in PHB1 expression relative to NP(siControl) (FIG. 21A-21B), and significantly increased tumor cell apoptosis (FIG. 21C). The NP-mediated PHB1 silencing was examined for antitumor effect in the NCI-H460 xenograft. When the tumor size reached about 100 mm$^3$, mice were IV injected with saline, naked siPHB1, NP(siControl), or NP(siPHB1) every 2 days for three times. Similar with the saline-treated group, the tumor grew quickly in mice that received either naked siPHB1 or NP(siControl) (FIG. 22A). In contrast, NP(siPHB1) treatment resulted in a significant suppression of tumor growth. As compared to the three control groups, the average tumor weight in the NP(siPHB1) group was about 70% less at day 16 (FIG. 22B-22C). No significant change in body weight was observed for the four tested groups (FIG. 22D).

Figure 26A:
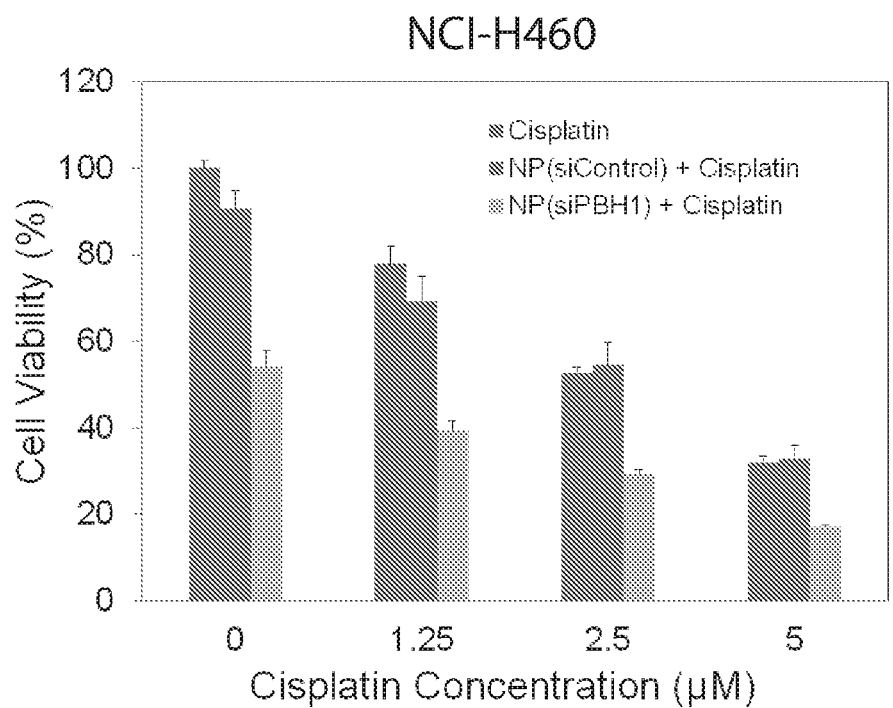
Figure 26B:
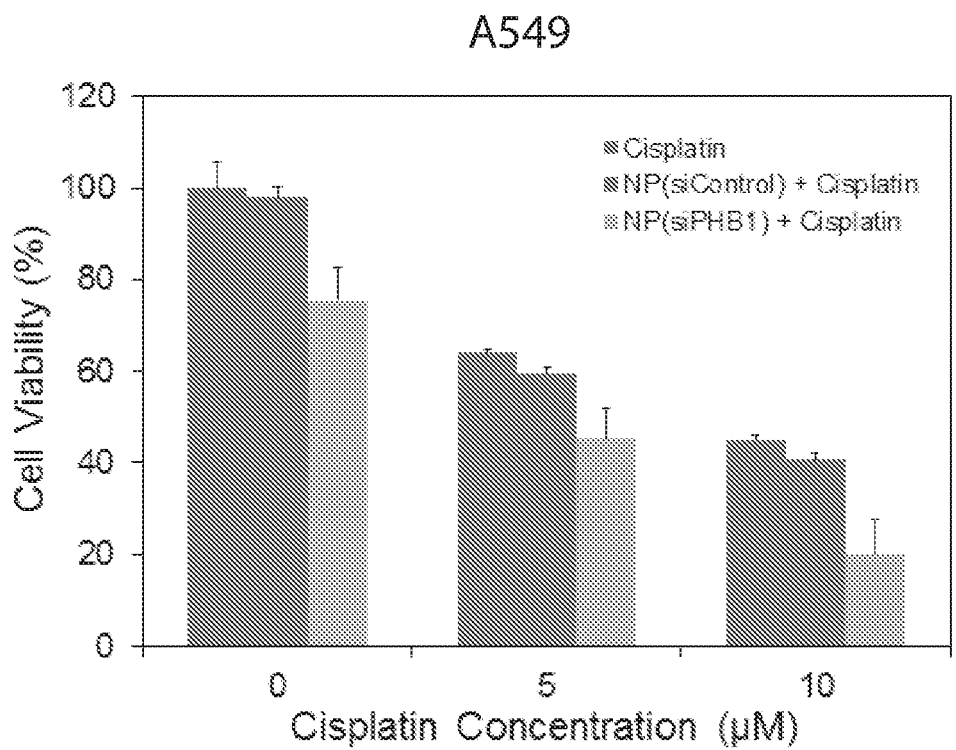

To further test whether the combination of NP(siPHB1) with chemotherapeutic agents could lead to more effective antitumor activity, platinum agents were chosen as a model drug, which is one of the most widely used cytotoxic agents for cancer treatment. From the in vitro cytotoxicity study, enhanced efficacy was observed with the NP(siPHB1)+cisplatin group in A549 (FIG. 26B) and NCI-H460 cells (FIG. 26A). For A549 xenograft model, when the tumor size reached ~100 mm$^3$, mice were randomly divided into five groups (six mice per group). Animals were treated with the following regimens according to the timeline shown in FIG. 27A: (i) saline, (ii) NP(siControl), (iii) NP(siControl)+cisplatin, (iv) NP(siPHB1), and (v) NP(siPHB1)+Cisplatin. NP(siPHB1) and NP(siControl) were administrated intravenously at a dose of 600 µg of siRNA per kilogram of animal weight for each injection. For cisplatin treatment, mice were injected intraperitoneally with cisplatin (3 mg/kg, once per week) prepared in 0.9% USP saline. The tumor size was measured by caliper every other day, and tumor volume was calculated as volume=length×(width)$^2$/2.

For in vivo evaluation of the combination treatment, mice bearing A549 xenograft were treated with saline, NP(siPHB1) or NP(siControl) at an IV dose of 600 µg siRNA/kg per injection with or without cisplatin at an intraperitoneal (IP) dose of 3 mg/kg per week. The administration timeline is shown in FIG. 27A. As can be seen, tumor growth was significantly inhibited by NP(siPHB1), more effective than cisplatin (FIG. 27B and FIG. 27D). Further, the combination of cisplatin and NP(siPHB1) almost completely inhibited tumor growth during the treatment period. Mice that received the combination treatment survived the entire 64-day duration (FIG. 27C). In contrast, all of the mice in the saline and NP(siControl) groups died after 54 days. These results suggest that effective PHB1 silencing by the long-circulating RNAi NPs represents a potential strategy for NSCLC treatment, which may be further combined with an additional chemotherapeutic for enhanced therapeutic efficacy.

Figure 24:
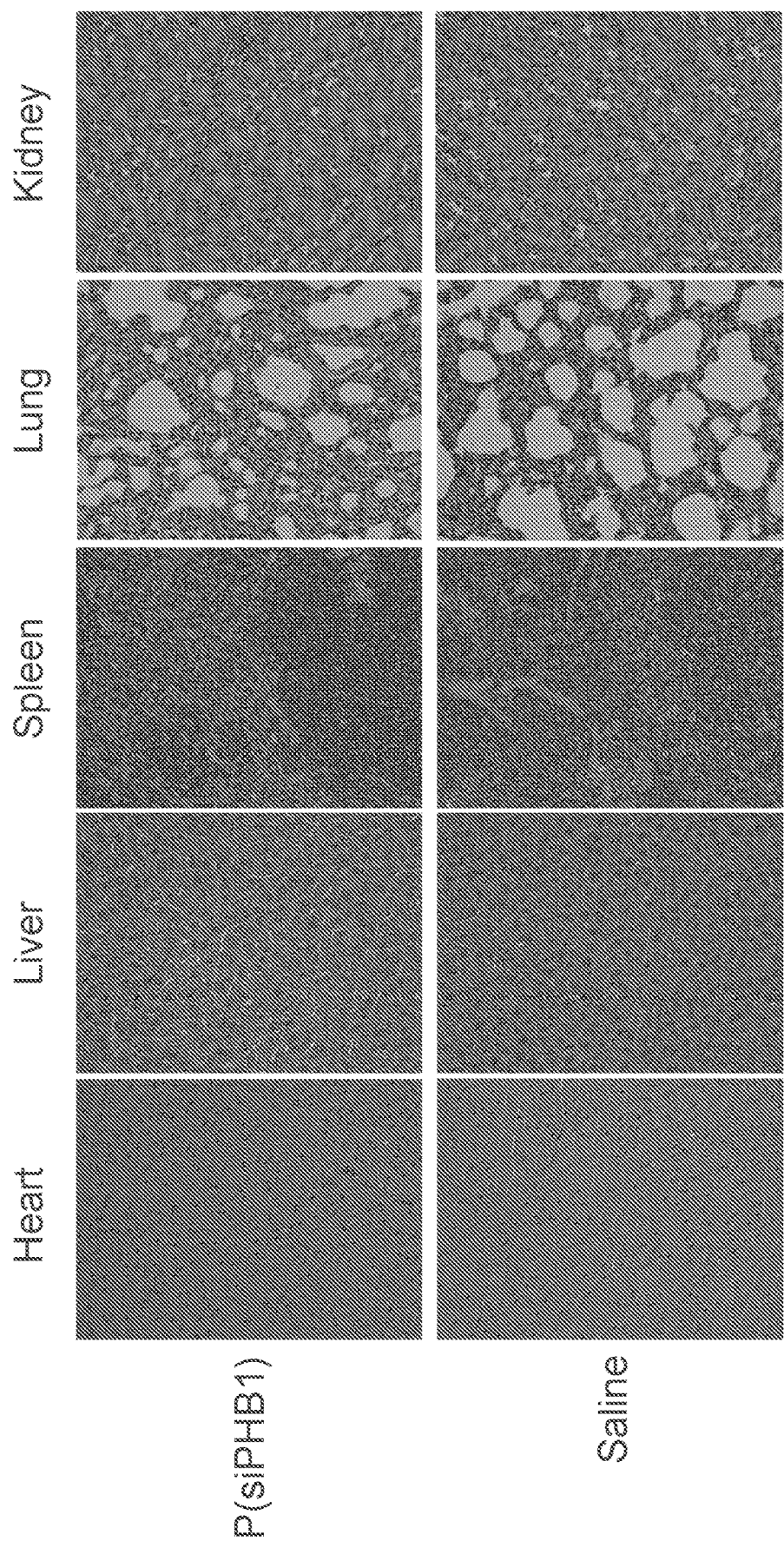
FIG. 24 shows hematoxylin and eosin (H&E) staining of tissue sections of major organs after NP(siPHB1) treatment.

In addition to therapeutic efficacy, in vivo side effects of the NP(siPHB1) were evaluated. For in vivo toxicity study, normal BALB/c mice were administered with 3 daily intravenous injections of (i) saline, (ii) naked siPHB1, (iii) NP(siControl), or (iv) NP(siPHB1), at 600 µg siRNA/kg animal. Blood was drawn retroorbitally and serum was separated for hematologic examination. The blood level of aspartate aminotransferase (AST), alanine aminotransferase (ALT), blood urine nitrogen (BUN), creatinine, and troponin-1 was measured by the assay kits according to the manufacturer's protocol (AST: BioVision; ALT and Creatitine: Cayman Chemical; BUN: Arbor Assays; and troponin-1: Life Diagnostics). For histology study, organs were harvested 2 days after the final injection, fixed with 4% paraformaldehyde, and embedded in paraffin. Tissue sections were stained with H&E. Different hematological parameters, including alanine aminotransferase (ALT), aspartate aminotransferase (AST), blood urine nitrogen (BUN), creatinine, and Troponin-1, were in the normal range and no significant difference was found between all tested groups, indicating the NP(siPHB1) did not elicit toxicity in liver, kidney and heart at the therapeutic dose used for efficacy studies above (FIG. 23A-23E). The H&E staining results demonstrated no noticeable histological change in the tissues from heart, liver, spleen, lung, and kidney between saline and NP(siPHB1) groups, indicating no organ toxicity (FIG. 24).

To exclude the possibility that the antitumor effect of NP(siPHB1) might be confounded by siRNA-mediated immune stimulation, the immunostimulatory effect of the NPs in immunocompetent BALB/c mice was studied. BALB/c immunocompetent mice were injected intravenously with saline, naked siPHB1 (600 µg siRNA/kg), blank NPs, or siPHB1 NPs. Serum samples obtained 6 hours or 24 hours post injections were processed for measurements of representative cytokines (TNF-α, IL-6 and IL-12) by the enzyme-linked immunosorbent assay or ELISA (PBL Biomedical Laboratories and BD Biosciences) in accordance with the manufacturer's instructions. At 6 and 24 hours post IV injection of saline, naked siPHB1, blank NP, or NP(siPHB1), serum samples were collected and representative cytokines were quantified, including tumor necrosis factor-alpha (TNF-α), interleukin-6 (IL-6) and IL-12. No apparent change in IL-12 level was observed for all the groups. While serum levels of TNF-α and IL-6 were increased for blank NP and NP(siPHB1) 6 hours post injection (FIG. 25A-25C), there was no significant difference of the cytokine levels between the blank NP group and the NP(siPHB1) one, suggesting that the TNF-α and IL-6 responses may be attributed to the NP itself rather than encapsulated siRNA. Both TNF-α and IL-6 concentrations in the blank NP and NP(siPHB1) groups returned to the baseline level of saline group after 24 hours.

Example 5B

Study of NP(siMYC) in PC3 Xenograft Model

I. Therapeutic Efficacy of NP(siMYC) in PC3 Xenograft Model

Therapeutic efficacy of NP (siMYC) in the PC3 xenograft tumor model was studied by injecting mice with PBS (placebo), NP (siControl), NP (siControl)+cisplatin, NP (sic-MYC), and NP (sic-MYC)+cisplatin. The results of the study are shown in FIG. 38. FIG. 38A shows injection timeline. NP(siMYC) was injected i.v. and cisplatin was injected i.p. FIG. 38 (B, C) shows inhibition of PC3 tumor growth after treatment with PBS, NP (siControl), NP (siControl)+cisplatin, NP (siMYC), and NP (siMYC)+cisplatin (n=7 per group). FIG. 38D shows digital photograph of tumors for different groups obtained at the end of experiment (from left to right: PBS control, NP (siControl), NP (siControl)+cisplatin, NP (siMYC), and NP (siMYC)+cisplatin). FIG. 38E shows body weight of tumor-bearing mice over the course of therapy. As can be seen in FIG. 38B-D, NP(siControl) treatment did not impact the tumor growth, whereas the tumor growth of mice injected with NP(siMYC) was found to be significantly inhibited compared to that of either control group or NP(siControl) group. Furthermore, combination treatment with NP(siMYC) and cisplatin further inhibited tumor growth during the treatment period. No obvious change in body weight was observed for all groups (FIG. 38E). These results suggest the potential of MYC as a therapeutic target and of the combination therapy of MYC siRNA with cisplatin in PCa treatment.

II. MYC Silencing Study in PC3 Xenograft Model

The silencing of MYC expression was examined upon intravenous administration of NP(siMYC) in PC3 xenograft mouse model. Athymic nude mice harboring subcutaneous PC3 tumor were intravenously administered with NP(siMYC) or NP(siControl) for three consecutive days. Two days after the final injection, MYC level in the tumor tissue was analyzed by western blotting, immunohistochemistry (IHC) and immunofluorescence (IF). The study of MYC knockdown in the PC3 xenograft tumor model is shown in FIG. 37. MYC protein level in the tumor tissues tested by (A) western blot analysis, (B) immunohistochemistry, and (C) immunofluorescence after treatment of NP(siControl) vs. NP(siMYC). NP(siMYC) induced ~70% decrease in MYC level relative to the NP(siControl) group.

Example 5C

Time-Dependent In Vivo NIR Imaging of Tumor and Lymph Node Mapping

BRAF$^{V600E}$ mutated 8505C tumor-bearing mouse was studied using near infra-red fluorescence imaging (NIR). For the xenograft tumor model development, BRAF$^{V600E}$ mutated 8505C cells were cultured in RPMI-1640 supplemented with 10% FBS at 37° C. in an atmosphere of 5% $CO_2$ and 95% air. For the ATC tumor xenograft model, $2\times10^6$ BRAF$^{V600E}$ mutated 8505C cells were suspended in 200 µL of 50% Matrigel (BD Matrigel™) with serum-free culture medium (1:1 v/v %), and then inoculated subcutaneously on the bilateral flanks of 4-week-old female athymic nude mice. The mice were used for further experiments when the tumors have grown to 5-10 mm in diameter.

Figure 39A:
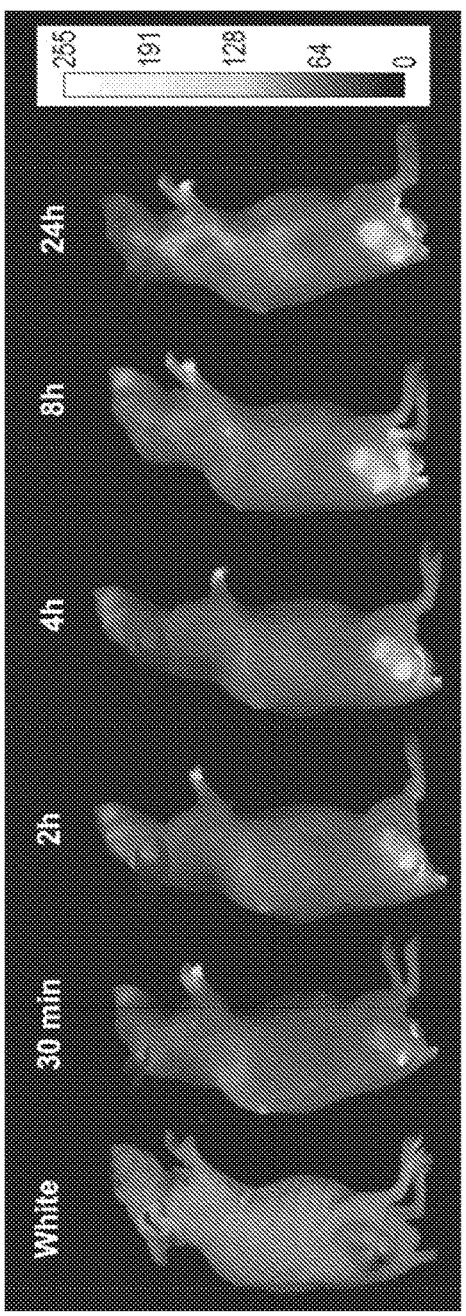
Figure 39B:
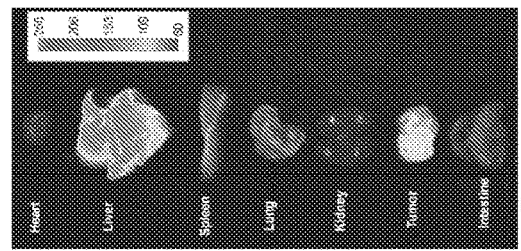
Figure 39C:
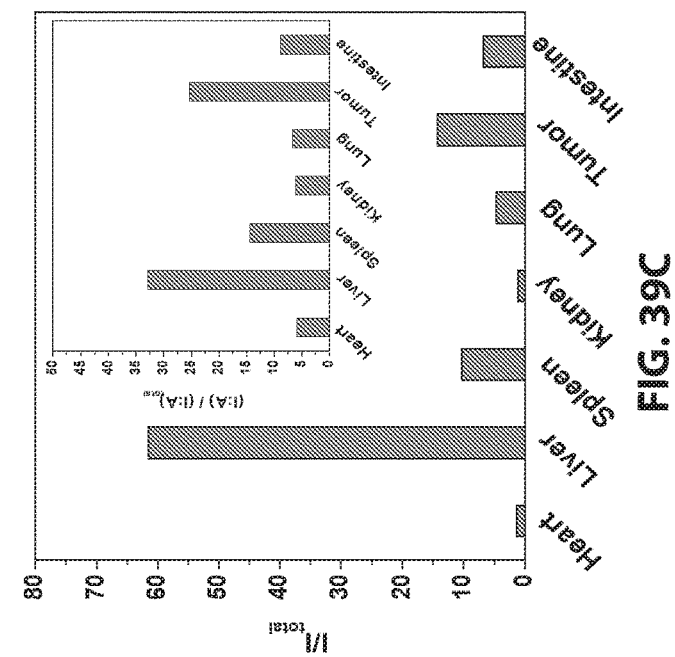

FIG. 39A shows time-dependent fluorescence imaging of BRAF$^{V600E}$ mutated 8505C tumor-bearing mouse after a single dose injection of NIR NPs. The great blood vessels could be clearly visualized even after 4 h post-injection under NIR irradiation, due to the prolonged circulation of nanoparticles in blood. This result is of great significance and shows selective accumulation of NPs in tumor. The results of these studies may also be helpful in the imaging-guided surgery, during which the NPs can provide adequate contrast between vessels and around normal tissues as well as between tumors and normal tissues, avoiding the risk of damage to the vessels and shortening the surgical time. As time increased, NPs were gradually cleared from the blood and showed an increasing tendency of accumulation in the tumor. FIG. 39B shows NIR fluorescence of organs from BRAF$^{V600E}$ mutated 8505C tumor-bearing mouse at 24 h post injection of NIR NPs. FIG. 39C shows quantitative biodistribution analysis of NPs from organs of BRAF$^{V600E}$ mutated 8505C tumor-bearing mouse (shown in FIG. 39B). Under the irradiation ($v_{max}$=740 nm), the tumor showed strong NIR fluorescence in sharp contrast to organs including heart, spleen, kidney and lung. The ratio between the intensity and area of accumulation of NPs for tumor was comparable to that of liver.

Figure 39D:
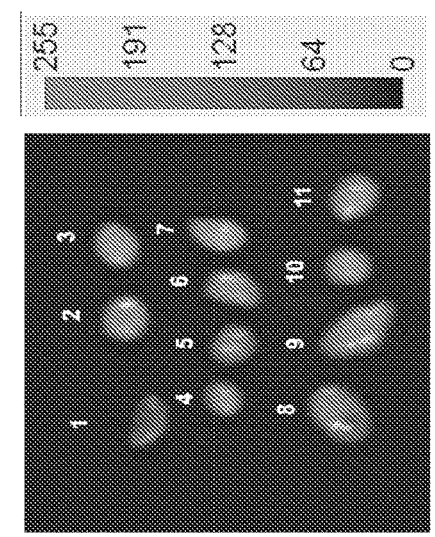
Figure 39E:
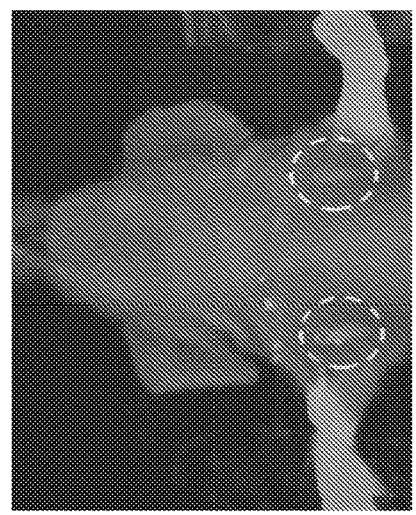

In addition to tumor imaging, prolonged circulating in blood would make the NIR NPs highly suitable for lymph node delivery to improve cancer staging, which minimizes unnecessary surgery (*Angew. Chem. Int. Ed.* 51, 1437-1442 (2012)). To evaluate whether the NIR NPs have the potential in sentinel lymph node (SLN) mapping, NIR NPs were injected subcutaneously into the forepaws of mouse. Within 10 min, strong NIR fluorescence from the axillary lymph nodes was observed without surgical opening (FIG. 39E), illustrating that nanoparticles have migrated to the lymph nodes through lymphatic drainage. Furthermore, after tail-vein injection, NPs could also efficiently label other lymph nodes including axillary lymph node, inguinal lymph node, lateral thoracic lymph node, and neck lymph nodes. FIG. 39D shows NIR fluorescence imaging of lymph nodes at 24 h after intravenous injection of NIR NPs (1, a small piece of muscle; 2, 3 inguinal lymph nodes; 4-7: neck lymph nodes; 8, 9: lateral thoracic lymph nodes; and 10, 11: axillary lymph nodes).

Example 5D

In Vivo Inhibition of 8505C Xenograft Tumor Growth

The tumor growth inhibition effect of NP(siBRAF) was evaluated in BRAF$^{V600E}$ mutated 8505C xenograft tumor model. When the tumor size reached 50-100 mm$^3$, mice were randomly divided into three treatment groups (4 mice per group). Different regimens including (i) saline (placebo), (ii) NP(siControl), and (iii) NP(siBRAF) were administrated intravenously at a dose of 600 µg siRNA per kilogram of animal weight every other day for three times. The tumor size of the xenograft tumor model was measured by a caliper every other day, and the tumor volume was calculated as: V=tumor length×(tumor width)$^2$/2. Relative tumor volumes were calculated as V/V$_0$ (V$_0$ was the tumor volume when the treatment was initiated).

Figure 40A:
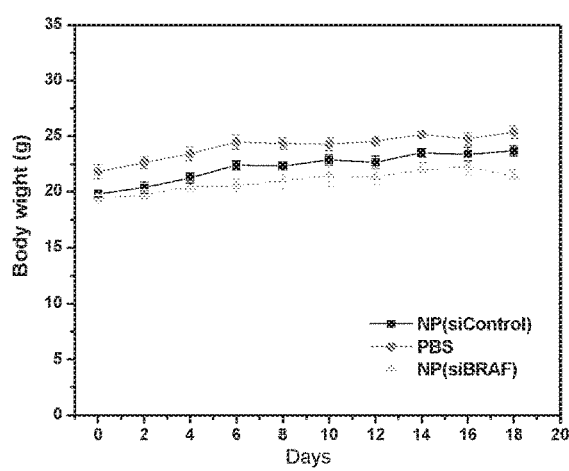
Figure 40C:
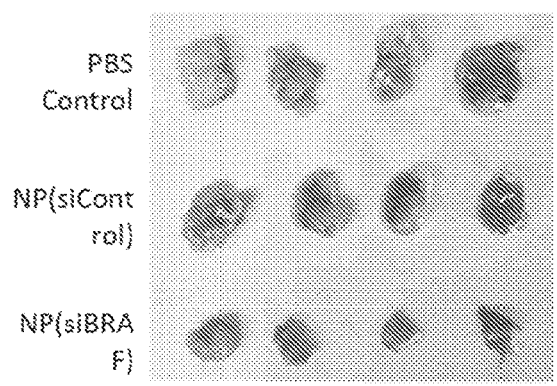
Figure 40B:
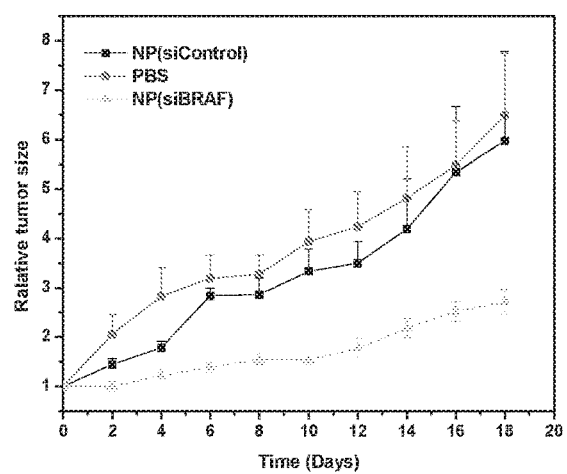
Figure 40D:
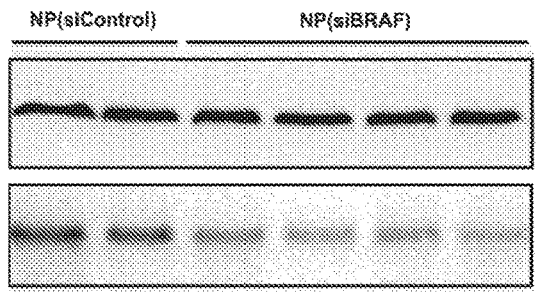
Figure 40E:
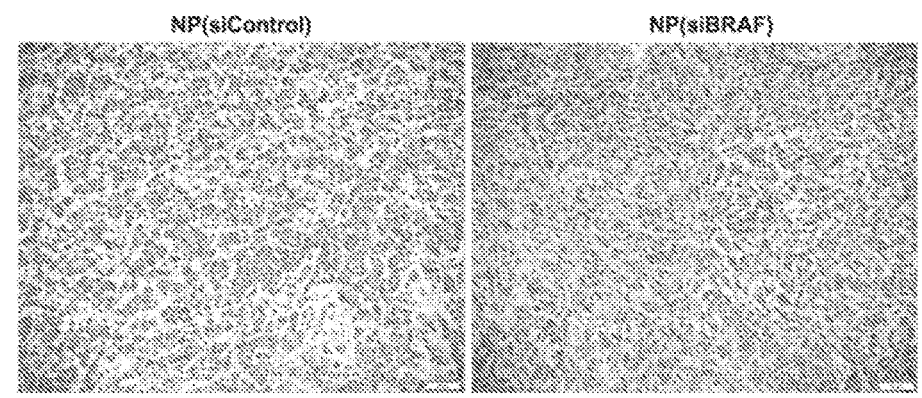

FIG. 40A shows similar body weight changes of the BRAF$^{V600E}$ mutated 8505C tumor-bearing mice that were treated with saline (PBS, placebo), NP (siControl), and NP (siBRAF), indicating the safety of the NPs. FIG. 40B shows tumor growth curve of PBS-, NP (siControl)-, and NP (siBRAF)-treated BRAF$^{V600E}$ mutated 8505C tumor bearing mice. The timing of the three i.v. injections was indicated by the arrows. The tumor growth of mice injected with NP(siBRAF) was found to be significantly inhibited compared to that of either control group or NP(siControl) group. FIG. 40C shows representative picture of tumors obtained from the mice at the terminal of study for FIG. 40B. FIG. 40D shows the Western blot analysis of BRAF expression in BRAF$^{V600E}$ mutated 8505C tumor tissue after systemic treatment of NP (siControl) and NP (siBRAF). Compared to NPs formulated control siRNA, NPs loaded with siBRAF showed approximately 60% down-regulation of the BRAF expression. The silencing efficacy is father demonstrated in FIG. 40E showing immunochemical microphotographs of BRAF expression in BRAF$^{V600E}$ mutated 8505C tumor tissue after systemic treatment of NP (siControl) or NP (siBRAF).

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A particle comprising:
 a water-insoluble polymeric core; and
 a nucleic acid and a first amphiphile comprising an amino dendrimer comprising a lipophilic moiety selected from the group consisting of G0-C14 dendrimer, polypropyleneimine tetramine dendrimer generation 1, and ethylenediamine branched polyethyleneimine within the core.

2. The particle of claim 1, further comprising a shell comprising a second amphiphile surrounding the water-insoluble polymeric core.

3. The particle of claim 1, wherein the water-insoluble polymeric core comprises one or more polymers selected from a polylactic acid, a polyglycolic acid, and a copolymer of lactic acid and glycolic acid.

4. The particle of claim 2, wherein the second amphiphile comprises one or more compounds selected from neutral, cationic and anionic lipids, PEG-phospholipid, and a PEG-ceramide.

5. The particle of claim 4, wherein the neutral, cationic or anionic lipid is lecithin; the PEG-phospholipid is 1,2-distearoyl-sn-glycero-3-phosphoethanolamine-N-[methoxy (polyethylene glycol)-3000] or 1,2-distearoyl-sn-glycero-3-phosphoethanolamine-N-[methoxy(polyethylene glycol)-5000]; and the PEG-ceramide is N-palmitoyl-sphingosine-1-{succinyl[methoxy(polyethylene glycol)5000]}.

6. A particle prepared by a process comprising:
 obtaining a first solution comprising a water-insoluble polymer, a nucleic acid and a first amphiphile comprising an amino dendrimer comprising a lipophilic moiety selected from the group consisting of G0-C14 dendrimer, polypropyleneimine tetramine dendrimer generation 1, and ethylenediamine branched polyethyleneimine in a water-miscible solvent; and
 mixing the first solution with an aqueous second solution to form an aqueous composition comprising the particle.

7. The particle of claim 6, wherein the process further comprises mixing the aqueous composition with a solution comprising a second amphiphile to form a shell surrounding the core.

8. A pharmaceutical composition comprising the particle of claim 1, and a pharmaceutically acceptable carrier.

9. A method of preparing a particle according to claim 1, the method comprising:
 obtaining a first solution comprising a water-insoluble polymer, a nucleic acid and a first amphiphile comprising an amino dendrimer comprising a lipophilic moiety selected from the group consisting of G0-C14 dendrimer, polypropyleneimine tetramine dendrimer generation 1, and ethylenediamine branched polyethyleneimine in a water-miscible solvent; and
 mixing the first solution with an aqueous second solution to form an aqueous composition comprising the particle.

10. The method of claim 9, further comprising mixing the aqueous composition with a solution comprising a second amphiphile to form a shell surrounding the core.

11. A method of administering a nucleic acid to a subject, the method comprising administering to the subject in need thereof a pharmaceutical composition according to claim 8.

12. The particle of claim 1, further comprising a small-molecule drug within the core.

13. The particle of claim 6, wherein the first solution further comprises a small-molecule drug.

14. The method of claim 9, wherein the first solution further comprises a small-molecule drug.

15. The particle of claim 1 or 6, wherein the nucleic acid comprises siRNA.

16. The particle of claim 1 or 6, wherein the nucleic acid comprises mRNA.

17. The particle of claim 1 or 6, wherein the nucleic acid comprises microRNA.

18. The method of claim 9, wherein the nucleic acid comprises siRNA.

19. The method of claim 9, wherein the nucleic acid comprises mRNA.

20. The method of claim 9, wherein the nucleic acid comprises microRNA.

* * * * *